United States Patent
Walensky et al.

(10) Patent No.: US 9,079,970 B2
(45) Date of Patent: Jul. 14, 2015

(54) METHODS AND COMPOSITIONS FOR SPECIFIC MODULATION OF MCL-1

(75) Inventors: Loren D. Walensky, Newton, MA (US); Michelle L. Stewart, Brookline, MA (US)

(73) Assignee: Dana Farber Cancer Institute, Inc., Boston, MA (US)

( * ) Notice: Subject to any disclaimer, the term of this patent is extended or adjusted under 35 U.S.C. 154(b) by 814 days.

(21) Appl. No.: 13/133,883

(22) PCT Filed: Dec. 9, 2009

(86) PCT No.: PCT/US2009/067363
§ 371 (c)(1), (2), (4) Date: Nov. 4, 2011

(87) PCT Pub. No.: WO2010/068684
PCT Pub. Date: Jun. 17, 2010

(65) Prior Publication Data
US 2012/0172285 A1    Jul. 5, 2012

Related U.S. Application Data

(60) Provisional application No. 61/120,988, filed on Dec. 9, 2008.

(51) Int. Cl.
```
A61K 38/00    (2006.01)
A61P 5/00     (2006.01)
C07K 14/47    (2006.01)
A61K 31/00    (2006.01)
G01N 33/50    (2006.01)
G01N 33/574   (2006.01)
```

(52) U.S. Cl.
CPC ............. *C07K 14/4747* (2013.01); *A61K 31/00* (2013.01); *G01N 33/5011* (2013.01); *G01N 33/57484* (2013.01); *A61K 38/00* (2013.01)

(58) Field of Classification Search
CPC ... A61K 31/00; A61K 38/00; A61K 2300/00; C07K 14/4747; G01N 33/57484
See application file for complete search history.

(56) References Cited

U.S. PATENT DOCUMENTS

| 5,470,955 A | 11/1995 | Craig |
| 6,703,382 B2 | 3/2004 | Wang et al. |
| 2005/0250680 A1 | 11/2005 | Walensky et al. |

FOREIGN PATENT DOCUMENTS

| JP | 2008501623 A | 1/2008 |
| WO | WO2005/044839 A2 | 5/2005 |
| WO | WO2008/137633 | 11/2008 |

OTHER PUBLICATIONS

Guillaume Lessene et al., "BCL-2 family antagonists for cancer therapy," Nature Reviews 7:989-1000 (2008).
Loren D. Walensky et al., "Activation of Apoptosis in Vivo by a Hydrocarbon-Stapled BH3 Helix," Science 305:1466-1470 (2004).
Michelle L. Stewart et al., "The MCL-1 BH3 helix is an exclusive MCL-1 inhibitor and apoptosis sensitizer," Nature Chemical Biology 6:595-601 (2010).
Gregory A. Bird et al., Synthesis and Biophysical Characterizaton of Stabilized a-Helices of BCL-2 Domains, Methods in Enzymology, vol. 446, pp. 369-386, 2008.
International Search Report for corresponding PCT Application No. PCT/US2009/067363 (mailed Aug. 19, 2010).
JPO Notification of Reason for Refusal in Japanese Application No. 2011-539807, dated May 19, 2014 (with English translation).

*Primary Examiner* — Marcela M Cordero Garcia
(74) *Attorney, Agent, or Firm* — Fish & Richardson P.C.

(57) ABSTRACT

A series of stapled BCL-2 family peptide helices were identified as able to target the survival protein MCL-I with high affinity and a subset with unprecedented selectivity. Agents and methods for selective pharmacologic neutralization of MCL-I are provided for drug discovery and therapeutic uses, including use in overcoming the apoptotic resistance of cancer and other diseases associated with impaired cell death.

4 Claims, 23 Drawing Sheets

FIGURE 1
A
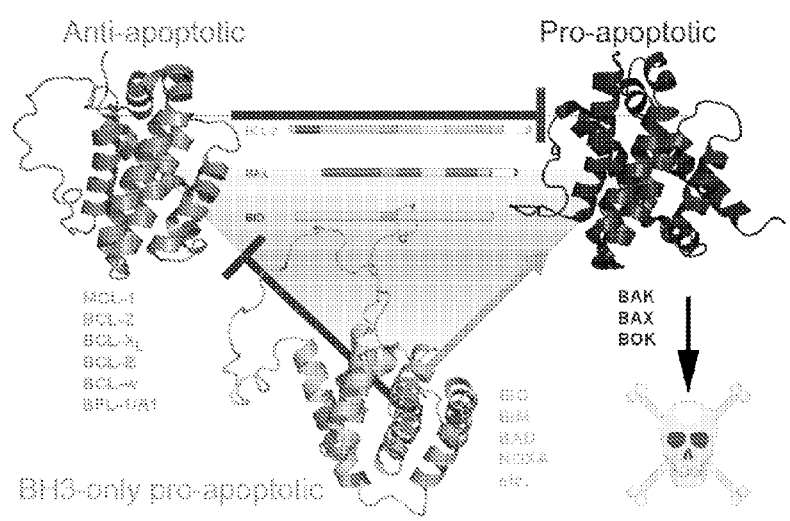
B
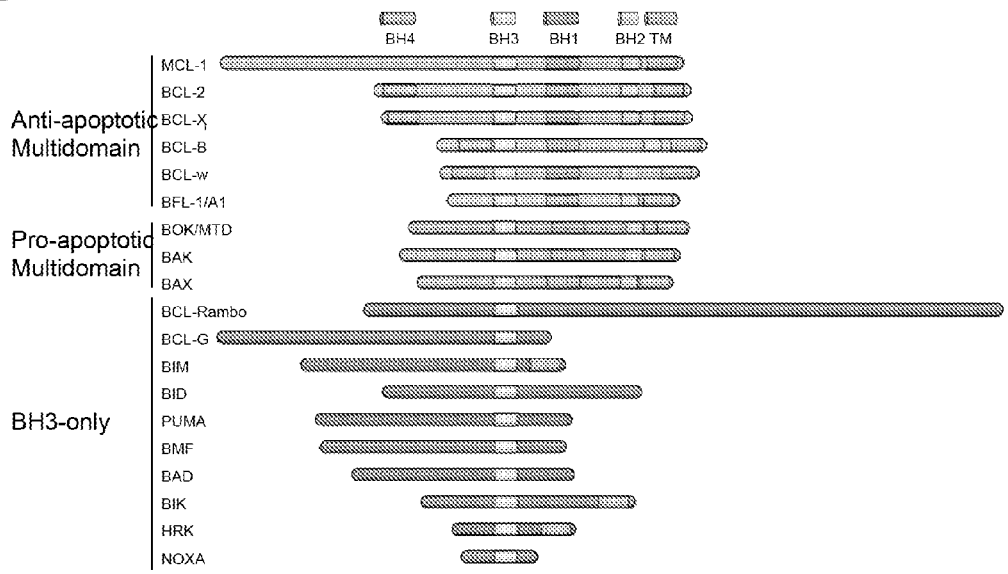

FIGURE 4

SEQ ID NO:1

```
1    MFGLKRNAVIGLNLYCGGAGLGAGSGGATRPGGRLLATEKEASARREIGG  50
51   GEAGAVIGGSAGASPPSTLTPDSRRVARPPPIGAEVPDVTATPARLLFFA  100
101  PTRRAAPLEEMEAPAADAIMSPEEELDGYEPEPLGKRPAVLPLLELVGES  150
151  GNNTSTDGSLPSTPPPAEEEEDDLYRQSLEIISRYLREQATGAKDTKPMG  200
201  RSGATSRKALETLRRVGDGVQRNHETAFQGMLRKLDIKNEDDVKSLSRVM  250
251  IHVFSDGVTNWGRIVTLISFGAFVAKHLKTINQESCIEPLAESITDVLVR  300
301  TKRDWLVKQRGWDGFVEFFHVEDLEGGIRNVLLAFAGVAGVGAGLAYLIR  350
```

SEQ ID NO:72
```
1    MFGLKRNAVIGLNLYCGGAGLGAGSGGATRPGGRLLATEKEASARREIGG  50
51   GEAGAVIGGSAGASPPSTLTPDSRRVARPPPIGAEVPDVTATPARLLFFA  100
101  PTRRAAPLEEMEAPAADAIMSPEEELDGYEPEPLGKRPAVLPLLELVGES  150
151  GNNTSTDGSLPSTPPPAEEEEDDLYRQSLEIISRYLREQATGAKDTKPMG  200
201  RSGATSRKALETLRRVGDGVQRNHETAFQGWVCGVLPCRGPRRWHQECAA  250
251  GFCRCCWSRSWFGISNKIALL                               271
```

SEQ ID NO:73
```
                        DELYRQSLEIISRYLREQATGAKDTKPMG  200
201  RSGATSRKALETLRRVGDGVQRNHETAFQGMLRKLDIKNEDDVKSLSRVM  250
251  IHVFSDGVTNWGRIVTLISFGAFVAKHLKTINQESCIEPLAESITDVLVR  300
301  TKRDWLVKQRGWDGFVEFFHVEDLEGG
```

FIGURE 5

SEQ ID NO: 2

```
1    MPGKKARKNAQPSPARAPAELEVECATQLRRFGDKLNFRQKLLNLISKLF  50
51   CSGT                                                54
```

FIGURE 6

SEQ ID NO: 3

```
1    MEVLRRSSVFAAEIMDAFDRSPTDKELVAQAKALGREYVHARLLRAGLSW  50
51   SAPERAAPVPGRLAEVCAVLLRLGDELEMIRPSVYRNVARQLHISLQSEP  100
101  VVTDAFLAVAGHIFSAGITWGKVVSLYAVAAGLAVDCVRQAQPAMVHALV  150
151  DCLGEFVRKTLATWLRRGGWTDVLKCVVSTDPGLRSHWLVAALCSFGRF   200
201  LKAAFFVLLPER                                        212
```

FIGURE 7

BH3-only

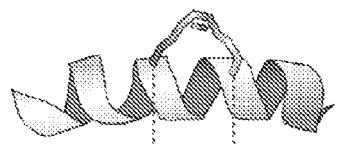

| | | |
|---|---|---|
| BIM SAHB$_A$ | IWIAQELRXIGDXFNAYYARR | SEQ ID NO: 4 |
| BID SAHB$_A$ | DIIRNIARHLAXVGDXBDRSIRR | SEQ ID NO: 5 |
| BAD SAHB$_A$ | NLWAAQRYGRELRXBSDXFVDSFKK | SEQ ID NO: 6 |
| NOXA SAHB$_A$ | LEVESATQLRXFGDXLNFRQKL | SEQ ID NO: 7 |
| PUMA SAHB$_A$ | QWAREIGAQLRXGADXLNAQY | SEQ ID NO: 8 |

Multidomain Pro-Apototic

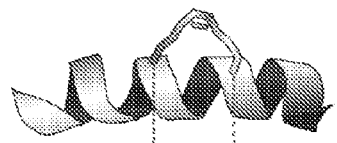

| | | |
|---|---|---|
| BAK SAHB$_A$ | QVGRQLAXIGDXINRRYD | SEQ ID NO: 9 |
| BAX SAHB$_A$ | ASTKKLSESLKXIGDXLDSN | SEQ ID NO: 10 |
| BOK SAHB$_A$ | RLAEVSAVLLXLGDXLEBIR | SEQ ID NO: 11 |

Multidomain Anti-Apoptotic

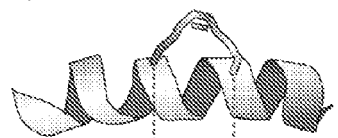

| | | |
|---|---|---|
| MCL-1 SAHB$_A$ | KALETLRXVGDXVQRNHETAF | SEQ ID NO: 12 |
| BCL-2 SAHB$_A$ | VVHLTLRXAGDXFSRRY | SEQ ID NO: 13 |
| BCL-X SAHB$_A$ | AVKQALRXAGDXFELRY | SEQ ID NO: 14 |
| BCL-W SAHB$_A$ | LHQABRXAGDXFETRF | SEQ ID NO: 15 |
| BFL-1/A1 SAHB$_A$ | KEVEKNLKXSLDXVNVSV | SEQ ID NO: 16 |

A

B

C

| | 208 228 | |
|---|---|---|
| MCL-1 BH3 | KALETLRRVGDGVQRNHETAF | SEQ ID NO: 17 |
| MCL-1 SAHB$_A$ | KALETLRXVGDXVQRNHETAF | SEQ ID NO: 18 |
| MCL-1 SAHB$_B$ | KALXTLRXVGDGVQRNHETAF | SEQ ID NO: 19 |
| MCL-1 SAHB$_C$ | KALETLRRVXDGVXRNHETAF | SEQ ID NO: 20 |
| MCL-1 SAHB$_D$ | KALETLRRVGDGVXRNHXTAF | SEQ ID NO: 21 |
| MCL-1 SAHB$_E$ | KALETLRRVGDGVQRXHETXF | SEQ ID NO: 22 |

FIGURE 23

| MCL-1 Non-Bindering SAHBs | | |
|---|---|---|
| BCL-W SAHB | LHQABRXAGDXFETRF | SEQ ID NO: 15 |
| BFL-1 SAHB | KEVEKNLKXSLDXVNVVSV | SEQ ID NO: 16 |
| BCL-XL SAHB | AVKQALRXAGDXFELRY | SEQ ID NO: 14 |
| BCL-2 SAHB | VVHLTLRXAGDXFSRRY | SEQ ID NO: 13 |
| BAD SAHB | NLWAAQRYGRELRXBSDXFVDSFKK | SEQ ID NO: 6 |

| MCL-1 Specific and Non-Specific SAHBs (Kd < 250 nM) | | |
|---|---|---|
| PUMA SAHB | QWAREIGAQLRXBADXLNAQY | SEQ ID NO: 8 |
| NOXA SAHB | LEVESXTQLXRFGDKLNFRQKL | SEQ ID NO: 7 |
| BIM SAHB | IWIAQELRXIGDXFNAYYARR | SEQ ID NO: 4 |
| BID SAHB | DIIRNIARHLAXVGDXBDRSI | SEQ ID NO: 5 |
| BIK SAHB | ALALRLAXIGDXBDVSLRA | SEQ ID NO: 23 |
| BOK SAHB | RLAEVSAVLLXLGDXLE | SEQ ID NO: 11 |
| BAX SAHB | ASTKKLSESLKXIGDXLDSN | SEQ ID NO: 10 |
| BAK SAHB | QVGRQLAXIGDXINRRYD | SEQ ID NO: 9 |
| BCL-B SAHB | EAAVLRXAAAXLRQIH | SEQ ID NO: 24 |
| MCL-1 SAHB | KALETLRXVGDXVQRNHE | SEQ ID NO: 12 |

| MCL-1 Based Peptides | | |
|---|---|---|
| *MCL-1 Staple Position Varients* | | |
| MCL-1 BH3 | KALETLRRVGDGVQRNHETAF | SEQ ID NO: 17 |
| MCL-1 SAHB A | KALETLRXVGDXVQRNHETAF | SEQ ID NO: 18 |
| MCL-1 SAHB B | KALXTLRXVGDGVQRNHETAF | SEQ ID NO: 19 |
| MCL-1 SAHB C | KALETLRRVXDGVXRNHETAF | SEQ ID NO: 20 |
| MCL-1 SAHB D | KALETLRRVGDGVXRNHXTAF | SEQ ID NO: 21 |
| MCL-1 SAHB E | KALETLRRVGDGVRXHETXF | SEQ ID NO: 22 |
| MCL-1 SAHB F | KXLETXRRVGDGVQRNHETAF | SEQ ID NO: 25 |
| *Cell Permeability Varients* | | |
| MCL-1 SAHB B_R | RKALXTLRXVGDGVQRNHETAF | SEQ ID NO: 26 |
| MCL-1 SAHB D_R | RKALETLRRVGDGVXRNHXTAF | SEQ ID NO: 27 |
| MCL-1 SAHB F_R | RKXLETXRRVGDGVQRNHETAF | SEQ ID NO: 28 |
| *Length Varients* | | |
| MCL-1 BH3_1 | KALETLRRVGDGVQRNHE | SEQ ID NO: 29 |
| MCL-1 SAHB A_1 | KALETLRXVGDXVQRNHE | SEQ ID NO: 30 |
| MCL-1 SAHB A_2 | LRXVGDXVQ | SEQ ID NO: 31 |
| MCL-1 SAHB A_3 | LRXVGDXV | SEQ ID NO: 32 |
| MCL-1 SAHB A_4 | FRXVGDXV | SEQ ID NO: 33 |

FIGURE 23 (continued)

| Protein Crosslinking Varients | | |
|---|---|---|
| MCL-1Staple6 BPA (U) | RKALETLRRVGDGVXRNUXTAF | SEQ ID NO: 34 |
| Single and Combination Point Mutant Varients | | |
| MCL-1 SAHB A_K208A | AALETLRXVGDXVQRNHETAF | SEQ ID NO: 35 |
| MCL-1 SAHB A_A209E | KELETLRXVGDXVQRNHETAF | SEQ ID NO: 36 |
| MCL-1 SAHB A_L210A | KAAETLRXVGDXVQRNHETAF | SEQ ID NO: 37 |
| MCL-1 SAHB A_E211A | KALATLRXVGDXVQRNHETAF | SEQ ID NO: 38 |
| MCL-1 SAHB A_T212A | KALEALRXVGDXVQRNHETAF | SEQ ID NO: 39 |
| MCL-1 SAHB A_L213A | KALETARXVGDXVQRNHETAF | SEQ ID NO: 40 |
| MCL-1 SAHB A_R214A | KALETLAXVGDXVQRNHETAF | SEQ ID NO: 41 |
| MCL-1 SAHB A_V216A | KALETLRXAGDXVQRNHETAF | SEQ ID NO: 42 |
| MCL-1 SAHB A_G217A | KALETLRXVADXVQRNHETAF | SEQ ID NO: 43 |
| MCL-1 SAHB A_G217E | KALETLRXVEDXVQRNHETAF | SEQ ID NO: 44 |
| MCL-1 SAHB A_D218A | KALETLRXVGAXVQRNHETAF | SEQ ID NO: 45 |
| MCL-1 SAHB A_V220A | KALETLRXVGDXAQRNHETAF | SEQ ID NO: 46 |
| MCL-1 SAHB A_V220F | KALETLRXVGDXFQRNHETAF | SEQ ID NO: 47 |
| MCL-1 SAHB A_Q221A | KALETLRXVGDXVARNHETAF | SEQ ID NO: 48 |
| MCL-1 SAHB A_R222A | KALETLRXVGDXVQANHETAF | SEQ ID NO: 49 |
| MCL-1 SAHB A_N223A | KALETLRXVGDXVQRAHETAF | SEQ ID NO: 50 |
| MCL-1 SAHB A_H224A | KALETLRXVGDXVQRNAETAF | SEQ ID NO: 51 |
| MCL-1 SAHB A_E225A | KALETLRXVGDXVQRNHATAF | SEQ ID NO: 52 |
| MCL-1 SAHB A_T226A | KALETLRXVGDXVQRNHEAAF | SEQ ID NO: 53 |
| MCL-1 SAHB A_A227E | KALETLRXVGDXVQRNHETEF | SEQ ID NO: 54 |
| MCL-1 SAHB A_F228A | KALETLRXVGDXVQRNHETAA | SEQ ID NO: 55 |
| MLC-1 SAHB A_L210A,V220F | KAAETLRXVGDXFQRNHETAF | SEQ ID NO: 56 |
| MCL-1 SAHB D_L210A | KAAETLRRVGDGVXRNHXTAF | SEQ ID NO: 57 |
| MCL-1 SAHB D_L210A, V220F | KAAETLRRVGDGFXRNHXTAF | SEQ ID NO: 58 |
| Other | | |
| MCL-1 Invert1 | FATEHNRQVXDGVXRLTELAK | SEQ ID NO: 59 |
| MCL-1 Invert2 | FATEHNRXVGDXVRRLTELAK | SEQ ID NO: 60 |

FIGURE 23 (continued)

| BIM Based Peptides | | |
|---|---|---|
| BIM SAHB D_I65F, E68K | IWIXQELXRFGDKFNAYYAR | SEQ ID NO: 61 |
| BIM SAHB A_L62A,F69A | IWIAQEARXIGDXANAYYARR | SEQ ID NO: 62 |

| NOXA Based Peptides | | |
|---|---|---|
| NOXA SAHB A | LEVESATQLRXFGDXLNFRQKL | SEQ ID NO: 63 |
| NOXA SAHB B | LEVESXTQLRXFGDKLNFRQKL | SEQ ID NO: 64 |
| NOXA SAHB B_1 | LEVESXTQLXRFGDKLNF | SEQ ID NO: 65 |
| NOXA SAHB C | LEVXSATXLRRFGDKLNFRQKL | SEQ ID NO: 66 |
| NOXA SAHB D | LEVESATQLRRFGDKLXFRQXL | SEQ ID NO: 67 |
| NOXA SAHB E | LEVEXATQXRRFGDKLNFRQKL | SEQ ID NO: 68 |

| BAK Based Peptides | | |
|---|---|---|
| BAK Specific | QVXRQLXRFGDKINRRYD | SEQ ID NO: 69 |

| MULE Based Peptides | | |
|---|---|---|
| MULE | VGQLLQXMGDXVYQQYRSLTR | SEQ ID NO: 70 |

In general the N-terminus of peptide (R) is derivatized as follows:
    Ac - bAla - R
    FITC - bAla - R In some cases the N-terminus of peptide (R) is derivatized as follows:
    Ac - R
    Ac - Peg - R
    Biotin - bAla - R
    Biotin - Peg - R

METHODS AND COMPOSITIONS FOR SPECIFIC MODULATION OF MCL-1

CROSS REFERENCE TO RELATED APPLICATIONS

This application is a 35 U.S.C. §371 U.S. national entry of International Application PCT/US2009/067363 (WO 2010/068684) having an International filing date of Dec. 9, 2009 which claims priority to U.S. Provisional Patent Application Ser. No. 61/120,988 filed Dec. 9, 2008 which are incorporated herein in their entirety.

GOVERNMENT SUPPORT

This invention was made with government support under N.I.H. grant 5PO1 CA92625-06. The U.S. Government has certain rights in the invention.

SEQUENCE LISTING

The instant application contains a Sequence Listing which has been submitted in ASCII format via EFS-Web, and is hereby incorporated by reference in its entirety. Said ASCII copy, created on Feb. 29, 2012, is named 82454US.txt and is 47,497 bytes in size.

BACKGROUND OF THE INVENTION

The discovery of BCL-2 over twenty years ago revealed a new paradigm in cancer biology, namely that the development and persistence of cancer can be driven by molecular roadblocks along the natural pathway to cell death (Bakhshi et al., 1985; Cleary and Sklar, 1985; Tsujimoto et al., 1985). The subsequent identification of an expansive family of BCL-2 proteins provoked an intensive investigation of the interplay among these critical regulators of cell death. What emerged was a network of guardians and executioners, each participating in a molecular choreography that dictates cell fate (Danial and Korsmeyer, 2004). Ten years into the BCL-2 era, structural studies defined how an anti-apoptotic BCL-2 family protein binds and sequesters a pro-apoptotic protein by trapping its α-helical BH3 domain in a hydrophobic groove on the anti-apoptotic protein surface (Sattler et al., 1997). Because reactivating apoptosis in cancer is a desirable therapeutic goal, molecular targeting of BCL-2 family grooves has become a pharmacological quest. Small molecules and peptides that effectively target BCL-2 family members are beginning to demonstrate that clearing the roadblock to cell death may yield a medical breakthrough for cancer patients (Oltersdorf et al., 2005; Perez-Galan et al., 2007; Walensky et al., 2004).

MCL-1 functions at the mitochondrial outermembrane, where it neutralizes pro-apoptotic proteins such as NOXA, PUMA, BIM, and BAK. MCL-1 overexpression has been linked to the pathogenesis of multiple myeloma (Derenne et al., 2002; Zhang et al., 2002), chemoresistance in acute myeloid leukemia cells (Konopleva et al., 2006), and high tumor grade and poor prognosis in breast cancer (Ding et al., 2007). Indeed, sensitivity of cancer cells to ABT-737 inversely correlates with cellular levels of MCL-1 (van Delft et al., 2006); and siRNA-induced decreases in MCL-1 levels have been shown to resensitize cancer cells to ABT-737 (Konopleva et al., 2006). The development of specific inhibitors for the diversity of anti-apoptotic proteins remains a formidable challenge due to the diversity of their BH3-binding pockets. However, identification of such compounds would provide finely-tuned therapies to treat specific diseases and avoid potential toxicities of broader targeting. In addition, such compounds would serve as invaluable research tools to probe the biological functions of individual BCL-2 family protein interactions. Although there is a clear therapeutic rationale for targeting MCL-1, to date, a selective small molecule MCL-1 inhibitor has remained out of reach.

BRIEF SUMMARY OF THE INVENTION

The present invention, at least in part, provides a series of stapled BCL-2 family peptide helices that have been identified herein as targeting the survival protein MCL-1 with high affinity and unprecedented selectivity. Specifically, the MCL-1 inhibitor SAHBs described herein target the canonical BH3 groove of MCL-1, displacing the MCL-1/BAK interaction, and sensitizing MCL-1 dependent cancer cells to mitochondrial apoptosis. Compositions and kits comprising such compounds, and uses of such compounds, including, e.g., therapeutic, research and screening uses of such compounds, are described.

The invention provides peptides that bind specifically to MCL-1 with at least a 2-fold, 5-fold, 10-fold, 15-fold, or 20-fold greater affinity than to MCL-1 than any other member of the human BCL-2 family wherein the peptide is a stabilized α-helix with non-natural amino acids joined by one or more (e.g., 1, 2, 3, 4) staples. Such peptides can be referred to as MCL-1 specific binders. The ends of the one or more staples are located between relative positions i and i+3, i and i+4, or i and i+7 derived from a polypeptide sequence selected from the group consisting of an MCL-1 stabilized alpha-helix of BCL-2 family BH3 domain (SAHB) peptide, a NOXA SAHB polypeptide, a BOK SAHB peptide, a tailored BIM SAHB peptide, a BAK SAHB peptide, and a MULE SAHB peptide.

In certain embodiments, the peptides include a sequence at least 80% identical to the sequence of LRXVGDXV (SEQ ID NO: 32), wherein X is any amino acid. The peptides can include a sequence at least 70%, 80%, or 90% identical to at least 8, 9, 10, 11, 12, 13, 14, 15, 16, 17, 18, 19, or 20 contiguous amino acids of the sequence RKALETLRRVGDGVQRNHETAF (SEQ ID NO: 93). In certain embodiments, the substitutions are conservative substitutions. In certain embodiments, the substitutions are non-conservative substitutions. In certain embodiments, the substitutions are a mixture of conservative and non-conservative substitutions. The substitutions can include natural and non-natural amino acids, including staples. In certain embodiments, the peptide sequences include RKALETLRRVGDGVXRNHXTAF (SEQ ID NO: 27), RKXLETXRRVGDGVQRNHETAF (SEQ ID NO: 28), RKALETLRXVGDXVQRNHETAF (SEQ ID NO: 74), RKALXTLRXVGDGVQRNHETAF (SEQ ID NO: 26), RKALETLRRVGDGVQRXHETXF (SEQ ID NO: 75), KALETLRRVGDGVXRNHXTAF (SEQ ID NO: 21), KXLETXRRVGDGVQRNHETAF (SEQ ID NO: 25), KALETLRXVGDXVQRNHETAF (SEQ ID NO: 74), KALXTLRXVGDGVQRNHETAF (SEQ ID NO: 19), and KALETLRRVGDGVQRXHETXF (SEQ ID NO: 22) wherein the X's are any amino acid, and in certain embodiments, wherein at least one X is a staple position.

The invention provides peptides that include a sequence at least 60% identical, 70% identical, or 80% identical to the sequence LRRFGDKL (SEQ ID NO: 76). In certain embodiments, the peptide is at least 70%, 80%, 90% identical to at least The peptides can include a sequence at least 70%, 80%, or 90% identical to at least 8, 9, 10, 11, 12, 13, 14, 15, 16, 17, 18, 19, or 20 contiguous amino acids of the sequence LEVESATQLRRFGDKLNFRQKL (SEQ ID NO: 77). The substitutions can be conservative or non-conservative substitutions or a mixture thereof. In certain embodiments, the a polypeptide include a sequence LEVESATQLRXFGDXLNFRQKL (SEQ ID NO: 63); LEVXSATXLRRFGDKLNFRQKL (SEQ ID NO: 66); LEVEXATQXRRFGDKLNFRQKL (SEQ ID NO: 68); LEVESXTQLXRFGDKLNFRQKL (SEQ ID NO: 7); LEVESXTQLXRFGDKLNF (SEQ ID NO: 65); LEVESATQLRRFGDKLXFRQXL (SEQ ID NO: 67), wherein the X's are any amino acid, and in certain embodiments, wherein at least one X is a staple position.

The invention provides peptides that include a sequence LLXLGDXL (SEQ ID NO: 78); LXRFGDKF (SEQ ID NO: 79); LXRFGDKI (SEQ ID NO: 80); and LQXMGDXY (SEQ ID NO: 81), wherein the X's are any amino acid, and in certain embodiments, wherein at least one X is a staple position.

The invention provides peptides that include a sequence 70%, 80%, or 90% identical to a sequence RLAEVSAVLLX-LGDXLE (SEQ ID NO: 82); IWIXQELXRFGDKFNAY-YAR (SEQ ID NO: 61); IWIXQELXRFGDKFNAYYAR (SEQ ID NO: 83); QVXRQLXRFGDKINRRYD (SEQ ID NO: 69); and VGQLLQXMGDXYQQYRSLTR (SEQ ID NO: 84), wherein the X's are any amino acid, and in certain embodiments, wherein at least one X is a staple position.

The invention provides peptides of essentially any length, but preferably 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids in length.

The peptides provided by the invention have an affinity for MCL-1 of at least 50 µM, at least 40 µM, at least 30 µM, at least 20 µM, at least 10 µM, at least 1 µM, at least 100 nM, at least 50 nM, at least 25 nM, at least 10 nM.

The invention provides a peptide that binds specifically to MCL-1, particularly to a BH3 domain of a human MCL-1. In certain embodiments, the peptide binds to MCL-1 with at least a 2-fold, 5-fold, 10-fold, 15-fold, or 20-fold greater affinity than to any other member of the human BCL-1 family. In certain embodiments, the human BCL-1 family is understood to include the human version of BIM, BID, BAD, NOXA, PUMA, BAK, BAX, BOK, BCL-2, BCL-XL, BCL-W, and BFL-1/A1. In certain embodiments, the human BCL-1 family is understood to include the human version of BCL-2, BCL-XL, BCL-W, and BFL-1/A1. In certain embodiments, the peptide comprises the sequence of XXLX-TLRXVGDXVXRXHXTXX (SEQ ID NO: 85), wherein a pair two X's three amino acids apart are joined by a staple, and wherein the remaining X's are any amino acid. In certain embodiments, the peptide comprises the sequence of XXLX-TLRXVGDXVXRXHXTXX (SEQ ID NO: 85), wherein a pair two X's three amino acids apart are joined by a staple, and wherein the remaining X's can include conservative amino acid substitution from the sequence KALETLR-RVGDGVQRNHETAF (SEQ ID NO: 17). In certain embodiments, the peptide comprises the sequence of KALETLRX-VGDXVQRNHETAF (SEQ ID NO: 18) wherein the X's are joined by a staple. In certain embodiments, the peptide comprises the sequence of KALXTLRXVGDGVQRNHETAF (SEQ ID NO: 19) wherein the X's are joined by a staple. In certain embodiments, the peptide comprises the sequence of KALETLRRVGDGVXRNHXTAF (SEQ ID NO: 21) wherein the X's are joined by a staple. In certain embodiments, the peptide comprises the sequence of KALETLR-RVGDGVQRXHETXF (SEQ ID NO: 22) wherein the X's are joined by a staple.

In an aspect, the instant invention provides a method for treating or preventing a disease or disorder in a subject via administration of an effective amount of a selective MCL-1 inhibitor and a pharmaceutically acceptable carrier to a subject. In one embodiment, the MCL-1 inhibitor includes a BH3 domain polypeptide, optionally a stapled BH3 domain polypeptide. In another embodiment, the selective MCL-1 inhibitor includes one or more of the following polypeptides: a NOXA stabilized alpha-helix of BCL-2 family BH3 domain (SAHB) polypeptide, a BOK SAHB peptide, an MCL-1 SAHB peptide, a wild type or tailored BIM SAHB or BAK SAHB peptide, or a Mule SAHB peptide. In one embodiment, the NOXA SAHB peptide includes SEQ ID NO: 7 or 63-68, or a derivative thereof. In another embodiment, the BOK SAHB peptide includes SEQ ID NO: 11 or a derivative thereof. In an additional embodiment, the MCL-1 SAHB peptide includes SEQ ID NO: 12 or 17-60, or a derivative thereof. In a further embodiment, the BIM SAHB peptide includes SEQ ID NO: 61 or 62, or a derivative thereof. In another embodiment, the BAK SAHB peptide includes SEQ ID NO: 69, or a derivative thereof. In an additional embodiment, the Mule SAHB peptide comprises SEQ ID NO: 70 or a derivative thereof. In one embodiment, the sequence of said SAHB peptide is a chimeric sequence that includes sequence(s) selected from the group consisting of NOXA, BOK, BIM, BAK, and Mule SAHB polypeptide sequences.

In an embodiment, the method further includes administering an effective amount of a BCL-2 inhibitor to the subject. Optionally, the BCL-2 inhibitor is a selective BCL-2 inhibitor. In one embodiment, the BCL-2 inhibitor is N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide ("ABT-263") or N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide ("ABT-737").

In an embodiment, the disease or disorder is a hyperproliferative disorder, an inflammatory disease or disorder, an infectious disease or disorder, a cell cycle regulation disease or disorder, an autophagy regulation disease or disorder, or an autoimmune disease or disorder. Optionally, the hyperproliferative disease or disorder is a lymphoma, leukemia, carcinoma (e.g. hepatic, breast, lung), multiple myeloma, or a sarcoma. In one embodiment, the leukemia is AML or ALL. In a related embodiment, the hyperproliferative disorder is a resistant hyperproliferative disorder; optionally, one that is resistant to a BCL-2 inhibitor. In another embodiment, the hyperproliferative disorder is a relapsed or refractory cancer.

In an embodiment, the method further comprises administering an effective amount of a chemotherapeutic to the subject. Optionally, the chemotherapeutic agent is an alkylating agent (e.g., carboplatin), an anti-metabolite (e.g., methotrexate), an anthracycline (e.g., doxorubicin), a plant alkaloid (e.g., vincristine), an antibody (e.g., rituxan), a steroid (e.g., dexamethasone), a targeted therapy (e.g., TRAIL, bortezamib, ABT-263), or another cytotoxic or cytostatic agent.

In an embodiment, the cell cycle regulation disease or disorder is a cancer, autoimmune disease or lymphoproliferative disease. Optionally, the cell cycle regulation disease or disorder is resistant to cytostatic or cytotoxic therapy.

In an aspect, the invention provides a method for regulating MCL-1 activity in a cell by contacting the cell with a polypeptide comprising a stapled BH3 domain. In one embodiment, MCL-1 activity is inhibited. In another embodiment, the polypeptide is a selective MCL-1 inhibitor. In an additional embodiment, apoptosis is enhanced in the cell.

In an aspect, the invention provides a method for treating a refractory cancer in a subject via administration of an effective amount of a selective MCL-1 inhibitor and a pharmaceutically acceptable carrier to a subject. In one embodiment, the refractory cancer is resistant to administration of a chemotherapeutic, or to administration of a BCL-2 inhibitor. Optionally, the refractory cancer is resistant to administration of N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, resistant to administration of N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, resistant to administration of gossypol, or to administration of obatoclax. In an additional embodiment, the refractory cancer overexpresses MCL-1. In a further embodiment, the selective MCL-1 inhibitor includes a polypeptide possessing a stapled BH3 domain. In another embodiment, the selective MCL-1 inhibitor includes a polypeptide that is a NOXA stabilized alpha-helix of BCL-2 BH3 domain (SAHB) polypeptide, a BOK SAHB polypeptide, an MCL-1 SAHB domain polypeptide, a tailored BIM SAHB polypeptide, a tailored BAK SAHB polypeptide, or a Mule SAHB polypeptide.

In an aspect, the invention provides a method for treating a cancer in a subject involving administering an effective amount of a selective MCL-1 inhibitor and a pharmaceutically acceptable carrier to a subject, where the cancer is resistant to administration of N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide ("ABT-737") or to administration of N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide ("ABT-263"); optionally, the cancer also overexpresses MCL-1.

In an aspect, the invention provides a method for enhancing the apoptotic response of a cell to a non-MCL-1 selective BCL-2 family polypeptide inhibitor by contacting a selective MCL-1 inhibitor with the cell. In one embodiment, the non-MCL-1 selective BCL-2 family polypeptide inhibitor is a selective BCL-2 inhibitor. In another embodiment, the non-MCL-1 selective BCL-2 family polypeptide inhibitor is N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide ("ABT-263"); N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide ("ABT-737"); gossypol; or obatoclax.

In an aspect, the invention provides a method for enhancing autophagic cell death in a cell, or for inhibiting multimerization of MCL-1 in a cell, by contacting the cell with a selective MCL-1 inhibitor.

In an aspect, the invention provides a method for inducing multimerization of MCL-1 in a cell by contacting the cell with a selective MCL-1 activator.

In an aspect, the invention provides a method for inhibiting the interaction of MCL-1 with pro-apoptotic BAX or BAK polypeptide(s) in a cell by contacting the cell with an effective amount of a selective MCL-1 inhibitor, either to inhibit MCL-1 binding to BAX or BAK, or to displace BAX or BAK from MCL-1.

In an aspect, the invention provides a method for identifying a compound that modulates the activity of an MCL-1 polypeptide involving contacting an MCL-1 polypeptide with a test compound under conditions suitable for interaction of the test compound with the MCL-1 polypeptide; and detecting modulation of an activity of the MCL-1 polypeptide, where detection of such modulation identifies an MCL-1 modulatory compound. In one embodiment, the test compound is a small molecule or a polypeptide. Optionally, the polypeptide has a stapled BH3 domain. In one embodiment, the sequence of the polypeptide is at least 80% identical to an SAHB sequence listed in FIG. 13. In another embodiment, the invention provides an MCL-1 modulatory compound or selective MCL-1 binding agent identified by a method of the invention.

In an aspect, the invention provides a method for identifying a selective MCL-1 binding agent by contacting an MCL-1 polypeptide bound to an MCL-1 SAHB with a test compound under conditions suitable for interaction of the test compound with the MCL-1 polypeptide; and detecting dissociation of the MCL-1 SAHB from the MCL-1 polypeptide, where detection of such dissociation identifies a test compound as a selective MCL-1 binding agent. In one embodiment, the test compound is a small molecule or a polypeptide. In another embodiment, the MCL-1 binding agent is an MCL-1 inhibitor. In a further embodiment, the MCL-1 polypeptide, or, optionally, the MCL-1 SAHB, is labeled. In one embodiment, the label is FITC.

In an aspect, the invention provides a pharmaceutical composition that includes a selective MCL-1 inhibitor. In one embodiment, the selective MCL-1 inhibitor includes a polypeptide sequence that is at least 95% identical to a NOXA stabilized alpha-helix of BCL-2 family BH3 domain (SAHB) polypeptide sequence, a BOK SAHB peptide sequence, an MCL-1 SAHB peptide sequence, a wild type or tailored BIM SAHB or BAK SAHB peptide sequence or a Mule SAHB peptide sequence. In another embodiment, the selective MCL-1 inhibitor includes a polypeptide that is a NOXA stabilized alpha-helix of BCL-2 family BH3 domain (SAHB) polypeptide, a BOK SAHB peptide, an MCL-1 SAHB peptide, a wild type or tailored BIM SAHB or BAK SAHB peptide or a Mule SAHB peptide. In one embodiment, the MCL-1 SAHB polypeptide includes SEQ ID NO: 16 or a derivative thereof. In another embodiment, the BIM SAHB polypeptide includes SEQ ID NO: 31, 32 or a derivative thereof. In an additional embodiment, the BAK SAHB domain polypeptide includes SEQ ID NO: 40.

BRIEF DESCRIPTION OF THE DRAWINGS

FIG. 1 (A) illustrates how the three subgroups of BCL-2 family members interact with one another to form a signaling network that regulates apoptosis. (B) depicts an alignment of BCL-2 family members, highlighting the conserved BCL-2 homology domains shared among the protein subgroups.

FIG. 4 shows the primary amino acid sequence of humans MCL-1 long (SEQ ID NO: 1) and the alternatively spliced MCL-1 short. The BH3 regions are underlined and the alternative C-terminus of MCL-1 short is in italics. A small nuclear MCL-1, believed to be a cleavage product of MCL-1 long has also been reported (SEQ ID NO: 72). Finally, MCL-1NC protein used for expression and binding studies is shown (SEQ ID NO: 73).

FIG. 5 shows the primary amino acid sequence of human NOXA. The BH3 region is underlined.

FIG. 6 shows the primary amino acid sequence of human BOK. The BH3 region is underlined.

FIG. 7 shows a panel of stabilized alpha-helices of BCL-2 domains (SAHBs) designed based on the BH3 domains of pro- and anti-apoptotic BCL-2 family members. A pair of crosslinking non-natural amino acids (X) were substituted at i, i+4 position of the non-interacting helical surface and "stapled" by ruthenium-catalyzed olefin metathesis. To optimize the activity of Grubbs' ruthenium catalyst, sulfur-containing methionines were replaced with norleucines, which are designated by the letter B.

Figure 8:
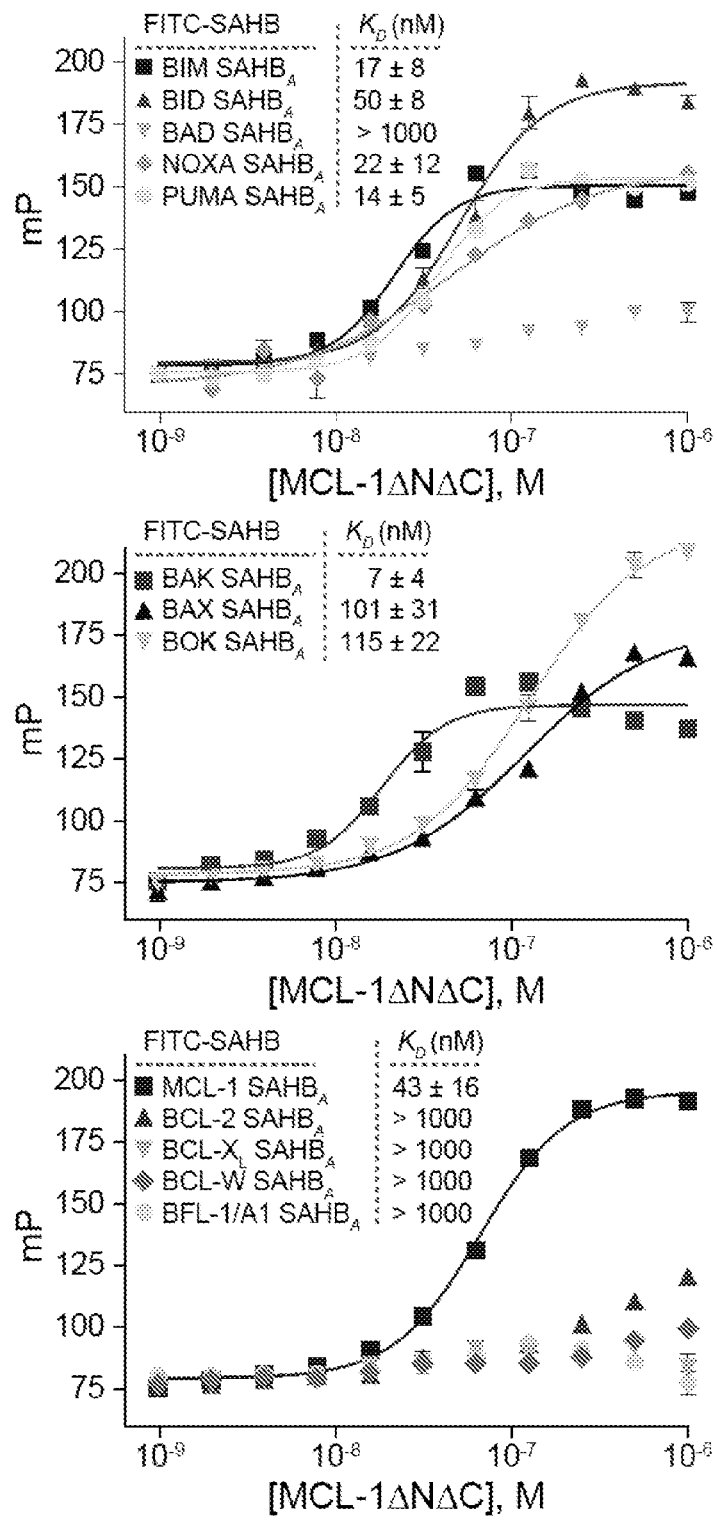

FIG. 8 shows graphs for determining dissociation constants for the binding of fluorescently labeled SAHBs to MCL-1ΔNΔC by fluorescence polarization assay (FPA) and nonlinear regression analysis. (A-D) illustrate fluorescence polarization assays that FITC-derivatized SAHBs and recombinant MCL-1 protein, and distinguished MCL-1 targeting SAHBs from non-binders. (E) demonstrates the binding isotherms of a subset of high affinity MCL-1 binders, including MCL-1 SAHB and NOXA SAHB, which were selective for MCL-1 and did not engage BCL-XL, BCL-w, or BFL1/A1. BOK SAHB displayed a significant preference for MCL-1 over the other anti-apoptotics.

Figure 9:
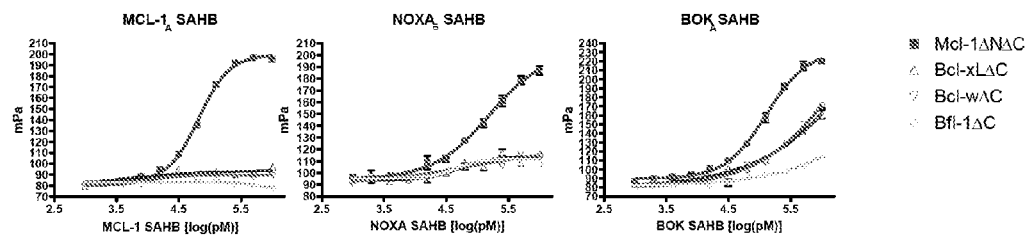

FIG. 9 shows fluorescence polarization assays using FITC-derivatized SAHBs and recombinant anti-apoptotic proteins revealed high affinity MCL-1 targeting compounds (A), with a subset exhibiting selective MCL-1 interaction (A, B). (A) illustrates a table of $K_D$ values for MCL-1-specific and pan-anti-apoptotic binding SAHBs. (B) demonstrates the binding isotherms of a subset of high affinity MCL-1 binders, including MCL-1 SAHB and NOXA SAHB, which were selective for MCL-1 and did not engage BCL-$X_L$, BCL-w, or BFL1/A1. BOK SAHB displayed a significant preference for MCL-1 over the other anti-apoptotics.

Figure 10:
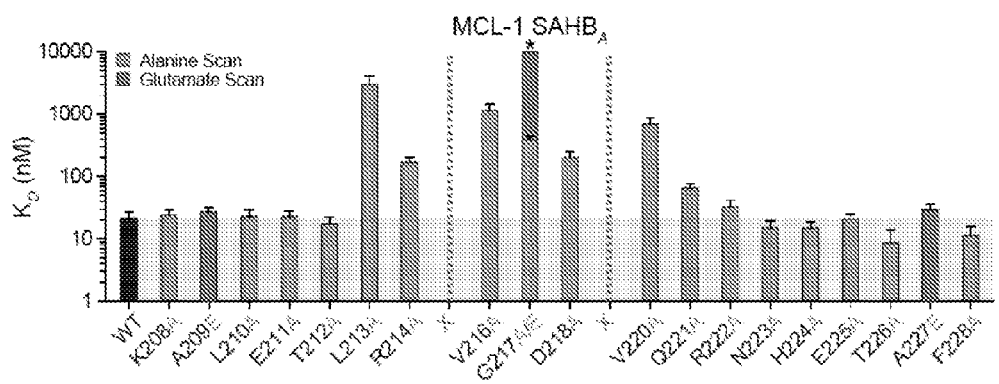

FIG. 10 illustrates the specificity determinants of the MCL-1 BH3 helix for MCL-1. A panel of sequential alanine mutants (alanine scan) of FITC-MCL-1 SAHB was generated for FPA binding analysis, revealing key residues within the core BH3 sequence required for high affinity MCL-1ΔNΔC binding. Glutamate mutagenesis was also performed to evaluate the contribution of native alanine and glycine residues to MCL-1ΔNΔC binding.

Figure 11:
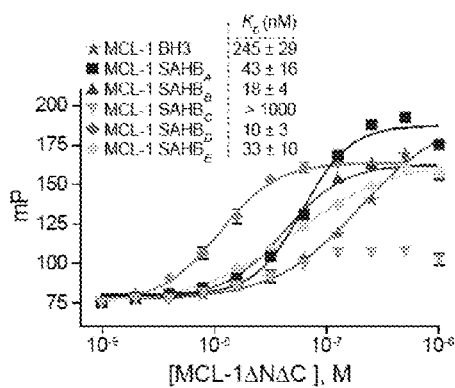

FIG. 11 Shows sampling of a variety of staple positions along the helical surface revealed disruption of MCL-1ΔNΔC binding only by the G217-Q221 staple (MCL-1 SAHBC), which is located at the hydrophobic binding interface. MCL-1 SAHBD exhibited the strongest binding activity (KD, 10 nM), with 4-fold improvement over the parental MCL-1 SAHBA. (A) illustrates a "staple scan" of the MCL-1 SAHB, demonstrating differential placement of the hydrocarbon staple along the length of the MCL-1 BH3 sequence; (B) Sampling a variety of staple positions along the helical surface revealed disruption of MCL-1ΔNΔC binding only by the G217-Q221 staple (MCL-1 SAHB$_C$), which is located at the hydrophobic binding interface. MCL-1 SAHB$_D$ exhibited the strongest binding activity ($K_D$, 10 nM), with 4-fold improvement over the parental MCL-1 SAHB$_A$.

Figure 12:
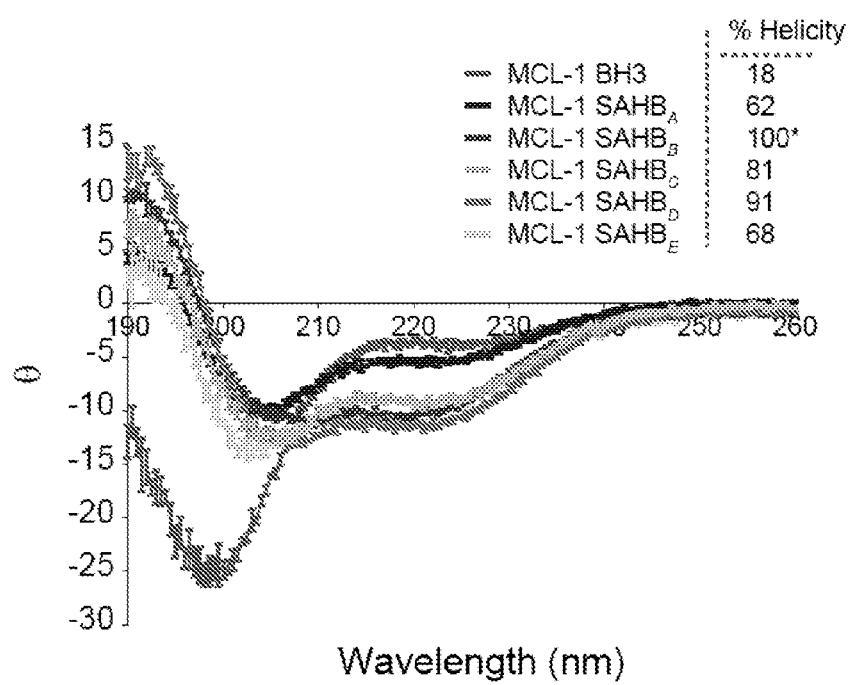

FIG. 12 shows that circular dichroism revealed marked enhancement of α-helical structure for MCL-1 SAHBs compared to the corresponding unmodified peptide. Hydrocarbon stapling converts the predominantly non-helical MCL-1 BH3 template peptide into a stabilized α-helical structure, with differentially stapled SAHBs exhibiting percent helical content ranging from 55-100%.

Figure 13:
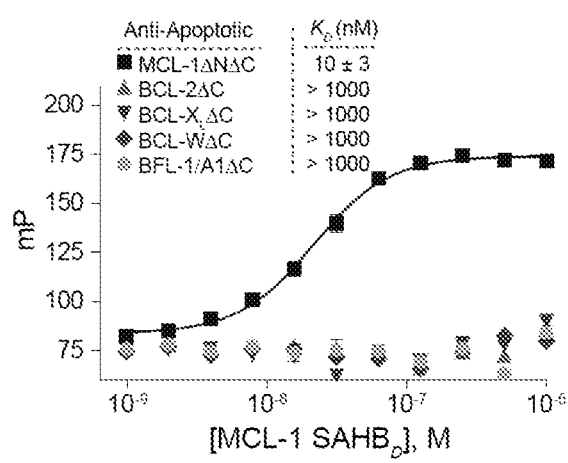

FIG. 13 shows that like FITC-MCL-1 SAHBA, FITC-MCL-1 SAHB$_D$ display a potent and exclusive interaction with MCL-1ΔNΔC, as evidenced by FPA performed against a broad panel of anti-apoptotic targets. that like FITC-MCL-1 SAHB$_A$, FITC-MCL-1 SAHB$_D$ displayed a potent and exclusive interaction with MCL-1ΔNΔC, as evidenced by FPA performed against a broad panel of anti-apoptotic targets.

Figure 14:
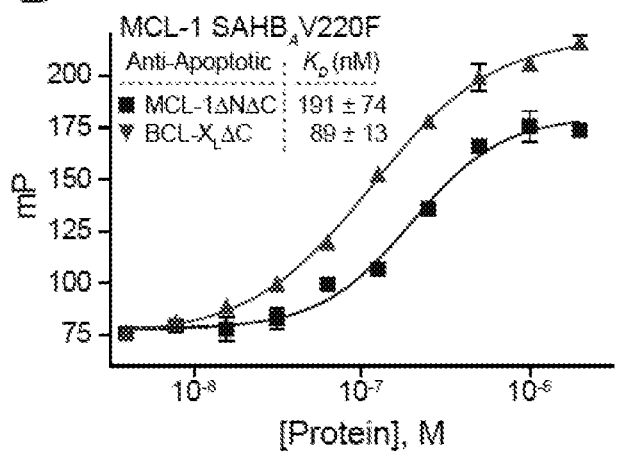

FIG. 14 (A) Sequence alignment (SEQ ID NOS 87-92, respectively, in order of appearance) of select BH3 domains revealed key differences in the hydrophobic residues that engage the canonical BH3 pocket of anti-apoptotic proteins. MCL-1 BH3 contains a unique LXXVXXXV motif. Both the BCL-2/BCL-XL-selective BAD BH3 domain and the pan-anti-apoptotic binding BIM BH3 domain contain a Phe at the position corresponding to Val220 in MCL-1 BH3 (underlined). Interestingly, the murine NOXA BH3 and MULE BH3 (not shown) domains, which exhibit selectivity for MCL-1, both contain a Val in this position. (B) Site directed mutagenesis of MCL-1 SAHBA alters the specificity for MCL-1. MCL-1 SAHBA V220F binds to both MCL-1 and BCL-XL, demonstrates that V220 is a key specificity determinant for MCL-1 SAHBA binding to both MCL-1ΔNΔC and BCL-XLΔC as demonstrated by FPA.

Figure 15:
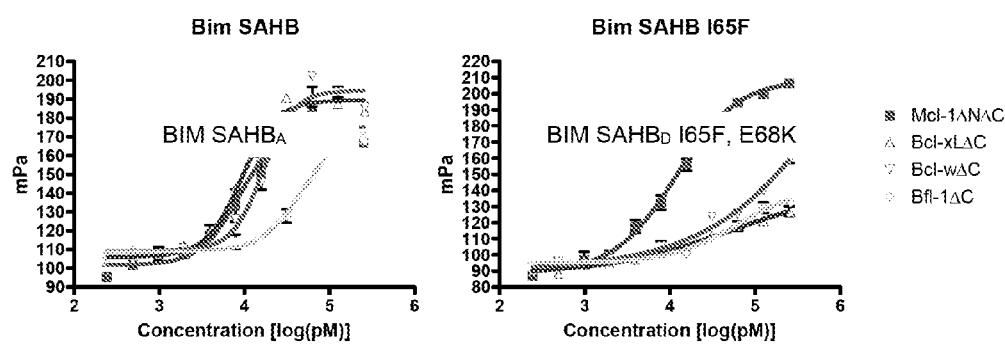

FIG. 15 shows that site-directed amino acid mutagenesis converted the pan-anti-apoptotic binder, BIM SAHB, into a selective MCL-1 binder. Specificity for MCL-1 can also be obtained by site directed mutagenesis of non-selective SAHBs. Mutagenesis of Ile65 and Glu68 to Phe and Lys, respectively, in BIM SAHBD, a staple variant of BIM SAHBA, resulted in selective inhibition of MCL-1 as determined by fluorescence polarization assay.

Figure 16:
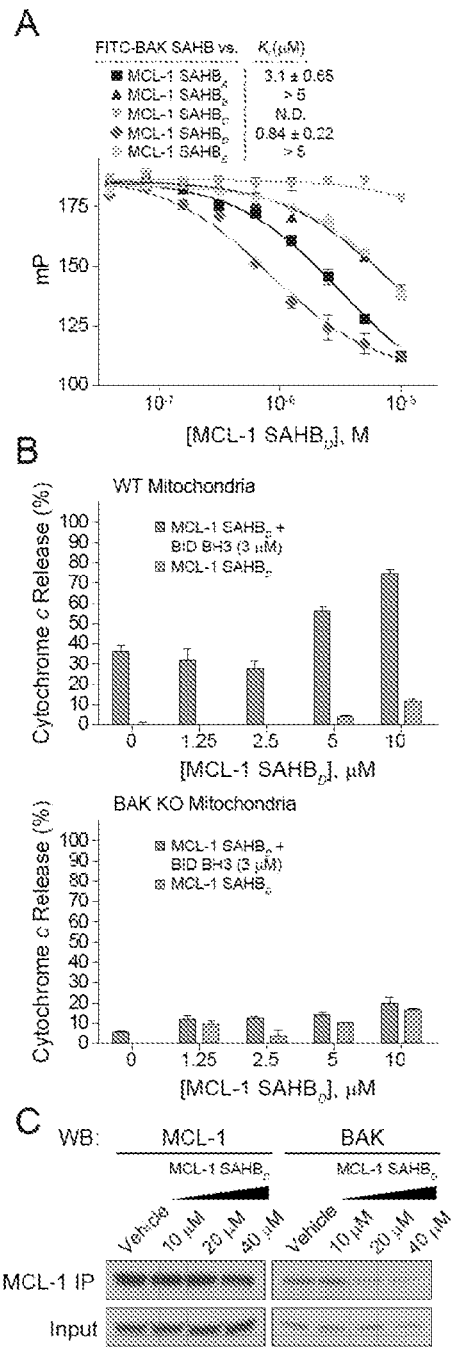

FIG. 16 shows (A) MCL-1 SAHBs effectively prevent sequestration of the BAK BH3 helix by MCL-1ΔNΔC, as demonstrated by competition FPA (FITC-BAK SAHB/MCL-1ΔNΔC IC50, 0.27+0.06 μM). (B) MCL-1 SAHB$_D$ dose-responsively sensitizes BID BH3-induced and BAK-dependent mitochondrial apoptosis, as measured by cytochrome c release assay performed on wild type and Bak$^{-/-}$ mitochondria. (C) The native interaction between BAK and MCL-1 was dose-responsively disrupted by treatment of OPM2 multiple myeloma cells with MCL-1 SAHBD, as assessed by MCL-1 immunoprecipitation and BAK western analysis.

Figure 17:
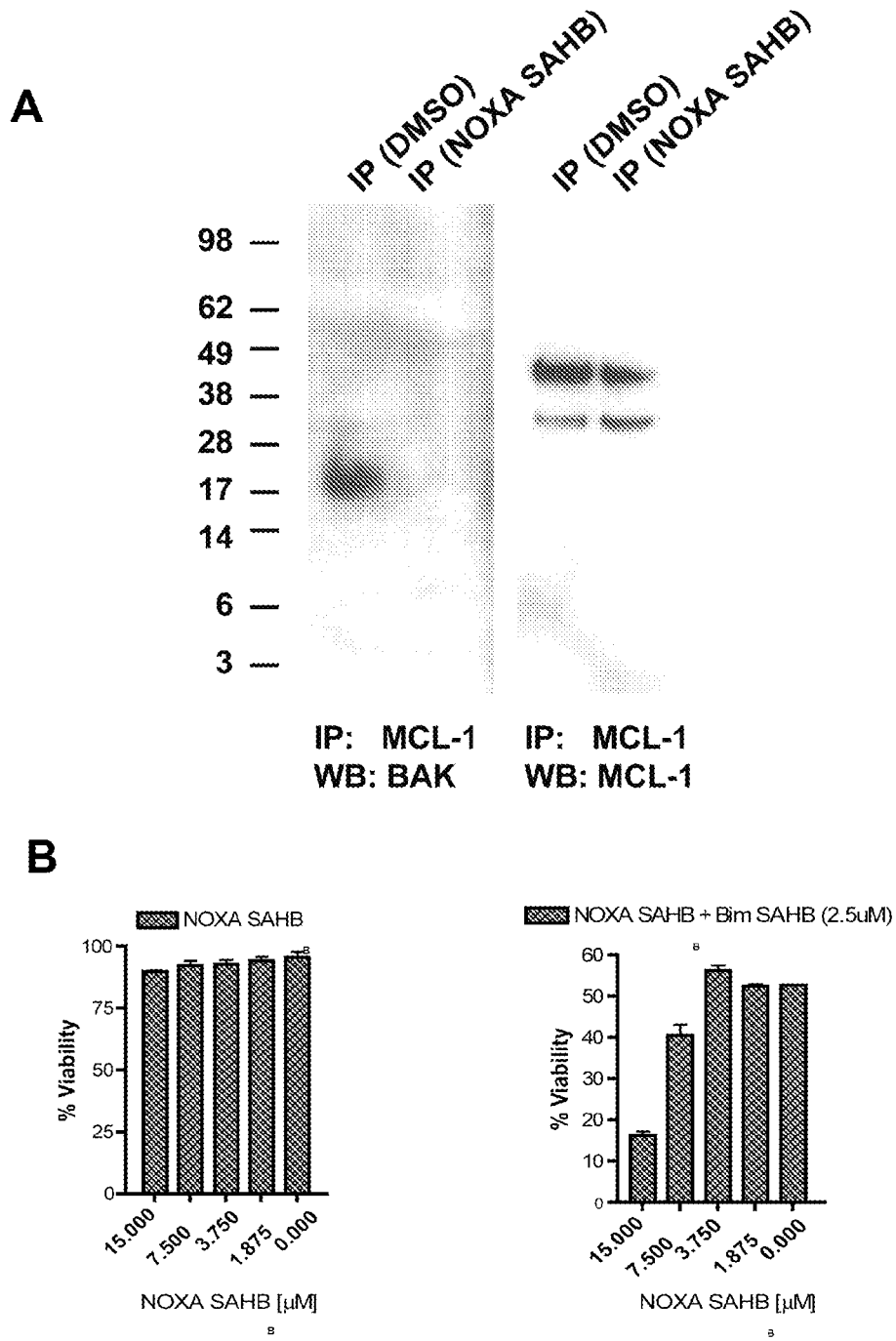

FIG. 17 (A) shows that NOXA SAHB targets MCL-1 in situ and disrupts the MCL-1/BAK interaction as demonstrated by MCL-1 co-immunoprecipitation; (B) illustrates that NOXA SAHB dose-responsively sensitizes chemoresistant U937 AML cells to low-dose, pro-apoptotic BIM SAHB.

Figure 18:
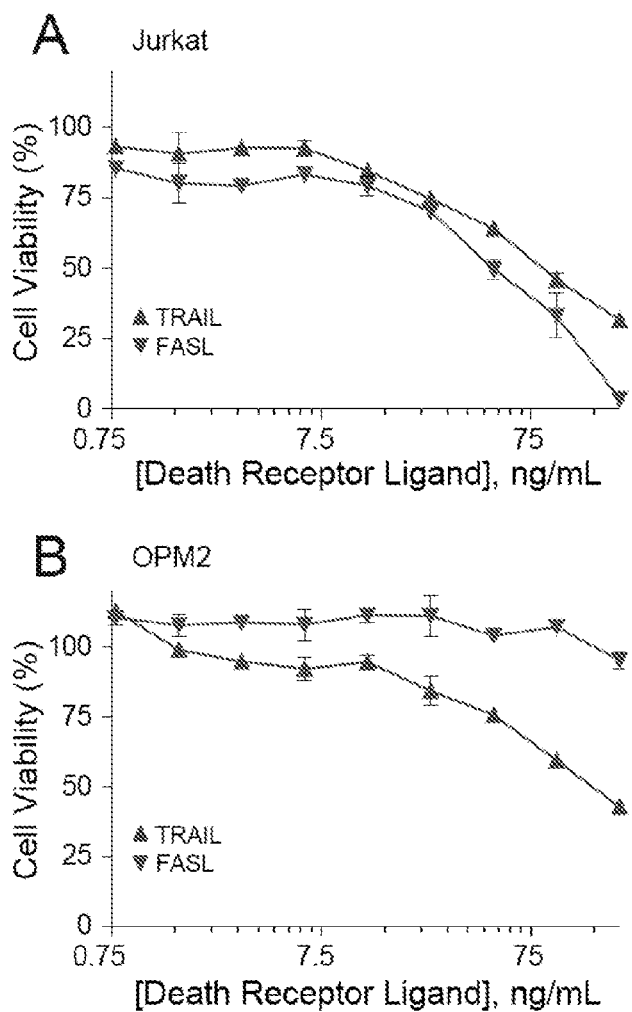

FIG. 18 shows that Jurkat and OPM2 cells were treated with increasing doses of TRAIL and Fas ligand (FasL), and cell viability was measured at 24 hours by MTT assay. Whereas TRAIL induced apoptosis of both Jurkat and OPM2 cells (A and B), only Jurkat cells were sensitive to FasL (A). These data represent baseline studies for the experiments performed in FIGS. 19-21.

Figure 19:
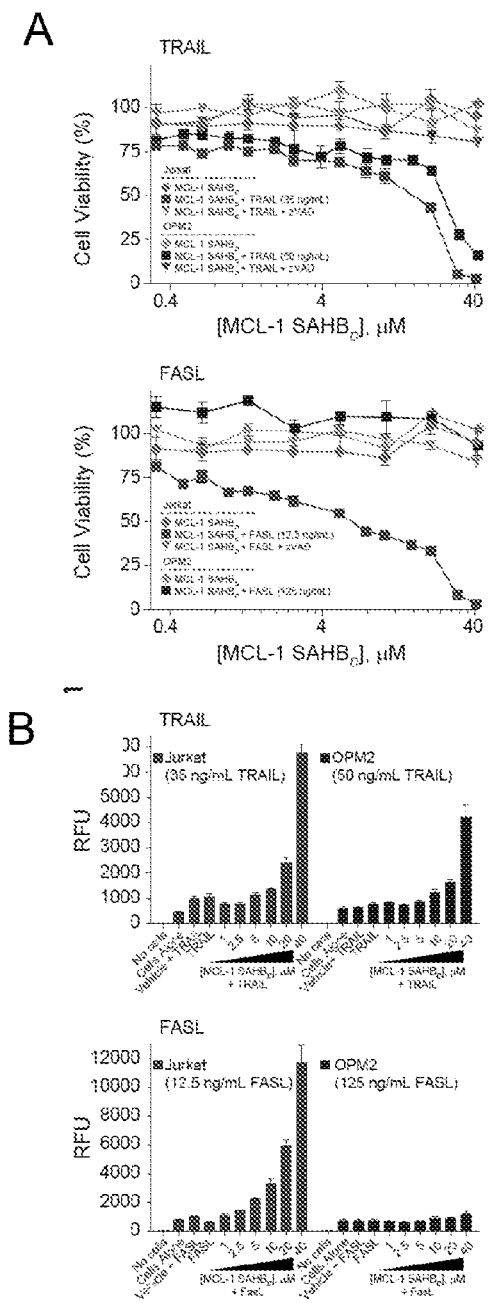

FIG. 19 shows that Jurkat T-cell leukemia and OPM2 cells were exposed to MCL-1 SAHB$_D$ singly and in combination with low dose death receptor agonists TRAIL and Fas ligand in the presence or absence of the pan-caspase inhibitor, z-VAD. Cell viability measured by MTT assay at 24 hours revealed dose-responsive and caspase-dependent sensitization of Jurkat (TRAIL and FasL) and OPM2 (TRAIL) cells by MCL-1 SAHB$_D$ (A). The capacity of MCL-1 SAHB$_D$ to sensitize Jurkat and OPM2 cells to death receptor stimuli correlated with dose-responsive activation of caspase 3/7, as measured by luminescence of DEVD-cleaved substrate ("DEVD" disclosed as SEQ ID NO: 94) (B). (A) Jurkat T-cell leukemia and OPM2 cells were exposed to MCL-1 SAHBD singly and in combination with low dose death receptor agonists TRAIL and Fas ligand in the presence or absence of the pan-caspase inhibitor, z-VAD. Cell viability measured by MTT assay at 24 hours revealed dose-responsive and caspase-dependent sensitization of Jurkat (TRAIL and FasL) and OPM2 (TRAIL) cells by MCL-1 SAHBD. (B) The capacity of MCL-1 SAHBD to sensitize Jurkat and OPM2 cells to death receptor stimuli correlated with dose-responsive activation of caspase 3/7, as measured by luminescence of DEVD-cleaved substrate ("DEVD" disclosed as SEQ ID NO: 94).

Figure 20:
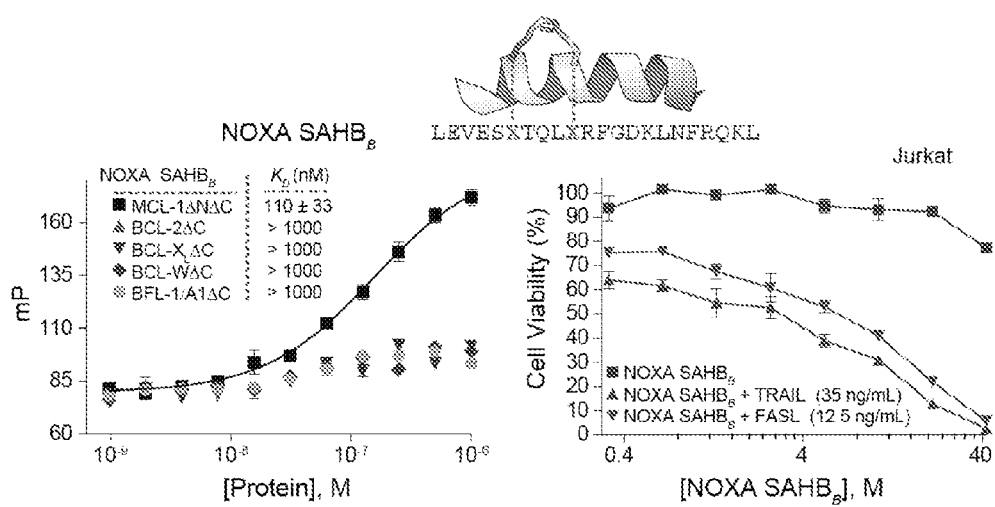

FIG. 20 shows that in contrast to contrast to NOXA SAHBA that binds both MCL-1ΔMΔC and BFL-1/A1ΔC, NOXA SAHBB, which contains an alternate staple position, exhibits potent and exclusive MCL-1ΔNΔC binding activity as measured by FPA. Like MCL-1 SAHB$_D$, NOXA SAHB$_B$ sensitized the apoptotic response of Jurkat cells to TRAIL and FasL, as measured by MTT assay at 24 hours. SE 1 ID NO: 7 corresponds to the "NOXA SAHB$_B$" peptide.

Figure 21:
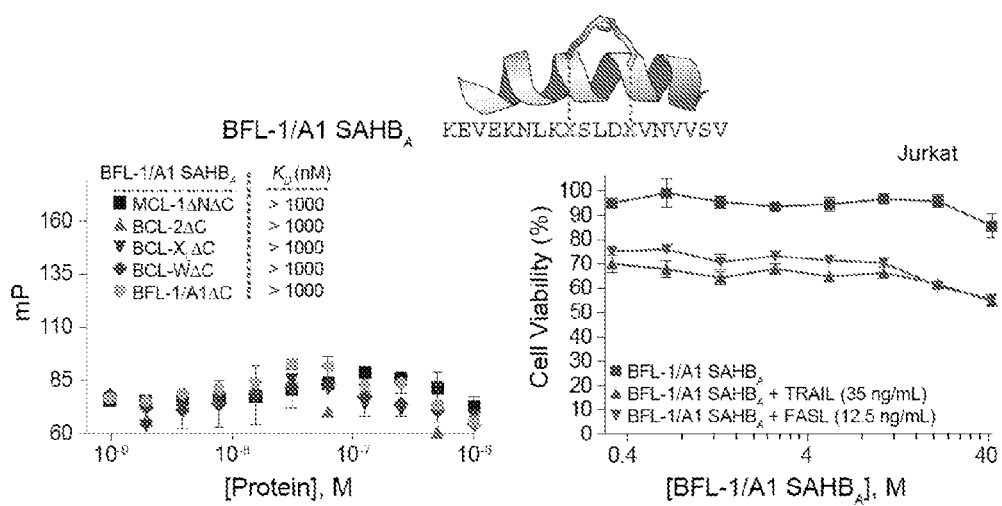

FIG. 21 shows that BFL-1 SAHB$_A$ exhibited no binding activity toward anti-apoptotic proteins by FPA and correspondingly showed no sensitization activity in Jurkat cells treated with low dose TRAIL or FasL. SE 1 ID NO: 16 corresponds to the "BFL-1 SAHB$_A$" peptide.

Figure 22:
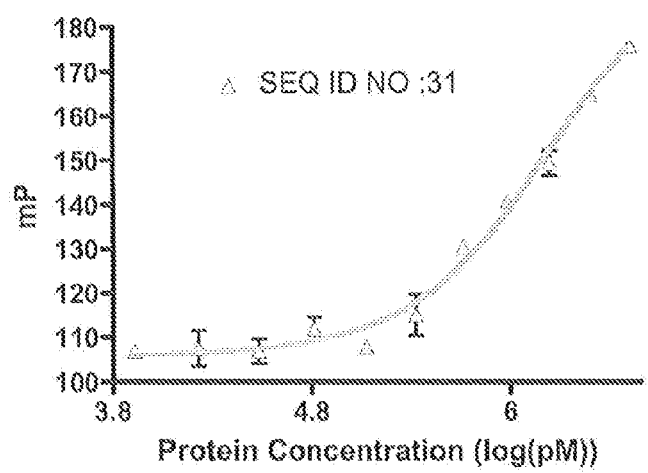

FIG. 22 shows that a shortened MCL-1 SAHB variant bind to MCL-1ΔNΔC with high affinity.

FIG. 23 provides the compositions of stapled BH3 peptides (SAHBs) generated to assess MCL-1 binding specificity and selectively target MCL-1.

DETAILED DESCRIPTION AND PREFERRED EMBODIMENTS

A series of stapled BCL-2 family peptide helices have now been identified that target the survival protein MCL-1 with high affinity and unprecedented selectivity. The MCL-1 inhibitor SAHBs described herein target the canonical BH3 groove of MCL-1, displacing the MCL-1/BAK interaction in vitro and in situ, and sensitizing MCL-1 dependent cancer cells to mitochondrial apoptosis.

DEFINITIONS

As used herein, the term "hydrocarbon stapling" or "stapling", refers to a process for stably cross-linking a polypeptide having at least two modified amino acids that helps to conformationally bestow the native secondary structure of that polypeptide. Hydrocarbon stapling allows a polypeptide, predisposed to have an alpha-helical secondary structure, to maintain its native alpha-helical conformation. This secondary structure increases resistance of the polypeptide to proteolytic cleavage and heat, and also may increase target binding affinity, hydrophobicity, and cell permeability. Accordingly, the hydrocarbon "stapled" (cross-linked) polypeptides described herein have improved biological activity relative to a corresponding non-hydrocarbon stapled (uncrosslinked) polypeptide. For example, the cross-linked polypeptide can include an alpha-helical domain of a BH3 BCL-2 homology domain, which, at least in the case of exemplary NOXA, BOK and MCL-1 BH3 domains, can competitively interfere with the interaction of MCL-1 protein with native ligands (including, e.g., formation of MCL-1 dimers and/or multimers and/or the MCL-1/BAK heterodimer), thereby modulating MCL-1 activity in a cell. Modulation of MCL-1 activity can produce a number of effects, including, e.g., promotion of apoptosis in a cell, modulation of cell cycle regulation in a cell, modulation of autophagy in a cell, modulation of cellular inflammatory responses, modulation of cellular autoimmune responses, and modulation of RNA splicing. The cross-linked polypeptides described herein can be used prophylactically or therapeutically, e.g., to treat or prevent hyperproliferative diseases, such as cancer.

The hydrocarbon stapled polypeptides include one or more tethers (linkages) between two non-natural amino acids, which tether significantly enhances the alpha helical secondary structure of the polypeptide. Generally, the tether extends across the length of one or two helical turns (i.e., about 3.4 or about 7 amino acids). Accordingly, amino acids positioned at i and i+3; i and i+4; or i and i+7 are ideal candidates for chemical modification and cross-linking. Thus, for example, where a peptide has the sequence . . . X1, X2, X3, X4, X5, X6, X7, X8, X9 . . . , cross-links between X1 and X4, or between X1 and X5, or between X1 and X8 are useful as are cross-links between X2 and X5, or between X2 and X6, or between X2 and X9, etc. represent hydrocarbon stapled forms of that peptide. The use of multiple cross-links (e.g., 2, 3, 4 or more) is also contemplated. The use of multiple cross-links is very effective at stabilizing and optimizing the peptide, especially with increasing peptide length. Thus, the invention encompasses the incorporation of more than one crosslink within the polypeptide sequence to either further stabilize the sequence or facilitate the structural stabilization, proteolytic resistance, acid stability, thermal stability, cellular permeability and biological activity enhancement of longer polypeptide stretches. Additional description regarding making and use of hydrocarbon-stapled polypeptides can be found, e.g., in U.S. Application No. 61/124,221, the contents of which is incorporated by reference herein in its entirety.

As used herein, the terms "stapled" and "hydrocarbon-stapled" are used interchangeably.

The term "stable" or "stabilized", as used herein with reference to a polypeptide, refers to polypeptides which have been hydrocarbon-stapled to maintain their natural alpha-helical structure and/or improve protease resistance and/or improve acid stability and/or improve thermal stability and/or improve cellular permeability and/or improve target binding affinity and/or improve biological activity.

The term "active site" of MCL-1 refers to a region of an MCL-1 polypeptide or MCL-1-interacting polypeptide, as a result of its shape, amino acid content, and charge potential, that favorably interacts or associates with another agent (including, without limitation, a protein, polypeptide, peptide, molecule, compound, antibiotic, drug, and/or nucleic acid) via various covalent and/or non-covalent binding forces. BCL-2 family members may have more than one active site, as recently reported (Gavathiotis et al. Nature, 455: 1076, 2008). An example of one defined "active site" on MCL-1 includes a hydrophobic groove and circumferential charged/hydrophilic residues which is capable of binding a stabilized alpha helix of a BCL-2 homology domain, such as human hydrocarbon-stapled MCL-1 BH3 (SEQ ID NO:1, 12, 17-60), NOXA BH3 (SEQ ID NO:2, 7, 63-68), BOK BH3 (SEQ ID NO:3, 11), or wild-type or MCL-1 specificity-tailored BIM BH3 (SEQ ID NO:4, 61, 62) or BAK BH3 (SEQ ID NO: 9, 69), or MULE BH3, a non-BCL-2 family member containing a BH3 homology domain (SEQ ID NO: 70), and which is formed by the juxtaposition of alpha helices 3, 4 and 5 of MCL-1 (PDB #2pqk and SEQ ID NO: 1), including residues V216, V220, H224, A227 and M231 of helix 3, residues V249, V253 and D255 of helix 4 and residues G262, T266 and F270 of helix 5 or formed by the juxtaposition of alpha helices 3, 4 and 5 of MCL-1 (PDB#2jm6), including residues V201, H205 and M212 of helix 3, residues S226, H233 and V234 of helix 4 and residues R244, T247, L249 and F251 of helix 5. In one embodiment, the active site includes two or more amino acids corresponding to G262 and F270 (PDB#2pqk, SEQ ID NO: 1).

The term "MCL-1 polypeptide variant" refers to polypeptides that vary from a reference MCL-1 family polypeptide by the addition, deletion or substitution of at least one amino acid to a natural amino acid or a non-natural amino acid or a mimetic thereof. It is well understood in the art that some amino acids may be changed to others with broadly similar properties without changing the nature of the activity of the polypeptide (e.g. conservative substitutions such as glutamine for glutamate or hydrophobic for hydrophobic or positively charged for positively charged) as described hereinafter. Accordingly, MCL-1 polypeptide variants as used herein encompass polypeptides that have pro- or anti-apoptotic activity. The term "variant" refers to a polypeptide having at least 30% amino acid sequence identity with a reference MCL-1 BCL-2 homology domain (e.g., MCL-1 BH3 domain) within a protein or any other functional domain thereof. More specifically, the term "variant" includes, but is not limited to, an MCL-1 polypeptide comprising an active site characterized by a three dimensional structure comprising the relative structural coordinates of alpha helices 3, 4 and 5 of MCL-1 (PDB #1pqk, SEQ ID NO: 1), including residues V216, V220, H224, A227 and M231 of helix 3, residues V249, V253 and D255 of helix 4 and residues G262, R263, T266 and F270 of helix 5 or of alpha helices 3, 4 and 5 of MCL-1 (PDB#2jm6, SEQ ID NO: 1), including residues V201, H205 and M212 of helix 3, residues S226, H233 and V234 of helix 4 and residues R244, T247, L249 and F251 of helix 5 of SEQ ID NO: 1, in each case, +/−a root mean square deviation from the conserved backbone atoms of those residues of not more than 1.1 angstroms, in certain embodiments not more than 1.0 angstroms, and in certain additional embodiments not more than 0.5 angstroms.

An "MCL-1 polypeptide variant" further includes those polypeptides, or their biologically active fragments, that comprise an amino acid sequence which is at least 30%, 40%, 50%, 60%, 70%, 80%, 90%, 95%, 96%, 97%, 98%, 99% or more similar to an amino acid sequence of an MCL-1 BCL-2 homology domain (e.g., BH3 domain). In certain embodiments, the BCL-2 homology domain comprises one or more conserved amino acid residues, such as amino acid residues corresponding to L213, G217, and/or D218 of MCL-1 (SEQ ID NO: 1) or conservative substitutions thereof.

The term "hydrophobic amino acid" means any natural or non-natural amino acid or mimetic thereof having an uncharged, non-polar side chain that is relatively insoluble in water. Examples of naturally occurring hydrophobic amino acids are alanine, leucine, isoleucine, valine, proline, phenylalanine, tryptophan and methionine.

The term "hydrophilic amino acid" means any natural or non-natural amino acid or mimetic thereof having an uncharged, polar side chain that is relatively soluble in water. Examples of naturally occurring hydrophilic amino acids are serine, threonine, tyrosine, asparagine, glutamine, and cysteine.

The term "negatively charged amino acid" includes any naturally occurring or non-natural amino acid or mimetic thereof having a negatively charged side chain under normal physiological conditions. Examples of negatively charged naturally occurring amino acids are aspartic acid and glutamic acid.

The term "positively charged amino acid" includes any naturally occurring or non-natural amino acid or mimetic thereof having a positively charged side chain under normal physiological conditions. Examples of positively charged naturally occurring amino acids are arginine, lysine and histidine.

As used herein, the term, "BCL-2 family polypeptide" refers to an evolutionary conserved family of proteins having as few as one to as many as four conserved BCL-2 homology domains (BH1, BH2, BH3 and/or BH4). The BH domains are alpha-helical segments and are present in both the anti-apoptotic and pro-apoptotic polypeptides of BCL-2 family proteins, which are conserved across many species, both at the sequence level and functionally (e.g., mouse BCL-2 family proteins bind human MCL-1). BCL-2 family polypeptides include BCL-2, BCL-XL, BCL-w, MCL-1, BCL-B, A1/BFL-1, BOO/DIVA, Nr-13, CED-9, BAX, BAK, BOK/MTD, BID, BAD, BIK/NBK, BLK, HRK, BIM/BOD, BNIP3, NIX, NOXA, PUMA, BMF, EGL-, and viral homologues. Functional BCL-2 family homology domains can also be found in non-BCL-2 family proteins, such as Beclin-1 (Oberstein et al. J Biol Chem, 282: 13123, 2007) and MULE (Zhong et al. Cell, 121:1085, 2005), which is a non-BCL-2 family protein that contains a BH3 domain. The skilled artisan will recognize that such non-BCL-2 family polypeptides can also be used in the compositions, methods and kits of the instant invention. Exemplary methods and compositions for modulating BCL-2 family polypeptides are described in U.S. 60/995,545, the contents of which is incorporated by reference herein in its entirety.

The term "anti-apoptotic polypeptide" refers to BCL-2 family polypeptides characterized by having one or more amino acid homology domains, BH1, BH2, BH3, and/or BH4, and that promote cell survival by attenuating or inhibiting apoptosis. The "anti-apoptotic polypeptides" further include those proteins, or their biologically active fragments, that are at least 30%, 40%, 50%, 60%, 70%, 80%, 90%, 95%, 96%, 97%, 98%, 99% or more similar in amino acid sequence to an anti-apoptotic BCL-2 homology domain within a BCL-2 family polypeptide. In certain embodiments, the BCL-2 homology domain comprises one or more conserved amino acid residue, such as amino acid residues corresponding to residues L213, G217, and or D218 of MCL-1's BH3 domain (PDB#1pqk, SEQ ID NO: 1). Anti-apoptotic polypeptides include MCL-1, BCL-2, BCL-X1, BCL-w, BCL-B, A1/BFL-1, BOO/DIVA, Nr-13, CED-9, and viral homologues.

The term "pro-apoptotic polypeptide" refers to BCL-2 family polypeptides characterized by having one or more amino acid homology domains, BH1, BH2, and/or BH3, and that promote cell death by activating apoptosis. The "pro-apoptotic polypeptides" further include those proteins, or their biologically active fragments, that are at least 30%, 40%, 50%, 60%, 70%, 80%, 90%, 95%, 96%, 97%, 98%, 99% or more similar in amino acid sequence to a pro-apoptotic BCL-2 homology domain within a BCL-2 family polypeptide. In certain embodiments, the BCL-2 homology domain comprises one or more conserved amino acid residues, such as amino acid residues corresponding to residues L29 and G33 of NOXA's BH3 domain (PubMed RefSeq: NP_066950.1, SEQ ID NO: 2, 5) or residues L70 and G75 of BOK's BH3 domain (PubMed RefSeq: NP_115904.1, SEQ ID NO: 3, 9). Pro-apoptotic polypeptides include BAX, BAK, BOK/MTD, BID, BAD, BIK/NBK, BLK, HRK, BIM/BOD, BNIP3, NIX, NOXA, PUMA, BMF, EGL-1, and viral homologs. An example of a non-BCL-2 family protein that regulates MCL-1 levels through targeted degradation, and is thus pro-apoptotic during physiologic stress, is the BH3 domain-containing ubiquitin ligase MULE.

As used herein, the term "apoptosis" refers to a regulated network of biochemical events which leads to a selective form of cell death that is characterized by readily observable morphological and biochemical changes, such as the fragmentation of the deoxyribo-nucleic acid (DNA), condensation of the chromatin, which may or may not be associated with endonuclease activity, chromosome migration, margination in cell nuclei, the formation of apoptotic bodies, mitochondrial swelling, widening of the mitochondrial cristae, opening of the mitochondrial permeability transition pores and/or dissipation of the mitochondrial proton gradient.

The term "compound" is used herein to denote a chemical agent, polypeptide, nucleic acid or combination thereof, or a mixture of chemical compounds and/or polypeptides and/or nucleic acids (e.g. DNA and/or RNA derivative), salts and solvates thereof, and the like. In certain embodiments, a compound of the invention binds to an active site of an MCL-1 polypeptide. A "modulator" is a compound which changes (e.g., enhances/promotes or inhibits/suppresses) the activity of an MCL-1 polypeptide.

The term "candidate compound" or "test compound" is used herein to denote a chemical compound, peptide, nucleic acid or combination thereof, or a mixture of chemical compounds and/or polypeptides and/or nucleic acids, salts and solvates thereof, and the like, which is tested by a method of the invention and is found to bind to an active site of an MCL-1 polypeptide, and thus is believed to modulate the activity of the MCL-1 polypeptide.

As used herein, "small molecule" is understood to refer to a chemical compound having a molecular weight below 2,000 daltons, more preferably between 300 and 1,000 daltons, and still more preferably between 400 and 700 daltons. It is preferred that these small molecules are organic molecules. In certain embodiments, "small molecule" does not include peptide or nucleic acid molecules.

The term "modulate" as used herein with reference to a compound refers to the activation or inhibition of anti-apoptotic or pro-apoptotic activity of a BCL-2 family polypeptide or affects other protein-protein interactions involving a BCL-2 family member or other protein target that binds a BCL-2 homology domain, and thereby regulates a biochemical pathway (e.g. unfolded protein response, glucose-stimulated insulin secretion, apoptosis). Methods for assaying both anti-apoptotic, pro-apoptotic, and other biochemical activities (e.g. unfolded protein response, glucose-stimulated insulin secretion, apoptosis) are well known in the art and described herein.

As used herein, the term "interacts" or "binds" refers to a condition of proximity between a compound, or portions thereof, and the active site of a BCL-2 family polypeptide or portions thereof. The interaction is between one or more moieties on the compound and one or more moieties of the amino acids of the active site. The association may be non-covalent—wherein the juxtaposition is energetically favored by hydrogen bonding or van der Waals or electrostatic interactions—or it may be covalent. For example, hydrophobic and hydrophilic amino acid residues of alpha helices 3, 4 and 5 of the MCL-1 polypeptide, including residues V216, V220, H224, A227 and M231 of helix 3, residues V249, V253 and D255 of helix 4 and residues G262, R263 T266 and F270 of helix 5 are predicted to interact with residues T212, L213, R214, V216, G217, D218 and V220 of MCL-1 BH3 domain (PubMed RefSeq: NP_068779.1, SEQ ID NO: 1, 16), residues A26, L29, G33 and L36 of NOXA BH3 domain (PubMed RefSeq: NP_066950.1, SEQ ID NO: 2, 5) and residues V66, V69, L70, G75 and L79 of BOK BH3 domain (PubMed RefSeq:NP_115904.1, SEQ ID NO: 3, 9).

The term, "activates" refers to an increase in the anti-apoptotic or pro-apoptotic activity of a BCL-2 family polypeptide or other defined biochemical activity based upon protein-protein or protein-nucleic acid interaction. A compound that activates a pro-apoptotic activity will bind to an active site of a BCL-2 family polypeptide and cause, for example, a 1.5×, 2×, 3×, 4×, 5×, 6×, 7×, 8×, 9×, 10×, 15×, 20× or more increase in the pro-apoptotic activity of the BCL-2 family polypeptide when compared with a control lacking the compound. In another embodiment, a compound that activates an anti-apoptotic activity will bind to an active site of a BCL-2 family polypeptide and cause, for example, a 1.5×, 2×, 3×, 4×, 5×, 6×, 7×, 8×, 9×, 10×, 15×, 20× or more increase in the anti-apoptotic (survival) activity of the BCL-2 family polypeptide when compared with a control lacking the compound. In another embodiment, a compound that modulates a biochemical activity (e.g. cell cycle, autophagy) will bind to an active site of a BCL-2 family polypeptide or other BCL-2 homology domain binding target protein and cause, for example, a 1.5×, 2×, 3×, 4×, 5×, 6×, 7×, 8×, 9×, 10×, 15×, 20× or more increase in the biochemical activity of the target protein when compared with a control lacking the compound. Assays for assessing the activation of an anti-apoptotic or pro-apoptotic activity or the modulation of a biochemical activity (e.g. induction of autophagy, induction of cell cycle arrest) are known in the art and described herein.

The term "inhibits" refers to a decrease or blocking of the anti-apoptotic or pro-apoptotic activity of a BCL-2 family polypeptide, or other defined biochemical activity based upon protein-protein interaction. For example, a compound that inhibits a pro-apoptotic activity will bind to an active site of a BCL-2 family polypeptide and prevent activation or reduce the activity of the BCL-2 family polypeptide. Thus, the compound will inhibit or decrease the effects of a pro-apoptotic activity. Thus, pro-apoptotic activity, e.g., cell death, will be less than, for example, 75%, 70%, 60%, 50%, 40%, 30%, 20%, 10%, 5% or less in a population of cells in which an inhibitor is present than compared to a control cell population where the compound is not present. In another embodiment, a compound that inhibits an anti-apoptotic activity will bind to an active site of a BCL-2 family polypeptide and prevent or reduce the anti-apoptotic activity of the BCL-2 family polypeptide. Thus, anti-apoptotic activity, e.g., survival, will be less than, for example, 75%, 70%, 60%, 50%, 40%, 30%, 20%, 10%, 5% or less in a population of cells in which an inhibitor is present than compared to a control cell population where the compound is not present. In yet another embodiment, a compound that modulates a biochemical activity (e.g. cell cycle, autophagy) will bind to an active site of a BCL-2 family polypeptide or other BCL-2 homology domain binding target protein and prevent or reduce the biochemical activity of the protein target. Thus, the biochemical activity (e.g., autophagy, cell cycle arrest) will be less than, for example, 75%, 70%, 60%, 50%, 40%, 30%, 20%, 10%, 5% or less in a population of cells in which an inhibitor is present than compared to a control cell population where the compound is not present.

As used herein, the term "BH3 SAHB" refers to the BCL-2 homology domain 3 of a BCL-2 family polypeptide and/or a BH3 domain-containing polypeptide (e.g., MULE) that has been hydrocarbon stapled so as to form a stabilized alpha helix. The amino acid sequences of numerous BH3 domains are described herein, (e.g., FIGS. 7, 9, and 15). Methods of making BH3 SAHB's are known in the art and described in U.S. Patent Publication No. US2005/0250680, filed Nov. 5, 2004, which is herein incorporated by reference in its entirety.

As used herein, the term "NOXA BH3 polypeptide" refers to a polypeptide having a BCL-2 homology domain 3 of NOXA. In one embodiment, the NOXA BH3 polypeptide has an amino acid sequence which is 30%, 40%, 50%, 60%, 70%, 80%, 90%, 95%, 96%, 97%, 98%, 99% or more identical to SEQ ID NO: 2 (FIG. 5) and includes one or more of amino acid residues corresponding to L29, G33, and/or D34 of SEQ ID NO: 2 or conservative substitutions thereof. Optionally, the NOXA BH3 domain of the NOXA BH3 polypeptide has an amino acid sequence which is 30%, 40%, 50%, 60%, 70%, 80%, 90%, 95%, 96%, 97%, 98%, 99% or more identical to the BH3 domain of SEQ ID NO: 2. In certain embodiments, the NOXA BH3 polypeptide has the amino acid sequences of SEQ ID NO: 7, and SEQ ID NO: 63-68. In certain embodiments, the scope of the term "NOXA BH3 polypeptide" encompasses biologically active fragments of SEQ ID NO: 2, while the scope of "NOXA BH3 domain" similarly encompasses biologically active fragments of the BH3 domain of SEQ ID NO: 2.

As used herein, the term "BOK BH3 polypeptide" refers to a polypeptide having a BCL-2 homology domain 3 of BOK. In one embodiment, the BOK BH3 polypeptide has an amino acid sequence which is 30%, 40%, 50%, 60%, 70%, 80%, 90%, 95%, 96%, 97%, 98%, 99% or more identical to SEQ ID NO: 3 (FIG. 6) and includes one or more of amino acid residues corresponding to residues L70, G75, and/or D76 of SEQ ID NO: 3 or conservative substitutions thereof. Optionally, the BOK BH3 domain of the BOK BH3 polypeptide has an amino acid sequence which is 30%, 40%, 50%, 60%, 70%, 80%, 90%, 95%, 96%, 97%, 98%, 99% or more identical to the BH3 domain of SEQ ID NO: 3. In certain embodiments, the BOK BH3 polypeptide has the amino acid sequence of SEQ ID NO: 11. In certain embodiments, the scope of the term "BOK BH3 polypeptide" encompasses biologically active fragments of SEQ ID NO: 3, while the scope of "BOK BH3 domain" similarly encompasses biologically active fragments of the BH3 domain of SEQ ID NO: 3.

As used herein, the term "MCL-1 BH3 polypeptide" refers to a polypeptide having a BCL-2 homology domain 3 of MCL-1. In one embodiment, the MCL-1 BH3 polypeptide has an amino acid sequence which is 30%, 40%, 50%, 60%, 70%, 80%, 90%, 95%, 96%, 97%, 98%, 99% or more identical to SEQ ID NO: 1 and includes one or more of amino acid residues corresponding to L213 and G217 of SEQ ID NO: 1 (FIG. 4) or conservative substitutions thereof. Optionally, the MCL-1 BH3 domain of the MCL-1 BH3 polypeptide has an amino acid sequence which is 30%, 40%, 50%, 60%, 70%, 80%, 90%, 95%, 96%, 97%, 98%, 99% or more identical to the BH3 domain of SEQ ID NO: 1. In certain embodiments, the MCL-1 BH3 polypeptide has the amino acid sequences of SEQ ID NO: 12, 17-60. In certain embodiments, the scope of the term "MCL-1 BH3 polypeptide" encompasses biologically active fragments of SEQ ID NO: 1, while the scope of "MCL-1 BH3 domain" similarly encompasses biologically active fragments of the BH3 domain of SEQ ID NO: 1.

As used herein, the term "MCL-1-specificity tailored BH3 polypeptide" refers to a polypeptide having a BCL-2 homology domain 3 of BCL-2 family members (FIGS. 1B, 7) that has been mutated to make its binding activity MCL-1 selective. In one embodiment, the BH3 polypeptide has an amino acid sequence which is 30%, 40%, 50%, 60%, 70%, 80%, 90%, 95%, 96%, 97%, 98%, 99% or more identical to BIM BH3, SEQ ID NO: 4 and includes one or more of amino acid residues corresponding to L152 and G156 of SEQ ID NO: 4 (enumeration based on NCBI#NP_619527) or conservative substitutions thereof, but also includes one or more of amino acid residue mutations, for example converting I155 to F and/or E158 to K in SEQ ID NO: 3 or conservative substitutions thereof, to achieve MCL-1 specificity. In certain embodiments, the MCL-1-specificity tailored BIM BH3 polypeptide has the amino acid sequences of SEQ ID NO: 62. In another embodiment, the BH3 polypeptide has an amino acid sequence which is 30%, 40%, 50%, 60%, 70%, 80%, 90%, 95%, 96%, 97%, 98%, 99% or more identical to BAK BH3, SEQ ID NO: 9 and includes one or more of amino acid residues corresponding to L74 and G78 of SEQ ID NO: 6 (enumeration based on NCBI#NP_619527) or conservative substitutions thereof, but also includes one or more of amino acid residue mutations, for example converting I77 to F and/or D84 to K (enumeration based on NCBI#NP_001179) or conservative substitutions thereof, in SEQ ID NO: 69 to achieve MCL-1 specificity.

As used herein, the term "non-BCL-2 family member BH3 polypeptide" refers to a polypeptide having a BCL-2 homology domain 3 but is otherwise not traditionally classified as a BCL-2 family member or homologue. In one embodiment, the non-BCL-2 family member BH3 polypeptide has an amino acid sequence which is 30%, 40%, 50%, 60%, 70%, 80%, 90%, 95%, 96%, 97%, 98%, 99% or more identical to SEQ ID NO: 70 and includes one or more of amino acid residues corresponding to L1980 and G1984 (enumeration based on NCBI#AAY98258) of SEQ ID NO: 70 (FIG. 13) or conservative substitutions thereof.

The term "pharmacologically effective amount," "therapeutically effective amount", "pharmacologically effective dose" or simply "effective amount" refers to that amount of an agent effective to produce the intended pharmacological, therapeutic or preventive result. The pharmacologically effective amount results in the amelioration of one or more symptoms of a disorder, or prevents the advancement of a disorder, or causes the regression of the disorder, or prevents the disorder. For example, with respect to the treatment of a disorder of excessive cellular survival or proliferation, a therapeutically effective amount preferably refers to the amount of a therapeutic agent that decreases the rate of tumor growth, decreases tumor mass, decreases the number of metastases, increases time to tumor progression, or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

For example, with respect to the treatment of a disorder associated with increased cellular death, e.g., ischemia, a therapeutically effective amount preferably refers to the amount of a therapeutic agent that prevents or limits tissue and/or cellular damage that would otherwise occur if treatment was not administered. The therapeutic agent decreases tissue and/or cellular damage by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% compared to damage that occurs without the administration of a therapeutic agent of the invention.

The terms "treat," and "treating," as used herein with reference to a disorder (e.g., hyperpoliferative disorder, excessive cellular survival or proliferation), refers to a decrease in the occurrence of pathological cells (e.g., hyperproliferative or neoplastic cells) in an animal or human. The prevention may be complete, e.g., the total absence of pathological cells in a subject. The prevention may also be partial, such that the occurrence of pathological cells in a subject is less than that which would have occurred without the present invention. In some embodiments, such terms refer to one, two, three or more results following the administration of one or more therapies: (1) a stabilization, reduction or elimination of the cancer cell population, (2) an increase in the length of remission, (3) a decrease in the recurrence rate of cancer, (4) an increase in the time to recurrence of cancer, and (6) an increase in the survival of the patient.

The terms "treat," and "treating," as used herein with reference to a disorder associated with increased cellular death, e.g., ischemia, refer to a decrease in the occurrence of tissue and/or cellular damage in an animal or human. The prevention may be complete, e.g., the total absence of tissue damage in a subject. The prevention may also be partial, such that the occurrence of tissue damage in a subject is less than that which would have occurred without the therapeutic agent.

The terms "prevent," "preventing," and "prevention," as used herein, shall refer to a decrease in the occurrence of a disease or decrease in the risk of acquiring a disease or its associated symptoms in a subject. The prevention may be complete, e.g., the total absence of disease or pathological cells in a subject. The prevention may also be partial, such that the occurrence of the disease or pathological cells in a subject is less than that which would have occurred without the present invention.

The term "subject" refers to an animal or human, or to one or more cells derived from an animal or human. Preferably, the subject is a human. Subjects can also include non-human primates. Cells may be in any form, including but not limited to cells retained in tissue, cell clusters, immortalized, transfected or transformed cells, and cells derived from an animal that has been physically or phenotypically altered. A human subject can be known as a patient.

The term "anti-tumor activity" refers to the ability of a substance or composition to block the proliferation of, or to induce the death of tumor cells which interact with that substance or composition.

As used herein, a "MCL-1 associated disorder", refers to a disorder associated with a deregulated MCL-1 polypeptide, particularly increased expression of MCL-1. An MCL-1 associated disorder is characterized by having an MCL-1 at least a 10%, 20%, 30%, 40%, 50%, 60%, 70%, 80%, 90%, or more increase in the level of MCL-1 expression as compared to a normal control cell, preferably from the same subject. MCL-1 associated disorders are associated with excessive cellular survival and/or proliferation, e.g., cancer, or deregulation of the cell cycle, or deregulation of the autophagic pathway, or deregulation of cellular autoimmune or inflammatory responses of a subject, or deregulation of RNA splicing. An MCL-1 associated disorder need not be diagnosed by identification of deregulated MCL-1. Instead, the disorder can initially be diagnosed by typical methods, e.g., imaging studies, physical examination, biopsy, blood analysis, and confirmed to be an MCL-1 associated disorder by histological analysis, PCR, or other methods known in the art. MCL-1 associated disorders include those described herein.

As used herein, a "hyperproliferative disorder" means cancer, neoplastic growth, hyperplastic or proliferative growth or a pathological state of abnormal cellular development or survival and includes solid tumors, non-solid tumors, and any abnormal cellular proliferation or accumulation, such as that seen in leukemia.

The terms "anticancer agent" and "anticancer drug," as used herein, refer to any therapeutic agents (e.g., chemotherapeutic compounds and/or molecular therapeutic compounds), antisense therapies, antibody therapies, peptide therapies, nucleic acid therapies (e.g. RNAi), radiation therapies, or combinations thereof, used in the treatment of hyperproliferative diseases such as cancer. In one embodiment, the invention is directed to methods of treating an MCL-1 associated disorder comprising administering an effective dose of an anticancer agent and a compound which binds to the active site, as described herein, of an MCL-1 polypeptide.

As used herein in relation to the position of an amino acid, e.g., L213 and G217 of SEQ ID NO: 1, the term "corresponding to" refers to an amino acid in a first polypeptide sequence, e.g., MCL-1, that aligns with a given amino acid in a reference polypeptide sequence, e.g., NOXA, when the first polypeptide and reference polypeptide sequences are aligned by homology or other algorithms (e.g., structural comparison). Alignment is performed by one of skill in the art using software designed for this purpose, for example, BLASTP version 2.2.2 with the default parameters for that version. Corresponding amino acids can also be identified upon structural comparisons of a first polypeptide sequence and a second polypeptide sequence. Such structural comparisons are known in the art and described herein. For example, Petros et al. Biochimica et Biophysica Acta 1644; 83-94 (2004) and Suzuki et al., Cell. 103; 645-654 (2000) illustrated structural alignments between BCL-2 homology domains of BCL-2 family members.

The term "amino acid" refers to a molecule containing both an amino group and a carboxyl group. Suitable amino acids include, without limitation, both the D- and L-isomers of the 20 common naturally occurring amino acids found in peptides (e.g., A, R, N, C, D, Q, E, G, H, I, L, K, M, F, P, S, T, W, Y, V (as known by the one letter abbreviations)) as well as the naturally occurring and non-naturally occurring amino acids (e.g., norleucine, modified amino acids to allow for peptide stapling, amino acids linked by bonds other than peptide bonds) prepared by organic synthesis or other metabolic routes.

A "non-essential" amino acid residue is a residue that can be altered from the wild-type sequence of a polypeptide (e.g., MCL-1 BH3) without abolishing or substantially altering its ligand binding ability or otherwise significantly impacting, particularly decreasing, an activity of the polypeptide (e.g., reduces activity of the peptide less than 40%, less than 30%, less than 20%, less than 10%). In certain embodiments, the activity of a peptide can be increased by modification of a non-essential amino acid. An "essential" amino acid residue is a residue that, when altered from the wild-type sequence of the polypeptide, results in abolishing or substantially abolishing the polypeptide's binding activity to an MCL-1 active site or otherwise dramatically alters the polypeptide's activity (e.g., decreases activity by at least 60%, at least 70%, at least 80%, or at least 90%). In certain specific examples, an "essential" amino acid residue is limited to a residue that, when altered from the wild-type sequence of the polypeptide, results in abolishing or substantially abolishing the polypeptide's binding activity. For example, the essential and non-essential amino acid residues of the BH3 domains of MCL-1, NOXA, BOK or other BCL-2 family polypeptide can readily be determined by methods well known in the art and described herein. The term "essential" amino acid residue, as used herein, includes conservative substitutions of the essential amino acid. Generally, the "essential" amino acid residues are found at the interacting face of the BH3 polypeptide with the active site of the MCL-1 polypeptide.

As used herein, an "interacting face" is understood as a surface of a protein that interacts with another protein or binding partner. The peptides of the invention are substantially alpha-helical. Alpha-helicies include 3.6 amino acids per turn, i.e., the positions of the amino acid in a helical peptide can be considered to be in positions abcdefgabcdefg . . . for the length of the helix. Therefore, the "face" of the alpha-helix could be formed amino acids at positions a and d, b and e, c and f, etc. which "stack" on top of each other creating a "face". The "face" can be wider than a single amino acid, wherein all positions a, b, d, and e form a face; or c, d, g, and a form a face; or the width of the face varies along the face but is composed of adjacent and/or "stacked" amino acids in the helix. In the peptides of the invention, it is preferred that the staple is not attached to amino acids that interact directly with the binding protein (e.g., MCL-1). As demonstrated by the alanine scan and staple scan herein, the peptides are typically more tolerant to mutations or alterations on the non-interacting face of the alpha-helix and less tolerant of mutations on the interacting face of the alpha-helix. Staples and mutations can be tolerated, and sometimes beneficial when made on the interacting face either immediately N- or C-terminal to the portion of the helix that interacts with the interacting protein. For example, it is noted that placement of a staple adjacent to the interacting face of the helix results in an increased affinity of the peptide for the target protein. Identification of amino acids on the interacting and non-interacting faces of the peptides of the invention is well within the ability of those of skill in the art.

A "conservative amino acid substitution" is one in which the amino acid residue is replaced with a natural or non-natural amino acid residue having a similar side chain. For example, families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, norleucine, proline, phenylalanine, methionine, tryptophan), beta-branched side chains (e.g., threonine, valine, isoleucine) and aromatic side chains (e.g., tyrosine, phenylalanine, tryptophan, histidine). Other conserved amino acid substitutions can also occur across amino acid side chain families, such as when substituting an asparagine for aspartic acid in order to modify the charge of a peptide. Thus, a predicted nonessential amino acid residue in a BH3 domain polypeptide, for example, is preferably replaced with another amino acid residue from the same side chain family or homologues across families (e.g. asparagine for aspartic acid, glutamine for glutamic acid). In addition, individual substitutions, deletions or additions that alter, add or delete a single amino acid or a small percentage of amino acids in an encoded sequence are also considered "conservative substitutions." Appropriate conservative amino acid substitutions can also be identified by alignment with protein isoforms from other animals that express the same protein. In preferred embodiments, human sequences are compared with other mammalian sequences to identify possible conservative amino acid changes. Other mammals for sequence comparison include, but are not limited to, mouse, rat, dog, cat, cow, goat, rabbits, and non-human primates. Methods to perform sequence alignments are well known as discussed herein.

The terms "identical" or "percent identity," in the context of two or more nucleic acids or polypeptide sequences, refer to two or more sequences or subsequences that are the same or have a specified percentage of nucleotides or amino acids that are the same, when compared and aligned for maximum correspondence, as measured using one of the following sequence comparison algorithms, or by visual inspection.

"Similarity" or "percent similarity" in the context of two or more polypeptide sequences, refer to two or more sequences or subsequences that are the same or have a specified percentage of amino acid residues, or conservative substitutions thereof, that are the same when compared and aligned for maximum correspondence, as measured using one of the following sequence comparison algorithms, or by visual inspection. By way of example, a first protein region can be considered similar to a region of an anti-apoptotic MCL-1 protein when the amino acid sequence of the first region is at least 30%, 40%, 50%, 60%, 70%, 75%, 80%, 90%, or even 95% identical, or conservatively substituted, to a region of a second MCL-1 protein or other protein (e.g., NOXA protein) when compared to any sequence in the second protein of an equal number of amino acids as the number contained in the first region, or when compared to an alignment of MCL-1 and homologs thereof (e.g., anti-apoptotic BCL-2 family member proteins) that has been aligned by a computer similarity program known in the art, as discussed below. Preferably, the polypeptide region of the first protein and the second protein includes one or more conserved amino acid residues, e.g., such as those illustrated in FIGS. 1, 7, and 15.

As used herein, the terms "identity" or "percent identity", refers to the subunit sequence similarity between two polymeric molecules, e.g., two polynucleotides or two polypeptides. When a subunit position in both of the two molecules is occupied by the same monomeric subunit, e.g., if a position in each of two peptides is occupied by serine, then they are identical at that position. The identity between two sequences is a direct function of the number of matching or identical positions, e.g., if half (e.g., 5 positions in a polymer 10 subunits in length), of the positions in two peptide or compound sequences are identical, then the two sequences are 50% identical; if 90% of the positions, e.g., 9 of 10 are matched, the two sequences share 90% sequence identity. The identity between two sequences is a direct function of the number of matching or identical positions. Thus, if a portion of the reference sequence is deleted in a particular peptide, that deleted section is not counted for purposes of calculating sequence identity. Identity is often measured using sequence analysis software e.g., BLASTN or BLASTP (www.ncbi.nih.gov/BLAST/). The default parameters for comparing two sequences (e.g., "Blast"-ing two sequences against each other), by BLASTN (for nucleotide sequences) are reward for match=1, penalty for mismatch=−2, open gap=5, extension gap=2. When using BLASTP for protein sequences, the default parameters are reward for match=0, penalty for mismatch=0, open gap=11, and extension gap=1. Additional, computer programs for determining identity are known in the art.

"Similarity" or "percent similarity" in the context of two or more polypeptide sequences, refer to two or more sequences or subsequences that are the same or have a specified percentage of amino acid residues, or conservative substitutions thereof, that are the same when compared and aligned for maximum correspondence, as measured using one of the following sequence comparison algorithms, or by visual inspection. By way of example, a first polypeptide can be considered similar to BH3 domain of MCL-1 when the amino acid sequence of the first polypeptide is at least 20%, 30%, 40%, 50%, 60%, 70%, 75%, 80%, 90%, or even 95% or more identical, or conservatively substituted, to a region of the BH3 domain of MCL-1 when compared to any sequence of an equal number of amino acids as the number contained in the first polypeptide as aligned by a computer similarity program known in the art and described herein. Preferably, the polypeptide region of the first protein and the second protein includes one or more conserved amino acid residues.

The term "amino acid side chain" refers to a moiety attached to the α-carbon in an amino acid. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally occurring amino acid side chains are also included, for example, those that occur in nature (e.g., an amino acid metabolite) or those that are made synthetically (e.g., an alpha di-substituted amino acid).

The term "polypeptide" encompasses two or more naturally occurring or synthetic amino acids linked by a covalent bond (e.g., an amide bond). Polypeptides as described herein include full length proteins (e.g., fully processed proteins) as well as shorter amino acids sequences (e.g., splice variants of naturally occurring proteins, fragments of naturally occurring proteins or synthetic polypeptide fragments).

The term "selective MCL-1 binding agent," as used herein, refers to an agent possessing greater ability to bind MCL-1 than to bind a non-MCL-1 anti-apoptotic multidomain protein (e.g., BCL-2, BCL-XL, BCL-B, BCL-w and BFL-1/A1). A "selective MCL-1 binding agent" is an agent capable of binding MCL-1 polypeptide with at least 1.5-fold greater affinity than the agent is capable of binding a non-MCL-1 BCL-2 family polypeptide. In certain embodiments, a selective MCL-1 binding agent is capable of binding MCL-1 polypeptide at least 2-fold, 3-fold, 4-fold, 5-fold, 10-fold, 20-fold, 50-fold, 100-fold, 1000-fold or more than the selective MCL-1 binding agent is capable of binding a non-MCL-1 BCL-2 family polypeptide. Optionally, a selective MCL-1 inhibitor is capable of binding MCL-1 polypeptide at least 1.5-fold, 2-fold, 3-fold, 4-fold, 5-fold, 10-fold, 20-fold, 50-fold, 100-fold, 1000-fold or more than the selective MCL-1 binding agent is capable of binding any other BCL-2 family polypeptide. In certain embodiments, a "selective MCL-1 binding agent" binds MCL-1 with a $K_D$ of approximately less than or equal to 1, 2, 5, 10, 20, 50, 100, 150 or 200 nM, whereas a non-MCL-1 BCL-2 family polypeptide (or all non-MCL-1 BCL-2 family polypeptides) is bound with a $K_D$ of approximately 300, 400 or greater than 500 nM. Identification or assessment of an agent as a "selective MCL-1 binding agent" can be performed either directly via assessment of a physical interaction of an agent with a domain of an MCL-1 polypeptide relative to interaction of the agent with such a domain in a non-MCL-1 anti-apoptotic multidomain protein (e.g., monitoring of the ability of a test agent to bind to the active site of MCL-1 relative to the ability of the agent to bind to the active site of BCL-2), or indirectly via assessment of MCL-1 activity relative to the activity of a non-MCL-1 anti-apoptotic multidomain protein, e.g., via monitoring the modulation of MCL-1 activity by an agent (e.g., a test agent). Binding of such "MCL-1 binding agents" to an MCL-1 polypeptide may inhibit MCL-1 polypeptide activity, activate MCL-1 polypeptide activity, otherwise modulate the activity of MCL-1 polypeptide, or effect no alteration in MCL-1 polypeptide activity, depending upon the identity of the binding agent.

The term "selective MCL-1 inhibitor," as used herein, refers to an agent possessing greater ability to inhibit MCL-1 activity than to inhibit the activity of a non-MCL-1 anti-apoptotic multidomain protein (e.g., BCL-2, BCL-XL, BCL-B, BCL-w and BFL-1/A1). A "selective MCL-1 inhibitor" can be a therapeutic compound of any type, including small molecule-based, peptide-based, antibody-based, antisense-based, small interfering RNA ("siRNA")-based, microRNA ("miRNA")-based compounds, or combination thereof. The inventive methods are useful with any known or hereafter developed selective MCL-1 inhibitor. A "selective MCL-1 inhibitor" is an agent capable of inhibiting MCL-1 activity with at least 1.5-fold greater efficacy or potency than the agent is capable of inhibiting the activity of a non-MCL-1 BCL-2 family polypeptide. In certain embodiments, a selective MCL-1 inhibitor is capable of inhibiting MCL-1 activity at least 2-fold, 3-fold, 4-fold, 5-fold, 10-fold, 20-fold, 50-fold, 100-fold, 1000-fold or more than the selective MCL-1 inhibitor is capable of inhibiting the activity of a non-MCL-1 BCL-2 family polypeptide. Optionally, a selective MCL-1 inhibitor is capable of inhibiting MCL-1 activity at least 1.5-fold, 2-fold, 3-fold, 4-fold, 5-fold, 10-fold, 20-fold, 50-fold, 100-fold, 1000-fold or more than the selective MCL-1 inhibitor is capable of inhibiting the activity of any other BCL-2 family polypeptide. In certain embodiments, a "selective MCL-1 inhibitor" binds MCL-1 with a $K_D$ of approximately less than or equal to 1, 2, 5, 10, 20, 50, 100, 150 or 200 nM, whereas a non-MCL-1 BCL-2 family polypeptide (or all non-MCL-1 BCL-2 family polypeptides) is bound with a $K_D$ of approximately 300, 400 or greater than 500 nM. Identification or assessment of an agent as a "selective MCL-1 inhibitor" can be performed either directly or indirectly by assessing MCL-1 activity relative to the activity of a non-MCL-1 anti-apoptotic multidomain protein, e.g., via monitoring of modulation of MCL-1 activity by an agent (e.g., a test agent), or via assessment of a physical interaction of an agent with a domain of an MCL-1 polypeptide relative to interaction of the agent with such a domain in a non-MCL-1 anti-apoptotic multidomain protein (e.g., monitoring of the ability of a test agent to bind to the active site of MCL-1 relative to the ability of the agent to bind to the active site of BCL-2).

As used herein, the term "non-MCL-1 selective BCL-2 family polypeptide inhibitor" refers to an agent that does not possess any greater ability to inhibit MCL-1 activity than to inhibit any other anti-apoptotic multidomain protein (e.g., BCL-2, BCL-XL, BCL-B, BCL-w and BFL-1/A1). Such compounds include "BCL-2 inhibitors," as the term "BCL-2 inhibitor" refers to a therapeutic compound of any type, including small molecule-based, antibody-based, antisense-based, peptide-based, small interfering RNA ("siRNA")-based, or microRNA ("miRNA")-based compounds, that binds to a BCL-2 nucleic acid or polypeptide, and antagonizes the activity of the BCL-2 related nucleic acid or polypeptide. Exemplary BCL-2 inhibitors include N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide ("ABT-263"; see Tse et al., Shoemaker et al. and Lock et al.) and N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide ("ABT-737"), which binds to each of BCL-2, BCL-XL, and BCL-w. The identity and use of exemplary "BCL-2 inhibitor" compounds is disclosed, e.g., in US 2008/0146572, US 2008/0160545 and US 2008/0193943, incorporated herein by reference in their entirety. Structures of other BCL-2 inhibitors are known in the art, and examples are summarized in Walensky, L. D., Cell Death and Differ, 13: 1339, 2006. Specific additional examples include gossypol (a polyphenolic aldehyde that permeates cells and acts as an inhibitor for several dehydrogenase enzymes; 2,2'-bis-(Formyl-1,6,7-trihydroxy-5-isopropyl-3-methylnaphthalene); see, e.g., Tripathki et al.

*Eur J Biochem.* 2004 271(17):3488-502; Conners et al. *Mol Biochem Parasitol.* 2005 142(2):137-48; and Choi et al. *J. Med. Chem.* 2007, 3841-3850) and obatoclax (also referred to as obatoclax mesylate or "GX15-070"; obatoclax is a small molecule indole bipyrrole drug compound; see, e.g., Trudel et al. *Blood.* 2007 109(12):5430-8; O'Brien et al. *Blood.* 2008 Oct. 17).

The term "inflammatory disease or disorder" refers to a fundamental pathogenic process consisting of a dynamic complex of cytologic and histologic reactions that occur in the affected blood vessels and adjacent tissues in response to an injury or abnormal stimulation caused by physical, chemical, or biologic agent. Examples of inflammatory disease within the context of the present invention include rheumatoid arthritis (RA), gout, acute or chronic idiopathic inflammatory arthritis, psoriasis, chronic dermatosis, myositis, demyelinating diseases, chronic obstructive pulmonary disease (COPD), interstitial lung disease, glomerulonephritis, interstitial nephritis, chronic active hepatitis, Crohn's disease, ulcerative colitis, plaque formation in atherosclerosis, multiple sclerosis (MS), degenerative diseases of the joints or nervous system, osteoarthritis, etc.

Examples of apoptosis-mediated diseases or disorders include, but are not limited to, infectious diseases or disorders (Rajalingam et al.; Sly et al.; Cheng et al.; Hasan et al.), immune diseases or disorders, inflammatory diseases or disorders, diseases or disorders which cause liver injury or damage, including hepatocyte injury or damage, e.g. acute and chronic liver injury induced by viral and autoimmune hepatitis, fibrosis, a variety of liver diseases, such as immune related liver diseases, including acute and chronic liver failure, hepatitis, e.g., HBV, HCV, fulminant hepatitis, alcohol induced hepatitis, cholestatic hepatitis, Wilson's disease, and autoimmune hepatitis, and transplant rejection, e.g. liver transplant rejection.

Examples of inflammatory or immune system diseases or disorders, include, but are not limited to sepsis, disseminated intravascular coagulation, viral infection, inflammatory bowel disease, ulcerative colitis, leukocyte adhesion deficiency II syndrome, peritonitis, chronic obstructive pulmonary disease, lung inflammation, asthma, acute appendicitis, nephritis, amyloidosis, chronic bronchitis, sarcoidosis, scleroderma, lupus, polymyositis, Reiter's syndrome, psoriasis, pelvic inflammatory disease, inflammatory breast disease, orbital inflammatory disease, immune deficiency disorders (e.g., HIV, common variable immunodeficiency, congenital X-linked infantile hypogammaglobulinemia, transient hypogammaglobulinemia, selective IgA deficiency, chronic mucocutaneous candidiasis, severe combined immunodeficiency), and autoimmune diseases or disorders.

Examples of autoimmune diseases or disorders include multiple sclerosis, insulin dependent diabetes mellitus, arthritis (e.g., rheumatoid arthritis (RA), juvenile rheumatoid arthritis, osteoarthritis), myesthenia gravis, myocarditis, Guillan-Barre Syndrome, systemic lupus erythematosis, autoimmune thyroiditis, dermatitis, psoriasis, Sjogren's Syndrome, alopecia areata, Crohn's disease, aphthous ulcer, iritis, conjunctivitis, keratoconjunctivitis, ulcerative colitis, allergy, cutaneous lupus erythematosus, scleroderma, vaginitis, proctitis, drug eruptions, leprosy reversal reactions, erythema no do sum lepro sum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves ophthalmopathy, sarcoidosis, cirrhosis, e.g. primary biliary cirrhosis, uveitis posterior, and interstitial lung fibrosis.

As used herein, the term "infectious disease or disorder" is defined as any disease, disorder, or infection which is caused by or related to infection by any infectious agent. For example, infectious diseases or disorders include diseases or disorders caused by or related to infection by a viral infectious agent, bacterial infectious agent, fungal infectious agent, or protozoal infectious agent. Examples of infectious diseases or disorders include, but are not limited to diseases or disorders caused by or related to a viral infectious agent, e.g. HIV, AIDS-related dementia, AIDS-related cancers such as Kaposi's sarcoma, non-Hodgkin's lymphoma, primary central nervous system lymphoma, and invasive squamous cell cancer, AIDS-related diseases or disorders, viral infections including, but not limited to CMV, RSV, HSV, yellow fever virus, dengue fever virus, Japanese encephalitis virus, Murray Valley encephalitis, polioviruis, influenza, rhinovirus, west nile virus, Ebola virus, foot and mouth virus, cytomegalovirus (esp. Human), Rotavirus, Epstein-Barr virus, Varicella Zoster Virus, paramyxoviruses: Respiratory Syncytial virus, parainfluenza virus, measles virus, mumps virus, or influenza virus, human papilloma viruses (for example HPV6, 11, 16, 18 and the like), other sexually transmitted diseases such as, but not limited to hepatitis, e.g. HBV, HCV, HGV, and herpes (HSV-2).

Other examples of apoptosis-mediated diseases and disorders are pulmonary fibrosis, toxic epidermal necrolysis, multiple sclerosis, ulcerative colitis, Sjogren's syndrome, Hashimoto's thyroiditis, and *Helicobacter pylori*-associated chronic gastritis.

In another embodiment, an apoptosis-mediated disease or disorder is mediated by one or more anti-apoptotic genes in which inhibition of expression of the anti-apoptotic gene resulting in increased or enhanced apoptosis would be beneficial, e.g. cancer.

Apoptosis-mediated diseases and disorders also include diseases or disorders which are related to anti-apoptotic genes, including, but not limited to, cellular proliferation, growth, differentiation, or migration disorders and diseases or disorders where there is decreased apoptosis or cell death. Such disorders include cancer, e.g. carcinoma, sarcoma, lymphoma or leukemia, examples of which include, but are not limited to, ovarian, lung, breast, endometrial, uterine, hepatic, gastrointestinal, prostate, colorectal, liver, and brain cancer, tumor angiogenesis and metastasis; skeletal dysplasia; and hematopoietic and/or myeloproliferative disorders. The terms "neoplasia," "hyperplasia," and "tumor" are often commonly referred to as "cancer," which is a general name for more than 100 diseases that are characterized by uncontrolled, abnormal growth of cells. As used herein, a "tumor" also includes a normal, benign, or malignant mass of tissue.

Subjects with "refractory cancer" or "refractory lymphoma" are those who have failed to achieve complete remission on their first course of chemotherapy, or to patients who have failed to achieve complete or partial remission on subsequent chemotherapy. "Primary refractory" patients are those who have never achieved complete remission even at first treatment.

A "relapsed cancer" or lymphoma refers to a cancer or lymphoma that has recurred following prior complete or partial remission in response to a prior treatment. Recurrence can be defined in any way, including a reappearance or re-growth of a tumor as detected by clinical, radiological, or biochemical assays, or by an increased level of a cancer marker. Prior treatments can include, but are not limited to, chemotherapy, radiation therapy, and bone marrow transplantation.

As used herein, the term "disease of cell cycle regulation" refers to a disease or disorder for which the underlying cause is attributable to abnormal regulation of the cell cycle. Exemplary diseases of cell cycle regulation include cancer, such as Hodgkins disease and B cell chronic lymphocytic leukaemia, as well as cancers caused by mutation of cell cycle inhibitors (e.g., tumor suppressor proteins) such as retinoblastoma protein (RB), p53, etc.

The term "cell cycle arrest" includes cytostasis or other arrest of cell growth (whether cytotoxic or not) and cell senescence.

The term "autophagy" includes a catabolic process in which the cell degrade's its own components to as an adaptive mechanism for survival or as a manifestation of a form of programmed cell death.

The term "splicing" includes RNA splicing, in which the cell alternately splices RNA resulting in an altered RNA transcript.

As used herein, "changed as compared to a control reference sample" is understood as having a level or activity of an analyte, or in a whole organism change of physical characteristics or signs or symptoms of a disease, to be detected at a level that is statistically different than a sample from a normal, untreated, or control sample. Methods to select and test control samples are within the ability of those in the art. Control samples typically include a cell or an animal of the same type that has not been contacted with an active agent or been subjected to a particular treatment, and has optionally been contacted with a carrier or subjected to a sham treatment. Control samples also include a cell or an animal not subjected to an agent or treatment to induce a specific disease or condition.

The phrase "in combination with" is intended to refer to all forms of administration that provide a first agent together with a second agent, such as a second inhibitory nucleic acid molecule or a chemotherapeutic agent, where the two are administered concurrently or sequentially in any order. For two or more agents to be administered in combination with each other, the agents need not be administered simultaneously or in the same formulation. Agents administered in combination with each other simultaneously present or have biological activity in the subject to which the agents are delivered. Determination of the presence of a agent in a subject can be readily determined by empirical monitoring or by calculations using known pharmacokinetic properties of the agents.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the object to be detected. The amount detected can be none or below the level of detection.

By "an effective amount" is meant the amount of an agent required to ameliorate the symptoms of a disease relative to an untreated patient. The effective amount of active agent(s) used to practice the present invention for therapeutic treatment of a neoplasia varies depending upon the manner of administration, the age, body weight, and general health of the subject. Ultimately, the attending physician or veterinarian will decide the appropriate amount and dosage regimen. Such amount is referred to as an "effective" amount.

As used herein, "isolated" or "purified" when used in reference to a polypeptide means that a naturally polypeptide has been removed from its normal physiological environment (e.g., protein isolated from plasma or tissue) or is synthesized in a non-natural environment (e.g., artificially synthesized in a heterologous system). Thus, an "isolated" or "purified" polypeptide can be in a cell-free solution or placed in a different cellular environment (e.g., expressed in a heterologous cell type). The term "purified" does not imply that the polypeptide or cell is the only polypeptide or cell present, but that it is essentially free (about 80-90%, or about 90-95%, up to 99-100% pure) of cellular or organismal material naturally associated with it, and thus is distinguished from naturally occurring polypeptide. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition.

By "obtaining" is meant synthesizing, purchasing, or otherwise acquiring the inhibitory nucleic acid molecule. "Providing," refers to obtaining, by for example, buying or making the, e.g., cells, polypeptide, drug, polynucleotide, probe, and the like. The material provided may be made by any known or later developed biochemical or other technique.

The term "pharmaceutically-acceptable excipient" as used herein means one or more compatible solid or liquid filler, diluents or encapsulating substances that are suitable for administration into a human.

A "sample" as used herein refers to a biological material that is isolated from its environment (e.g., blood or tissue from an animal, cells, or conditioned media from tissue culture) and is suspected of containing, or known to contain an analyte or other desired material. A sample can also be a partially purified fraction of a tissue or bodily fluid, e.g., from a subject having a specific disease or condition. A reference sample can be a "normal" sample, from a donor not having the disease or condition. A reference sample can also be from an untreated donor or cell culture not treated with an active agent (e.g., no treatment or administration of vehicle only) or not subjected to conditions to induce a disease state. A reference sample can also be taken at a "zero time point" prior to contacting the cell with the agent to be tested.

By "specifically binds" is meant a molecule that recognizes and binds another molecule, e.g., protein or nucleic acid molecule of the invention, but which does not substantially recognize and bind other molecules in a sample, for example, a biological sample, which naturally includes a protein of the invention. Preferably, a first molecule that specifically binds a second molecule binds the second molecule with at least 5-, 10-, 15-, 20-, 25-, 50-75, 100-, 500-, 1000-, 5000-, or 10,000-fold preference over a non-specific binding partner (e.g., BSA for proteins, random nucleic acid sequence) or over a structurally similar protein.

Ranges provided herein are understood to be shorthand for all of the values within the range. For example, a range of 1 to 50 is understood to include any number, combination of numbers, or sub-range from the group including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

"At least" a particular value is understood to mean that value or more. For example, "at least 2" is understood to be the same as "2 or more" i.e., 2, 3, 4, 5, 6, 7, 8, 9, 10, 11, 12, 13, 14, 15, etc.

"Less than" or "up to" and the like is understood as the range from zero up to and including the value provided. For example, "less than 10" or "up to 10" is understood as 0, 1, 2, 3, 4, 5, 6, 7, 8, 9, or 10.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless obvious from context, all numerical values provided herein can be understood to be modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

All references, patents, patent applications, and Accession Numbers as of the filing date of the priority application referred to herein are specifically incorporated by reference.

DESCRIPTION

The development of selective inhibitors for discrete anti-apoptotic BCL-2 family proteins implicated in pathologic cell survival remains a formidable but pressing challenge. Precisely tailored compounds would serve as both molecular probes and targeted therapies to respectively study and treat human diseases driven by specific anti-apoptotic blockades. We previously applied hydrocarbon stapling to transform unfolded BID, BAD, and BIM BH3 peptides into protease-resistant and cell-permeable α-helices that engage and modulate their intracellular targets for both therapeutic benefit (Danial et al., *Nat Med* 14, 144. 2008; Walensky et al., *Science* 305, 1466. 2004, both incorporated by reference) and mechanistic analysis (Gavathiotis et al., *Nature* 455, 1076. 2008; Walensky et al., *Mol Cell* 24, 199. 2006, both incorporated by reference). MCL-1 has emerged as a major resistance factor in a broad range of human cancers. By screening a library of stabilized alpha-helix of BCL-2 domains (SAHBs), we determined that the BH3 helix of MCL-1 itself, as well as other SAHBs from other BCL-2 family proteins, are potent and exclusive MCL-1 inhibitor. X-ray crystallography and mutagenesis studies defined the critical determinants for MCL-1 BH3 engagement of the MCL-1 binding groove. MCL-1 SAHB directly targets MCL-1, neutralizes its inhibitory interaction with pro-apoptotic BAK, and sensitizes MCL-1-dependent cancer cells to caspase-dependent apoptosis. Thus, by leveraging Nature's solution to ligand selectivity, we generated a cell-permeable MCL-1-specific agent to define the structural and functional features of targeted MCL-1 inhibition.

A series of anti-apoptotic proteins including BCL-2, BCL-XL, BCL-w, MCL-1, and BFL1/A1 promote cellular survival by trapping the critical apoptosis-inducing BCL-2 homology domain 3 (BH3) α-helix of pro-apoptotic BCL-2 family members (Sattler et al., *Science* 275, 983. 1997). Cancer cells exploit this physiologic survival mechanism through anti-apoptotic protein overexpression, establishing an apoptotic blockade that secures their immortality.

Anti-apoptotic proteins contain a hydrophobic binding pocket on their surface that engages BH3 α-helices (Sattler et al., 1997; Muchmore et al., *Nature* 381, 335. 1996). Because Nature's solution to anti-apoptotic targeting involves selective interactions between BH3 death domains and anti-apoptotic pockets (Chen et al., *Mol Cell* 17, 393. 2005; Zhai et al., *J Biol Chem* 283, 9580. 2008), molecular mimicry of the BH3 α-helix has formed the basis for developing small molecule inhibitors of anti-apoptotic proteins. Promising compounds undergoing clinical evaluation, such as ABT-263 (Tse et al., *Cancer Res* 68, 3421. 2008), obatoclax (Nguyen et al., *Proc Natl Acad Sci USA* 104, 19512. 2007), and AT-101 (Wang et al., *J Med Chem* 49, 6139. 2006), each target three or more anti-apoptotic proteins (all incorporated by reference). The development of precise inhibitors that target individual anti-apoptotic proteins remains a significant challenge due to the subtle differences among BH3-binding pockets. Reminiscent of the long-term goals in kinase therapeutics, anti-apoptotic inhibitors with tailored specificity would provide finely-tuned therapies to treat distinct diseases while potentially avoiding unwanted side-effects. Compounds with such specificity are provided herein. In addition, such compounds would serve as invaluable research tools to dissect the differential biological functions of anti-apoptotic proteins.

The specificity of anti-apoptotic proteins for BH3 domains is conferred by the topography of the canonical binding groove and the distinctive amino acid composition of the interacting BH3 helix. Whereas some BH3 domains, such as that of pro-apoptotic BIM, can tightly engage all anti-apoptotic pockets, others are more selective like the BAD BH3 that binds BCL-2, BCL-XL, and BCL-w and the NOXA BH3 that targets MCL-1 and BFL-1/A1 (Chen et al., *Mol Cell* 17, 393. 2005). The differential binding capacity of BH3 domains and their mimetics is clinically relevant, as exemplified by the close relationship between inhibitor binding spectrum and biological activity. For example, ABT-737, the prototype small molecule BH3 mimetic modeled after the BH3 domain of BAD, was designed to specifically target BCL-2 and BCL-XL, and induces apoptosis in select cancers that are driven by these proteins (Oltersdorf et al., *Nature* 435, 677. 2005). This demonstrates the difficulty of preparing specific inhibitors for the desired target. Further, ABT-737 fails to show efficacy against cancer cells that overexpress MCL-1, as this anti-apoptotic lies outside the molecules' binding spectrum (Konopleva et al., *Cancer Cell* 10, 375. 2006; Delft et al., *Cancer Cell* 10, 389. 2006). In an effort to overcome the challenge of designing precision small molecules to selectively target interaction surfaces that are comparatively large and more complex, we investigated whether Nature's BH3 domains could provide a pharmacologic solution to anti-apoptotic specificity.

We chose MCL-1 as the template for this study because of its emerging role as a critical resistance factor in human cancer. MCL-1 overexpression has been linked to the pathogenesis of a variety of refractory cancers, including multiple myeloma, acute myeloid leukemia, melanoma, and poor prognosis breast cancer; therefore, it is expected that the MCL-1 inhibitors provided herein, particularly the MCL-1 specific inhibitors will be useful for the treatment of such cancers. MCL-1 exerts its pro-survival activity at the mitochondrial outermembrane where it neutralizes pro-apoptotic proteins such as NOXA, PUMA, BIM, and BAK. The critical role of MCL-1 in selective apoptotic resistance has been highlighted by the sensitizing effects of small interfering RNAs that downregulate MCL-1 protein levels (Lin et al., *Oncogene* 26, 3972. 2007; Taniai et al., *Cancer Res* 64, 3517. 2004, both incorporated herein by reference). Given the clear therapeutic rationale for targeting MCL-1, we sought to develop a selective MCL-1 inhibitor for biological testing. As demonstrated herein, the specific MCL-1 inhibitors of the instant application show similar effects as siRNAs that downregulate MCL-1, demonstrating that the MCL-1 inhibitors of the instant invention can have a therapeutic effect in MCL-1 related diseases, particularly cancer.

BCL-2 proteins, like many protein families, are comprised of numerous members sharing a high percentage of sequence identity and functional homology, making the development of specific inhibitors difficult. It is the subtle differences among these homologous proteins, however, that give rise to their unique interactions and spectra of activity. When implicated in pathologic protein interactions, it may be desirable to neutralize all anti-apoptotic family members or a discrete subset, with the drug profile of choice dictated by the nature and severity of the disease. In the case of targeting anti-apoptotic BCL-2 family proteins that cause uncontrolled cell survival, an ideal pharmacologic toolbox would contain agents that target individual, subsets, and all members. Achieving this goal requires careful structural dissection of both the unique and common elements of BH3 interactions with anti-apoptotic targets. Guided by the natural BH3 binding selectivities, we have identified a potent and exclusive inhibitor of MCL-1 based on the peptide sequence of its own BH3 domain. We find that targeting MCL-1 disrupts its capacity to bind and sequester pro-apoptotic partners. By identifying critical binding and specificity determinants for selective MCL-1 inhibition, the structure-function data provide a blueprint for the development of novel therapeutics to reactivate apoptosis in diseases driven by pathologic MCL-1-mediated cell survival.

BCL-2 Family Proteins as Apoptotic Regulators

The BCL-2 family includes both pro- and anti-apoptotic proteins, which form a complex network of checks and balances that dictate cell fate (Danial and Korsmeyer, 2004) (FIG. 1A). The family is structurally defined by the presence of up to four conserved "BCL-2 homology" (BH) domains, all of which include α-helical segments (Adams and Cory, 1998; Reed, 1998) (FIG. 1B). Anti-apoptotic proteins display sequence conservation in all BH domains, whereas pro-apoptotic proteins are divided into "multi-BH domain" members and "BH3-only" members that only display sequence similarity to the BH3 α-helical domain. The "BH3-only" subgroup is diverse and transmits pro-death signals arising from disparate stimuli to the core apoptotic machinery located at the mitochondrion. Depending upon the nature of apoptotic stimuli and cellular context, the BH3-only protein's death signal will either be neutralized by anti-apoptotic proteins or delivered, directly or indirectly, to the mitochondrial executioners BAX and BAK. When activated, these pro-apoptotic multi-BH domain members induce permeabilization of the outer mitochondrial membrane, enabling released mitochondrial factors to activate caspases, which irreversibly execute the death program (Green, 2005).

As stated above, members of the evolutionarily conserved BCL-2 family are important regulators of apoptotic cell death and survival. The proteins BCL-2, BCL-$X_L$, BCL-W, BFL-1/A1, BCL-B, and MCL-1 are death antagonists while BAX, BAK, BAD, BCL-XS, BID, BIM, and BIK, among others, are death agonists (Kroemer et al., Nature Med. 6:614 20 (1997)).

The BCL-2 family is defined by the presence of up to four conserved "BCL-2 homology" (BH) domains designated BH1, BH2, BH3, and BH4, all of which include alpha-helical segments (Chittenden et al. 1995 EMBO 14:5589; Wang et al. 1996 Genes Dev. 10:2859) (FIG. 1). Anti-apoptotic proteins, such as BCL-2 and BCL-XL, display sequence conservation in all BH domains. Pro-apoptotic proteins are divided into "multidomain" members (e.g. BAK, BAX, BOK), which possess homology in the BH1, BH2, and BH3 domains, and the "BH3-domain only" members (e.g. BID, BAD, BIM, BIK, NOXA, PUMA), that contain sequence homology exclusively in the BH3 amphipathic alpha-helical segment. BCL-2 family members have the capacity to form homo- and heterodimers, suggesting that competitive binding and the ratio between pro- and anti-apoptotic protein levels dictates susceptibility to death stimuli. Anti-apoptotic proteins function to protect cells from pro-apoptotic excess, i.e., excessive programmed cell death. In certain cell types, death signals received at the plasma membrane trigger apoptosis via a mitochondrial pathway. The mitochondria can serve as a gatekeeper of cell death by sequestering cytochrome c, a critical component of a cytosolic complex which activates caspase 9, leading to fatal downstream proteolytic events. Multidomain proteins such as BCL-2/BCL-XL and BAK/BAX play dueling roles of guardian and executioner at the mitochondrial membrane, with their activities further regulated by upstream BH3-only members of the BCL-2 family. For example, BID is a member of the "BH3-domain only" subset of pro-apoptotic proteins, and transmits death signals received at the plasma membrane to effector pro-apoptotic proteins at the mitochondrial membrane. Select BH3-only members, such as BID and BIM, have been termed "activators" (Letai, A., et al. *Cancer Cell* 2, 183. 2002), and have the unique capability of interacting with both pro- and anti-apoptotic proteins (Walensky *Mol Cell* 24, 199. 2006). Upon caspase 8 activation, BID is cleaved and the truncated adduct, tBID, triggers cytochrome c release and mitochondrial apoptosis through engagement of BCL-2 family proteins.

Deletion and mutagenesis studies determined that the amphipathic alpha-helical BH3 segment of pro-apoptotic family members functions as a death domain and thus represents a critical structural motif for interacting with multidomain apoptotic proteins. Structural studies have demonstrated that the BH3 helix interacts with anti-apoptotic proteins by inserting into a hydrophobic groove formed by the interface of BH1, 2 and 3 domains. tBID and BIM can be bound and sequestered by anti-apoptotic proteins (e.g., BCL-2 and BCL-$X_L$) and can trigger activation of the pro-apoptotic proteins BAX and BAK, leading to cytochrome c release and a mitochondrial apoptosis program.

BCL-2-related ovarian killer (BOK) is the third member of the pro-apoptotic multidomain subgroup and is also bound by activator SAHB ligands, such as BID and BIM SAHBs. BOK was cloned from an ovarian cDNA library and found to be highly expressed in ovary, uterus, and testis. BOK mRNA species have since been identified in a broader distribution of tissues, including heart, spleen, liver, colon, lung, intestine, thyroid gland, adrenal, pancreas, and bone marrow, and select cancer cell lines.

The first X-ray and NMR structure of a BCL-2 family protein (BCL-$X_L$) was reported in 1996. BCL-$X_L$ consists of eight alpha-helices, two of which form a central hydrophobic core similar to the membrane insertion domains of pore-forming Diphtheria toxin and colicins. This structural analogy led to experimental confirmation that BCL-2 family members can mediate pore-formation in liposomal and mitochondrial systems, an activity that is dependent upon core helices 5 and 6.

On the pro-apoptotic side, NMR structures of BH3-only BID and multidomain pro-apoptotic BAX disclosed similarities between the proponents and opponents of cell death. BID and BAX likewise possess two central core helices that are surrounded by 6 or 7 amphipathic helices, respectively. The amino terminal portions of BID and BAX contain unstructured loops, as do select anti-apoptotic proteins such as BCL-2 and BCL-$X_L$.

The structures of many of the BCL-2 family polypeptides, including, BCL-$X_L$, BCL-2, BID, BAX, BCL-w, MCL-1, BAX are known in the art and readily accessible. For example, BCL-2 family polypeptides can be obtained from the Protein Data Bank ("PDB") (Research Collaboratory for Structural Bioinformatics; http://www.rcsb.org). For example, known BCL-2 family structural co-ordinates include BAX (PDB ID No. 1f16), BAK (PDB ID No. 2ims), BCL-2 (PDB ID No. 1g5m), BCL-XL (PDB ID No. 1lxl), in addition to that associated with this invention: BIM BH3-BAX (PDB ID No. 2k7w), as well as others known in the art.

Therapeutic Targeting of Anti-Apoptotic Proteins

Figure 2:
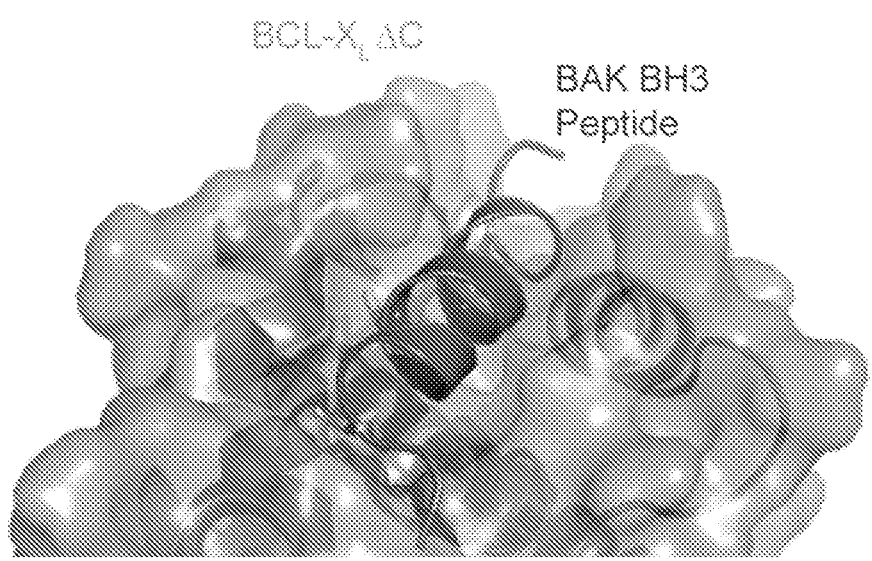
FIG. 2 shows how the BH3-binding pocket of an anti-apoptotic protein binds and sequesters a death helix.

Cancer cells overexpress anti-apoptotic proteins to repress pro-apoptotic proteins, and thereby mount an apoptotic blockade that ensures their survival (FIG. 2). Pharmacologic disruption of specific BCL-2 family protein interactions can induce apoptosis in cancer cells. For example, ABT-737, a small molecule BH3 mimetic modeled after the BH3-only protein BAD, was designed to specifically target BCL-2 and BCL-$X_L$ (Oltersdorf et al., 2005) and induces apoptosis in select cancers that are driven by these proteins (Kline et al., 2007; Konopleva et al., 2006; van Delft et al., 2006). ABT-263 (Lock et al., 2008; Shoemaker et al., 2008; Tse et al., 2008), an oral form of ABT-737, is currently being evaluated in phase I/IIa cancer trials. The ABT compounds fail to show efficacy against cancer cells that overexpress MCL-1, as this anti-apoptotic lies outside their binding spectrum (Deng et al., 2007; Konopleva et al., 2006; van Delft et al., 2006). Further references describing the connection between MCL-1 and various forms of cancer (e.g., AML, breast and multiple myeloma) include Darenne et al., Zhang et al., Lin et al., Kim et al., Schulze-Bergkamen et al., Hussain et al. and Thallinger et al. (complete references below).

Stapled BH3 Peptides as Selective MCL-1 Inhibitors

Figure 3:
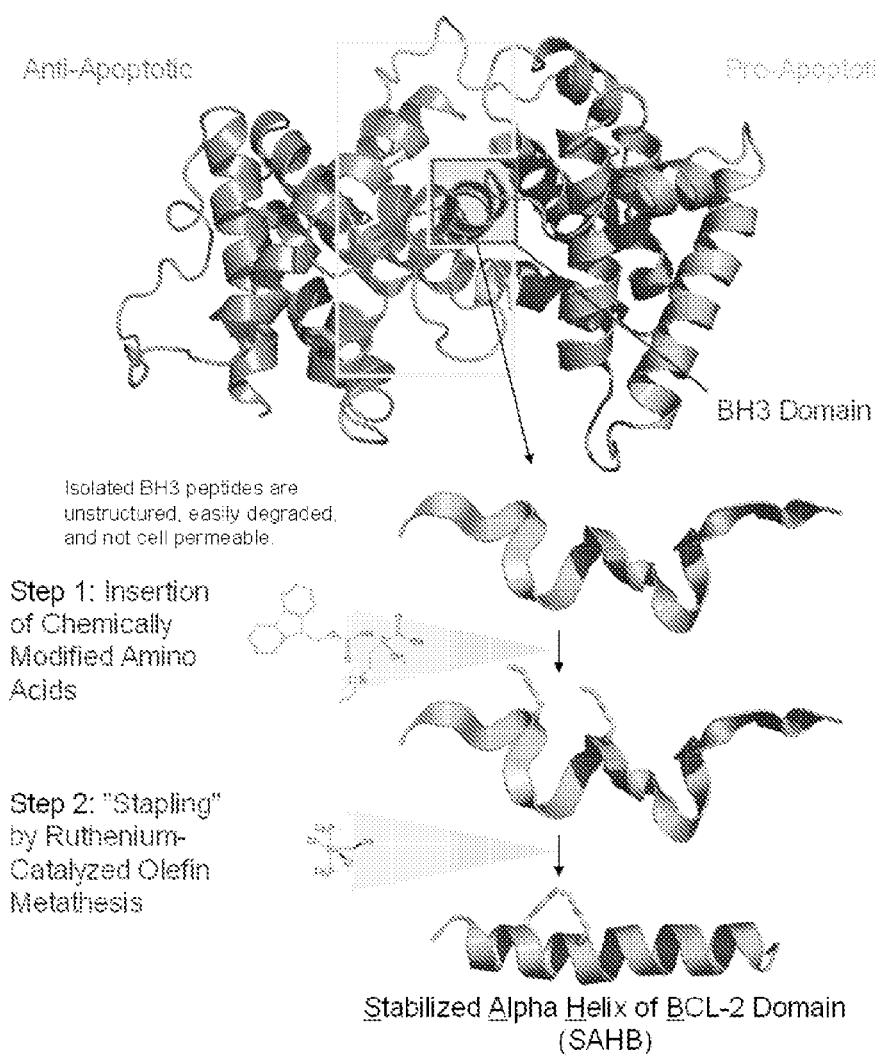
FIG. 3 shows how the bioactive BH3 helix can be reconstituted by hydrocarbon stapling to yield a helical, protease resistant, and cell permeable compound capable of targeting BCL-2 family proteins.

Stabilized Alpha-Helices of BCL-2 domains, or SAHBs, were developed to investigate and modulate BCL-2 family interactions in vitro and in vivo (FIG. 3). For example, it was demonstrated that an all-hydrocarbon crosslink, inserted into native pro-apoptotic BID BH3 peptide sequence, successfully (1) restored and stabilized α-helical structure, (2) enhanced peptide half-life, (3) conferred cellular permeability, (4) specifically bound the target apoptotic proteins, and (5) reactivated cellular apoptosis in a leukemia xenograft model (Walensky et al., 2004). SAHBs have since been used to dissect and modulate discrete BCL-2 family protein interactions (Danial et al., 2008; Gavathiotis et al., 2008; Walensky et al., 2006). As described herein, a series of stapled BCL-2 family peptide helices have been identified that target the survival protein MCL-1 with high affinity and unprecedented selectivity. The MCL-1 inhibitor SAHBs target the canonical BH3 groove of MCL-1, displacing the MCL-1/BAK interaction in vitro and in situ, and sensitizing MCL-1 dependent cancer cells to mitochondrial apoptosis.

MCL-1 Active Site

The present invention is based, at least in part, on the discovery that hydrocarbon-stapled and thus structurally-reinforced BH3 polypeptides, such as MCL-1 SAHB and NOXA SAHB, bind the active site on MCL-1 polypeptides, resulting in inhibition of the anti-apoptotic (survival) activity of MCL-1. The present studies also have provided structural information that has enabled identification of the region of the MCL-1 polypeptide involved in the molecular interaction with such inhibitory SAHB agents (e.g., NOXA stabilized alpha-helix of BCL-2 family BH3 domain (SAHB) polypeptide, BOK SAHB peptide, MCL-1 SAHB peptide, wild type or tailored BIM SAHB or BAK SAHB peptide, Mule SAHB peptide), and thus inhibition of this polypeptide, thereby providing methods for identifying other specific modulators of MCL-1, with such methods of identifying specific inhibitory and/or binding agents also applicable to other BCL-2 family polypeptides (or other class of polypeptides) containing a corresponding active site.

The polypeptides of the present invention may have stabilized (e.g., cross-linked) alpha helical domains. In certain embodiments, the polypeptides are hydrocarbon-stapled. Hydrocarbon stapling is described in U.S. Publication No. 2005/0250680, which is herein incorporated by reference in its entirety.

The hydrocarbon stapled polypeptides include one or more tethers (linkages) between two non-natural amino acids, which tether significantly enhances the alpha helical secondary structure of the polypeptide. Generally, the tether extends across the length of one or two helical turns (i.e., about 3.4 or about 7 amino acids). Accordingly, amino acids positioned at i and i+3; i and i+4; or i and i+7 are ideal candidates for chemical modification and cross-linking. Thus, for example, where a peptide has the sequence . . . X1, X2, X3, X4, X5, X6, X7, X8, X9 . . . , cross-links between X1 and X4, or between X1 and X5, or between X1 and X8 are useful as are cross-links between Xa2 and X5, or between X2 and X6, or between X2 and X9, etc. The use of multiple cross-links (e.g., 2, 3, 4 or more) is also contemplated. The use of multiple cross-links is very effective at stabilizing and optimizing the peptide, especially with increasing peptide length. Thus, the invention encompasses the incorporation of more than one crosslink within the polypeptide sequence to either further stabilize the sequence or facilitate the structural stabilization, proteolytic resistance, acid stability, thermal stability, and biological activity enhancement of longer polypeptide stretches. The process of hydrocarbon stapling is fully described, for example, in U.S. Patent Publication No. US2005/0250680, which is herein incorporated by reference in its entirety.

In one embodiment, a SAHB polypeptide has the formula (I),

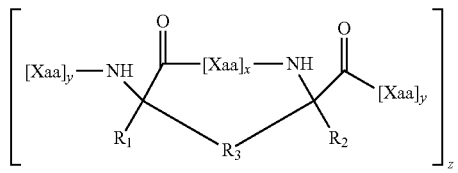

wherein;

each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkyl, alkenyl, alkynyl; $[R_4—K—R_4]_n$; each of which is substituted with 0-6 $R_5$;

$R_4$ is alkyl, alkenyl, or alkynyl;

$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

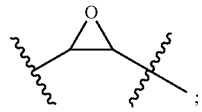 [SMILES: *C1OC1*]

$R_6$ is H, alkyl, or a therapeutic agent;
n is an integer from 1-4;
x is an integer from 2-10;
each y is independently an integer from 0-100;
z is an integer from 1-10 (e.g., 1, 2, 3, 4, 5, 6, 7, 8, 9, 10); and each Xaa is independently an amino acid. The SAHB polypeptides may include an amino acid sequence described herein.

The tether can include an alkyl, alkenyl, or alkynyl moiety (e.g., $C_5$, $C_8$ or $C_{11}$ alkyl or a $C_5$, $C_8$ or $C_{11}$ alkenyl, or $C_5$, $C_8$ or $C_{11}$ alkynyl). The tethered amino acid can be alpha disubstituted (e.g., $C_1$-$C_3$ or methyl).

In some instances, x is 2, 3, or 6.

In some instances, each y is independently an integer between 3 and 15.

In some instances each y is independently an integer between 1 and 15.

In some instances, $R_1$ and $R_2$ are each independently H or $C_1$-$C_6$ alkyl.

In some instances, $R_1$ and $R_2$ are each independently $C_1$-$C_3$ alkyl.

In some instances, at least one of $R_1$ and $R_2$ are methyl. For example $R_1$ and $R_2$ are both methyl.

In some instances $R_3$ is alkyl (e.g., $C_8$ alkyl) and x is 3.

In some instances, $R_3$ is $C_{11}$ alkyl and x is 6.

In some instances, $R_3$ is alkenyl (e.g., $C_8$ alkenyl) and x is 3.

In some instances x is 6 and $R_3$ is $C_{11}$ alkenyl.

In some instances, $R_3$ is a straight chain alkyl, alkenyl, or alkynyl.

In some instances $R_3$ is —$CH_2$—$CH_2$—$CH_2$—CH=CH—$CH_2$—$CH_2$—$CH_2$—.

In certain embodiments the two alpha, alpha disubstituted stereocenters are both in the R configuration or S configuration (e.g., i, i+4 cross-link), or one stereocenter is R and the other is S (e.g., i, i+7 cross-link). Thus, where formula I is depicted as

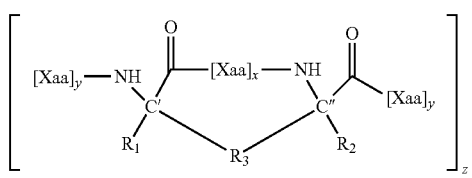

the C' and C" disubstituted stereocenters can both be in the R configuration or they can both be in the S configuration, for example when X is 3. When x is 6, the C' disubstituted stereocenter is in the R configuration and the C" disubstituted stereocenter is in the S configuration. The $R_3$ double bond may be in the E or Z stereochemical configuration.

In some instances $R_3$ is $[R_4—K—R_4]_n$; and $R_4$ is a straight chain alkyl, alkenyl, or alkynyl.

In some embodiments the SAHB polypeptide comprises at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, or more contiguous amino acids of a BH3 domain. Each [Xaa]y is a peptide that can independently comprise at least 5, 6, 7, 8, 9, 10, 11, 12, 13, 14, 15, 16, 17, 18, 19, 20, 25 or more contiguous amino acids of a BH3 domain. $[Xaa]_x$ is a peptide that can comprise 3 or 6 contiguous amino acids of acids of a BH3 domain.

The SAHB polypeptide can comprise 3, 4, 5, 6, 7, 8, 9, 10, 11, 12, 13, 14, 15, 16, 17, 18, 19, 20, 25, 30, 35, 40, 45, 50 contiguous amino acids of acids of a BH3 domain, wherein two amino acids that are separated by two, three, or six amino acids are replaced by amino acid substitutes that are linked via $R_3$. Thus, at least two amino acids can be replaced by tethered amino acids or tethered amino acid substitutes. Thus, where formula (I) is depicted as

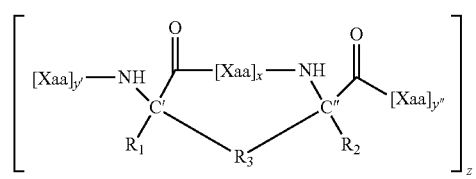

$[Xaa]_{y'}$, and $[Xaa]_{y''}$ can each comprise contiguous polypeptide sequences from the same or different BH3 domains.

The invention features cross-linked polypeptides comprising 10 (11, 12, 13, 14, 15, 16, 17, 18, 19, 20, 21, 22, 23, 24, 25, 30, 35, 40, 45, 50 or more) contiguous amino acids of a BH3 domain, wherein the alpha carbons of two amino acids that are separated by two, three, or six amino acids are linked via $R_3$, one of the two alpha carbons is substituted by $R_1$ and the other is substituted by $R_2$ and each is linked via peptide bonds to additional amino acids.

In another embodiment, the SAHB polypeptides of the invention have the formula (II),

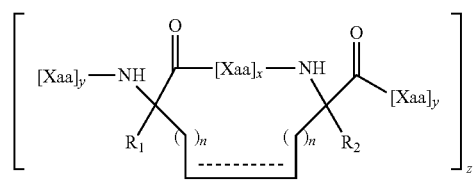

wherein
each $R_1$ and $R_2$ are independently H, alkyl, alkenyl, alkynyl, arylalkyl, cycloalkylalkyl; heteroarylalkyl; or heterocyclylalkyl;
each n is independently an integer from 1-15;
x is 2, 3, or 6
each y is independently an integer from 0-100;
z is an integer from 1-10 (e.g., 1, 2, 3, 4, 5, 6, 7, 8, 9, 10);
each Xaa is independently an amino acid.

The modified polypeptide forms an alpha-helix and can have an amino acid sequence which is 30% or more identical to an amino acid sequence disclosed herein.

In still another embodiment, the SAHB polypeptides of the invention have the formula (III),

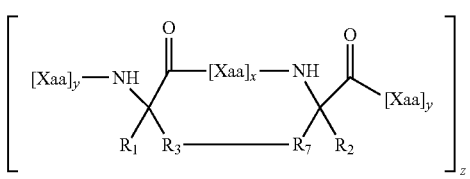

wherein;
each $R_1$ and $R_2$ are independently H, alkyl, alkenyl, alkynyl, arylalkyl, cycloalkylalkyl, heteroarylalkyl, or heterocyclylalkyl;
$R_3$ is alkyl, alkenyl, alkynyl; $[R_4—K—R_4]_n$ or a naturally occurring amino acid side chain; each of which is substituted with 0-6 $R_5$;
$R_4$ is alkyl, alkenyl, or alkynyl;
$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;
K is O, S, SO, $SO_2$, CO, $CO_2$, $CONR_6$, or

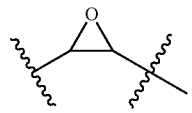 [SMILES: *C1OC1*]

$R_6$ is H, alkyl, or a therapeutic agent;
$R_7$ is alkyl, alkenyl, alkynyl; $[R_4—K—R_4]_n$ or an naturally occurring amino acid side chain;
each of which is substituted with 0-6 $R_5$;
n is an integer from 1-4;
x is an integer from 2-10;
each y is independently an integer from 0-100;
z is an integer from 1-10 (e.g., 1, 2, 3, 4, 5, 6, 7, 8, 9, 10); and
each Xaa is independently an amino acid;

The polypeptide forms and alpha-helix and includes an amino acid sequence which is about 30% or more identical to an amino acid sequence described herein.

While hydrocarbon tethers have been described, other tethers are also envisioned. For example, the tether can include one or more of an ether, thioether, ester, amine, or amide, or triazole moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids and also used in combination to install multiple tethers.

As can be appreciated by the skilled artisan, methods of synthesizing the compounds of the described herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

As will be appreciated by the skilled artisan, insights derived from those sequences that bind MCL-1 (both pan-binders and selective binders) has been be used to define the essential binding residues for MCL-1 targeting. Such insights have, in turn, been used to develop optimized binders, via methods such as mutagenesis, incorporation of other non-natural amino acids, etc.

Drug Design

As will be appreciated by the skilled artisan, computer-based drug design methods can be used to develop small molecules that mimic the MCL-1 specific binding elements of SAHBs, such as those identified herein to specifically bind MCL-1, resulting in modulation of MCL-1 activity.

Specifically, identification of the active site of MCL-1, and of specific SAHB agents capable of selectively binding to the MCL-1 BH3 domain, aids the development and identification of compounds which are capable of modulating MCL-1 and other BCL-2 family polypeptides having a corresponding active site. For example, using this information, a three-dimensional computer generated interaction template of MCL-1 can be generated by one of ordinary skill in the art and used to design activators and inhibitors specific for the MCL-1 active site. In another embodiment, one of ordinary skill in the art can apply the MCL-1 active site to identify corresponding active sites in other BCL-2 family members, or in other non-BCL-2 family members possessing conserved domains, e.g., a BH3 domain of the MULE protein. This information may then be used to identify/develop compounds capable of modulating the other BCL-2 family polypeptides and/or polypeptides possessing domains that are conserved with BCL-2 family polypeptides.

Determination of the three dimensional structure of the MCL-1 polypeptide and specifically the active site is critical to the rational identification and/or design of agents that may act as modulators of MCL-1 polypeptide activity. This is advantageous over conventional drug assay techniques, in which the only way to identify such an agent is to screen thousands of test compounds until an agent having the desired inhibitory effect on a target compound is identified. Necessarily, such conventional screening methods are expensive, time consuming, and do not elucidate the method of action of the identified agent on the target compound. Using such a three dimensional structure, researchers identify putative binding sites and then identify or design agents to interact with these binding sites. These agents are then screened for a modulating effect upon the target molecule. In this manner, not only are the number of agents to be screened for the desired activity greatly reduced, but the mechanism of action on the target compound is better understood.

It is contemplated that identification of the MCL-1 active site can be used to computationally screen small molecule databases for compounds that can bind in whole, or in part, to one or more of the regions of the MCL-1 polypeptide's active site. In one embodiment of this method, the quality or fit of the compound identified to the regions of the active site can be judged either by shape complementarity or by estimated interaction energy (Meng et al., J. Comp. Chem. 13:505-524, 1992).

In a further embodiment, potential modulators that can be analyzed according to the methods of the invention can be obtained using any of the numerous approaches in combinatorial library methods known in the art. In one embodiment, potential modulators are first identified for pro-apoptotic or anti-apoptotic activity using the in vitro assays (eg. fluorescence polarization) described herein or known in the art. Once potential modulators are identified, and their structures determined, further optimization can be carried out by computational analyses using the structure information of the MCL-1 active site described herein. In another embodiment, a potential modulator is first identified in a screen using an interaction template developed from the structure coordinates of the MCL-1 active site and further subjected to optimization by additional computational analyses. Alternatively, further optimization can be carried out by determining the NMR structural coordinates of co-complexes of the potential modulator and the MCL-1 active site using the methods described herein.

Various combinatorial libraries that can be used in the methods of the invention include, but are not limited to: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des.* 12:145).

In one embodiment, the library of compounds is a digital library. The binding interaction is performed with a database searching program which is capable of scanning a database of small molecules of known three-dimensional structure for candidates which fit into the active site. Suitable software programs include CATALYST (Molecular Simulations Inc., San Diego, Calif.), UNITY (Tripos Inc., St Louis, Mo.), FLEXX (Rarey et al., *J. Mol. Biol.* 261: 470-489 (1996)), CHEM-3-DBS (Oxford Molecular Group, Oxford, UK), DOCK (Kuntz et al., *J. Mol. Biol.* 161: 269-288 (1982)), and MACCS-3-D (MDL Information Systems Inc., San Leandro, Calif.) and LUDI (Boehm, *J. Comp. Aid. Mol. Des.* 6:61-78 (1992)), CAVEAT (Bartlett et al. in "Molecular Recognition in Chemical and Biological Problems", special publication of *The Royal Chem. Soc.,* 78:182-196 (1989)) and MCSS (Miranker et al. *Proteins* 11:29-34 (1991)).

Further, examples of methods for the synthesis of molecular libraries can be found in the art, for example in: DeWitt et al. (1993) *Proc. Natl. Acad. Sci. U.S.A.* 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc Natl Acad Sci USA 89:1865-1869) or on phage (Scott and Smith (1990) Science 249:386-390); (Devlin (1990) Science 249:404-406); (Cwirla et al. (1990) Proc. Natl. Acad. Sci. 87:6378-6382); (Felici (1991) J. Mol. Biol. 222:301-310); (Ladner supra.).

The potential modulator effect of a compound can be further analyzed prior to its actual synthesis and testing by use of computer modeling techniques using the structural coordinates of the MCL-1 active site. If the computer modeling indicates an interaction, the molecule can then be synthesized using standard methods known to those skilled in the chemical arts, and then tested for its ability to modulate the activity of a MCL-1 or related polypeptide using the assays set forth herein.

A modulator or other binding compound of a MCL-1 or related polypeptide may be computationally evaluated and designed by means of a series of steps in which chemical entities or fragments are screened and selected for their ability to associate with the individual active site. As will be recognized by the skilled artisan, fragment-based drug design can be used to develop small molecules that mimic the MCL-1 specific binding elements of MCL-1-specific SAHBs, such as those agents described herein as selective for the MCL-1 BH3 domain.

In other embodiments of the method of the invention, potential modulator compounds can be examined for their ability to associate with a MCL-1 or related polypeptide's active site. This process can involve visual inspection of, for example, the active site on a computer screen based on the structural coordinates of the MCL-1 active site. Selected compounds or chemical moieties can then be positioned in a variety of orientations, or docked, within an individual region of the active site as defined herein. Docking can be accomplished using software such as Quanta and SYBYL, followed by energy minimization and molecular dynamics with standard molecular mechanics forcefields, such as CHARMM and AMBER.

In some embodiments, the invention involves the inputting of structural coordinates of MCL-1 or related polypeptides into an electronic storage medium to generate a three-dimensional computer model of the polypeptide. In one embodiment, the complete structural coordinates of a MCL-1 polypeptide are input. In an alternative embodiment, a fragment, or less than the complete structural coordinates, but including the active site are inputted. The structural coordinates may be known in the art or based on homology modeling. For example, known BCL-2 family structural coordinates include BAX (PDB ID No. 1f16), BAK (PDB ID No. 2ims), BCL-2 (PDB ID No. 1g5m), and BCL-XL (PDB ID No. 1lxl), and BIM BH3-BAX (PDB ID No. 2k7w), as well as MCL-1 structural coordinates described herein (e.g., MCL-1's BH3 domain (PDB#1pqk, SEQ ID NO: 1A), and others known in the art. Structural coordinates for many known BCL-2 family polypeptides can be obtained from the Protein Data Bank ("PDB") (Research Collaboratory for Structural Bioinformatics; http://www.rcsb.org).

The present invention further provides that the structural coordinates of the present invention may be used with standard homology modeling techniques in order to determine the unknown three-dimensional structure of a molecule or molecular complex. Homology modeling involves constructing a model of an unknown structure using structural coordinates of one or more related protein molecules, molecular complexes or parts thereof (i.e., active sites). Homology modeling may be conducted by fitting common or homologous portions of the protein whose three dimensional structure is to be solved to the three dimensional structure of homologous structural elements in the known molecule, specifically using the relevant (i.e., homologous) structural coordinates. Homology may be determined using amino acid sequence identity, homologous secondary structure elements, and/or homologous tertiary folds. Homology modeling can include rebuilding part or all of a three dimensional structure with replacement of amino acid residues (or other components) by those of the related structure to be solved.

Similar methods are known to those skilled in the art (Greer, 1985, Science 228, 1055; Bundell et al 1988, Eur. J. Biochem. 172, 513; Knighton et al., 1992, Science 258:130-135, http://biochem.vt.edu/courses/modeling/homology.htm). Computer programs that can be used in homology modeling include Quanta and the homology module in the Insight II modeling package (Accelrys, Inc., San Diego, Calif.) or MODELLER (Rockefeller University, www.iucr.ac:uk/sinris-top/logical/prg-modeller.html, Sali's Modeller also from Accelrys, Inc., San Diego, Calif.).

Once an interaction template is prepared compounds which bind the MCL-1 or related polypeptide's active site can be identified. Specialized computer programs that can also be used in the process of selecting compounds or chemical entities include:
1. SYBYL Available from Tripos Inc., 1699 South Hanley Rd., St. Louis, Mo., 63144, USA
2. UNITY Available from Tripos Inc., 1699 South Hanley Rd., St. Louis, Mo., 63144, USA
3. FlexX Available from Tripos Inc., 1699 South Hanley Rd., St. Louis, Mo., 63144, USA
4. GRID (Goodford, P. J., "A Computational Procedure for Determining Energetically Favorable Binding Sites on Biologically Important Macromolecules", J. Med. Chem., 28, pp. 849-857 (1985)). GRID is available from Oxford University, Oxford, UK.
5. MCSS (Miranker, A. and M. Karplus, "Functionality Maps of Binding Sites: A Multiple Copy Simultaneous Search Method." Proteins: Structure. Function and Genetics, 11, pp. 29-34 (1991)). MCSS is available from Molecular Simulations, Burlington, Mass.
6. AUTODOCK (Goodsell, D. S, and A. J. Olsen, "Automated Docking of Substrates to Proteins by Simulated Annealing", Proteins: Structure. Function, and Genetics, 8, pp. 195-202 (1990)). AUTODOCK is available from Scripps Research Institute, La Jolla, Calif.
7. DOCK (Kuntz, I. D. et al., "A Geometric Approach to Macromolecule-Ligand Interactions", J. Mol. Biol., 161, pp. 269-288 (1982)). DOCK is available from University of California, San Francisco, Calif.

Once suitable compounds or chemical moieties have been selected, they can be assembled into a single compound or inhibitor. Assembly may be proceed by visual inspection of the relationship of the compounds or moieties to each other on the three-dimensional image displayed on a computer screen in relation to the structure coordinates of the BAX/BIM-BH3 NMR binding studies. This could then be followed by manual model building using software such as Quanta or SYBYL.

Other useful programs to aid one of skill in the art in connecting the individual compounds or chemical entities include:
1. CAVEAT (Bartlett, P. A. et al, "CAVEAT: A Program to Facilitate the Structure-Derived Design of Biologically Active Molecules". In "Molecular Recognition in Chemical and Biological Problems", Special Pub., Royal Chem. Soc., 78, pp. 182-196 (1989)). CAVEAT is available from the University of California, Berkeley, Calif.
2. 3D Database systems such as MACCS-3D (MDL Information Systems, San Leandro, Calif.). This area is reviewed in Martin, Y. C., "3D Database Searching in Drug Design", J. Med. Chem., 35, pp. 2145-2154 (1992)).
3. HOOK (available from Molecular Simulations, Burlington, Mass.).

In other embodiments, BCL-2 family polypeptide modulators can be designed as a whole or "de novo" using either an empty active site or optionally including some portion(s) of a known modulator(s). Programs which can aid in these methods include:
1. LUDI (Bohm, H.-J., "The Computer Program LUDI: A New Method for the De Novo Design of Enzyme Inhibitors", J. Comp. Aid. Molec. Design, 6, pp. 61-78 (1992)). LUDI is available from Biosym Technologies, San Diego, Calif.
2. LEGEND (Nishibata, Y. and A. Itai, Tetrahedron, 47, p. 8985 (1991)). LEGEND is available from Molecular Simulations, Burlington, Mass.
3. LeapFrog (available from Tripos Associates, St. Louis, Mo.).

Other molecular modeling techniques may also be employed in accordance with this invention. See, e.g., Cohen, N. C. et al., "Molecular Modeling Software and Methods for Medicinal Chemistry", J. Med. Chem., 33, pp. 883-894 (1990). See also, Navia, M. A. and M. A. Murcko, "The Use of Structural Information in Drug Design", Current Opinions in Structural Biology, 2, pp. 202-210 (1992).

Once a compound has been designed or selected by the above methods, the efficiency with which that compound modulates a MCL-1 or related polypeptide can be tested and optimized by computational evaluation. An effective MCL-1 polypeptide modulator (or modulator of an MCL-1-related polypeptide) must preferably demonstrate a relatively small difference in energy between its bound and free states (i.e., a small deformation energy of binding).

A compound designed or selected as a modulator of MCL-1 or related polypeptide can be further computationally optimized so that in its bound state it would preferably lack repulsive electrostatic interaction with the target protein. Such non-complementary (e.g., electrostatic) interactions include repulsive charge-charge, dipole-dipole and charge-dipole interactions. Specifically, the sum of all electrostatic interactions between the modulator and the enzyme when the modulator is bound to MCL-1 or related polypeptide preferably make a neutral or favorable contribution to the enthalpy of binding.

Specific computer software is available in the art to evaluate compound deformation energy and electrostatic interaction. Examples of programs designed for such uses include: Gaussian 92, revision C, M. J. Frisch, Gaussian, Inc., Pittsburgh, Pa.; AMBER, version 4.0, P. A. Kollman, University of California at San Francisco; QUANTA/CHARMM, Molecular Simulations, Inc., Burlington, Mass.; and Insight II/Discover (Biosysm Technologies Inc., San Diego, Calif.). These programs may be implemented, for instance, using a Silicon Graphics workstation, IRIS 4D/35 or IBM RISC/6000 workstation model 550. Other hardware systems and software packages will be known to those skilled in the art.

Furthermore, fragment-based drug discovery can be used to identify compounds which interact with the active site of MCL-1 or related polypeptide. These methods are known and computational tools for their use are commercially available, for example "SAR by NMR" (Shukers, S. B., et al., Science, 1996, 274, 1531-1534), "Fragments of Active Structures" (www.stromix.com; Nienaber, V. L., et al., Nat. Biotechnol., 2000, 18, 1105-1108), and "Dynamic Combinatorial X-ray Crystallography" (e.g., permitting self-selection by the protein molecule of self-assembling fragments; Congreve, M. S., et al., Angew. Chem., Int. Ed., 2003, 42, 4479-4482). Bray et al. described one established fragment-based approach can be pursued (Bray, B. L. *Nature Reviews* Drug Discovery, 2003. 2(7): p. 587-593; MYUNG-CHOL KANG, B. B., et al., *Methods and compositions for peptide synthesis*, U.S.P.a.T. Office, Editor. Jan. 18, 2000 USA). In this strategy, the peptide is divided into 3 fragments, such that an N-terminal, central, and C-terminal portion are synthesized independently. These polypeptide fragments should be generated using solid phase Fmoc chemistry and ruthenium-catalyzed olefin metathesis on super-acid cleavable resins, which will yield fully protected peptides having an Fmoc at the N-terminus, and either a C-terminal amide (for the C-terminal fragment) or a free carboxylate (for the central and N-terminal fragments). These fully protected fragments are purified by reverse-phase high performance liquid chromatography, followed by sequential deprotection, coupling, and purification, to yield the full length, fully protected polypeptides. Global deprotection, followed by reverse-phase high performance liquid chromatography will yield the final products, which can be characterized using LC/MS mass spectrometry and amino acid analysis.

Once a MCL-1 polypeptide modulator (or modulator of MCL-1-related polypeptide) has been optimally selected or designed, as described herein, substitutions can then be made in some of its atoms or side groups in order to improve or modify its binding properties, again using the information provided by the interaction and specificity templates to identify regions amiable to modification. Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analyzed for efficiency of fit to MCL-1 or related polypeptides by the same computer methods described in detail, above.

In certain embodiments the modulators have a Kd for MCL-1 polypeptides (or, optionally, for MCL-1-related polypeptides) of less than 0.2 mM, less than 0.1 mM, less than 750 μM, less than 500 μM, less than 250 μM, less than 100 μM, less than 50 μM, less than 500 nM, less than 250 nM, less than 50 nM, less than 30 nm, less than 20 nM, less than 10 nM, less than 5 nM, less than 3 nM, less than 1 nM, or less than 0.5 nM.

Designed modulators can be further evaluated using in vitro or in vivo assays known in the art and described herein.
In Vitro Assays for Assessing MCL-1 Peptide Modulation and Compound Binding Determining the ability of a compound, found to bind the active site of a MCL-1 polypeptide based on computer modeling, library screening, and/or fragment-based drug discovery, can be evaluated further for MCL-1 polypeptide interaction by testing direct binding. Determining the ability of a test compound to bind to a MCL-1 polypeptide can be accomplished, for example, by coupling the MCL-1 polypeptide or compound with a radioisotope or enzymatic label such that binding of the MCL-1 polypeptide to the potential modulator can be determined by detecting the labeled MCL-1 polypeptide in a complex. For example, a compound can be labeled with $^{125}I$, $^{35}S$, $^{14}C$, or $^{3}H$, either directly or indirectly, and the radioisotope detected by direct counting of radioemission or by scintillation counting. Alternatively, the compound can be enzymatically labeled with, for example, horseradish peroxidase, alkaline phosphatase, or luciferase, and the enzymatic label detected by determination of conversion of an appropriate substrate to product. As a further example, the compound can be labelled with fluorescein and binding interactions between ligand and MCL-1 polypeptide quantitated using a fluorescence polarization assay. Binding can also be measured by HSQC NMR, as described herein.

In other embodiments, determining the ability of the modulator to bind to MCL-1 polypeptides can be determined by detecting induction of a downstream event (e.g., change in conformation, oligomerization state, or subcellular localization of the polypeptide, apoptosis, release of mitochondrial cytochrome c, etc.) or detecting another MCL-1-regulated cellular response.

In another embodiment, the assay is a cell-free assay in which a MCL-1 protein or biologically active portion thereof containing an active site is contacted with a test compound and the ability of the test compound to modulate the activity of the MCL-1 protein or biologically active portion thereof is determined Determining the ability of the test compound to modulate the activity of a MCL-1 protein can be accomplished, for example, by determining the ability of the MCL-1 protein to bind to another MCL-1 protein and/or another BCL-2 family target molecule in the presence of the test compound.

Determining the ability of the MCL-1 protein to bind to a target molecule can also be accomplished using a technology such as real-time Biomolecular Interaction Analysis (BIA). Sjolander, S, and Urbaniczky, C. (1991) Anal. Chem. 63:2338-2345 and Szabo et al. (1995) Curr. Opin. Struct. Biol. 5:699-705. As used herein, "BIA" is a technology for studying biospecific interactions in real time, without labeling any of the interactants (e.g., BLAcore). Changes in the optical phenomenon of surface plasmon resonance (SPR) can be used as an indication of real-time reactions between biological molecules.

In an alternative embodiment, determining the ability of the test compound to modulate the activity of a MCL-1 protein can be accomplished by determining the ability of the MCL-1 protein to modulate the activity of a downstream MCL-1 target molecule. For example, the activity of the effector molecule on an appropriate target can be determined, or the binding of the effector to an appropriate target can be determined as previously described.

In yet another embodiment, the cell-free assay involves contacting a MCL-1 or biologically active portion thereof containing the active site, with a known compound which binds the MCL-1 protein (e.g., BAX or BAK, e.g., a hydrocarbon-stapled BAX or BAK BH3 polypeptide) to form an assay, and determining the ability of the test compound to interact with the MCL-1 protein, wherein determining the ability of the test compound to interact with the MCL-1 protein comprises determining the ability of the test compound to preferentially bind to or modulate the activity of a MCL-1 protein and displace the known compound.

In more than one embodiment of the above assay methods of the present invention, it may be desirable to immobilize either the MCL-1 polypeptide or its target molecule to facilitate separation of complexed from uncomplexed forms of one or both of the proteins, as well as to accommodate automation of the assay. Binding of a test compound to a MCL-1 protein, or interaction of a MCL-1 protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/MCL-1 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or MCL-1 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of MCL-1 binding or activity determined using standard techniques.

Other techniques for immobilizing proteins on matrices can also be used in the assays of the invention. For example, either a MCL-1 protein or a MCL-1 target molecule can be immobilized utilizing conjugation of biotin and streptavidin. Biotinylated MCL-1 protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with MCL-1 protein or target molecules but which do not interfere with binding of the MCL-1 protein to its target molecule can be derivatized to the wells of the plate, and unbound target or MCL-1 protein trapped in the wells by antibody conjugation. Methods for detecting such complexes, in addition to those described above for the GST-immobilized complexes, include immunodetection of complexes using antibodies reactive with the MCL-1 protein or target molecule, as well as enzyme-linked assays which rely on detecting an enzymatic activity associated with the MCL-1 protein or target molecule.

The compounds that bind the active site of MCL-1 polypeptides may be demonstrated to inhibit tumor cell number in vitro or in vivo using a variety of assays known in the art, or described herein. Such assays can use cells of a cancer cell line or cells from a patient in the presence and absence of the compound of interest. Preferably the cell has a deregulated MCL-1 polypeptide pathway. The ability of a compound or a regimen of the invention to reduce the number of cancer cells or inhibit their proliferation can be assessed by methods known in the art and described herein.

The invention provides methods (also referred to herein as "screening assays") for identifying compounds which bind to an active site and modulate the activity of MCL-1 proteins.

The binding affinity of polypeptides described herein can be determined using, for example, a titration binding assay. A MCL-1 polypeptide or polypeptide comprising a BH domain (e.g., MCL-1, etc.) can be exposed to varying concentrations of a candidate compound (i.e., polypeptide, small molecule) (e.g., 1 nM, 10 nM, 100 nM, 1 uM, 10 uM, 100 uM, 1 mM, and 10 mM) in the presence of a substrate such as a fluorescently labeled BH3 containing polypeptide or a fragment thereof (e.g., MCL-1 etc.). The effect of each concentration of candidate compound is then analyzed to determine the effect of the candidate compound on MCL-1 polypeptide binding activity at varying concentrations, which can be used to calculate the Ki of the candidate compound. The candidate compound can modulate BCL-2 type activity in a competitive or non-competitive manner Direct binding assays can also be performed between MCL-1 proteins and fluorescently labeled candidate compounds to determine the Kd for the binding interaction. Cell permeability screening assays are also envisioned, in which fluorescently or otherwise labeled candidate compounds are applied to intact cells, which are then assayed for cellular fluorescence by microscopy or high-throughput cellular fluorescence detection.

A compound, pharmaceutical composition, or regimen of the invention is preferably tested in vitro, using assays that correlate with in vivo activity, and then in vivo for the desired therapeutic or prophylactic activity prior to use in humans. For example, assays which can be used to determine whether administration of a specific compound is effective include cell culture assays in which a patient tissue sample (e.g., cancer cell) is grown in culture and exposed to, or otherwise contacted with, a compound of the invention, and the effect of such compound upon the tissue sample is observed. The tissue sample can be obtained by biopsy or blood/bone marrow draw from the patient. This test allows the identification of the therapeutically most effective therapy (e.g., prophylactic or therapeutic agent) for each individual patient.

The assays described herein can be performed with individual candidate compounds or can be performed with a plurality of candidate compounds. Where the assays are performed with a plurality of candidate compounds, the assays can be performed using mixtures of candidate compounds or can be run in parallel reactions with each reaction having a single candidate compound. The test compounds or agents can be obtained using any of the numerous approaches in combinatorial library methods known in the art.

In a preferred embodiment, cell-based assay is performed on a compound which is known to bind an active site (e.g., identified via computer modeling, direct binding assay, NMR, or other method) of a MCL-1 polypeptide in order to determine whether the compound also modulates the activity of the MCL-1 polypeptide.

In one embodiment, an assay is a cell-based assay in which a cell that expresses a MCL-1 protein or biologically active portion thereof is contacted with a candidate compound, and the ability of the candidate compound to bind to an active site and modulate MCL-1 type activity is determined (e.g., in some instances increase in apoptosis and in other instances decrease apoptosis, via intrinsic or extrinsic cell death pathways). Determining the ability of the test compound to modulate BCL-2 type activity within cells can be accomplished by monitoring, for example, release of cytochrome c from the mitochondria or other relevant physiologic readout (e.g., annexin V staining, MTT assay, caspase activity assay, TUNEL assay, change in mitochondrial membrane potential).

In vitro anti-tumor activity of the compounds found to bind to the active site of a MCL-1 polypeptide can be assayed by measuring the ability of the compound to kill tumor cells. Examples of cell lines include: human lung (A549); resistant human lung with low topo II activity (A549-VP); murine melanoma (B16); human colon tumor (HCT116); human clone tumor with elevated p170 levels (HCTVM); human colon tumor with low topo II activity (HCTVP); P388 murine lymph leukemia cells; and human colon carcinoma cell line (Moser), and many others known in the art.

Tumor inhibition assays are described, for example, in Kelly, et al., U.S. Pat. No. 5,166,208, and in Pandley, et al., J. Antibiot. 3(11):1389-401 (1981). In one assay, the cells are allowed to grow for a 24 hour period under standard conditions. After the cells are allowed to attach to the plate for 24 hours (e.g., a 96-well flat bottom plate), the cells are incubated for 72 hours with serially diluted concentrations of the MCL-1 modulator compound. From these data, the concentration of the compound at which 50% of the cells are killed or growth inhibited (IC50) is determined.

Screening for MCL-1-Specific Small Molecules by Competitive Binding Assay

The specificity of MCL-1-specific SAHB/MCL-1 complexes can be taken advantage of for purpose of conducting a competitive fluorescence polarization binding assay screen to identify small molecule modulators of MCL-1. Such assays have the advantage of being a means by which to leverage the specificity of SAHB/MCL-1 complexes such as those described herein to identify targeted small molecule modulators of MCL-1 or MCL-1-related polypeptides.

For example, a high-throughput competitive fluorescence polarization binding assay can be employed to screen for small molecules that disrupt the interaction between FITC-MCL-1-specific SAHB and recombinant MCL-1. In such an assay, MCL-1 is expressed and purified by FPLC and delivered by automated liquid handler to 384 well plates containing small molecule libraries. After incubation at room temperature, FITC-ligand is added to each well by liquid handler and FP read at equilibrium (e.g. 30 min). Small molecule hits are re-examined in this assay using 4-place serial dilution of the compounds to confirm dose-responsive inhibition of FITC-MCL-1-specific SAHB binding (e.g. MCL-1 SEQ ID NO: 12, 17-60, NOXA SEQ ID NO: 63-68, BOK SEQ ID: 11). Small molecule hits are advanced to rigorous quantitation of binding activity and specificity. Serial dilutions of small molecules in triplicate are mixed with FITC-MCL-1-specific SAHB, followed by addition to 384-well plates containing recombinant MCL-1 diluted in binding buffer (e.g. 50 mM Tris pH 7.4, 100 nM NaCl). FP (mP units) is measured at equilibrium by microplate reader (e.g. Spectramax) and $K_i$ values calculated by nonlinear regression analysis of dose-response curves using Prism software (Graphpad). For specificity analysis, the identical experiment is performed except that serial dilutions of small molecule hits are mixed with a pan-anti-apoptotic binder (e.g. FITC-BIM SAHB, 25 nM), followed by addition to plates containing either recombinant MCL-1, BCL-2, BCL-$X_L$, BCL-w, BCL-B, or BFL1/A1 protein. MCL-1-specific small molecules can then be subjected to a battery of functional assays to assess their capacity to disrupt in vitro and in situ MCL-1/target protein interactions (e.g. MCL-1/BAK) and modulate MCL-1 functions in cells (e.g. sensitize or reactivate apoptosis in cancer cells by inhibiting MCL-1).

In Vivo Testing of Compounds

The compounds of the invention can also be demonstrated to inhibit tumor formation in vivo. The compounds, pharmaceutical compositions, and regimens of the invention can be tested in suitable animal model systems prior to use in humans. Such animal model systems include, but are not limited to, rats, mice, chicken, cows, monkeys, pigs, dogs, rabbits, primates, etc., including transgenic animals and other animal models of disease. Any animal system known in the art may be used. Several aspects of the procedure may vary; said aspects include, but are not limited to, the temporal regime of administering the therapeutic modalities (e.g., prophylactic and/or therapeutic agents), whether such therapeutic modalities are administered separately or as an admixture, and the frequency of administration of the therapeutic modalities.

In vivo anti-tumor activity of MCL-1 modulator compounds of the invention can be assayed by a reduction of tumor cells in mammals (e.g., mice) and a resulting increase in survival time compared to untreated tumor bearing animals. For example, CDF1 mice are injected interperitoneally with a suspension of P388 murine lymph leukemia cells, Ehrlich carcinoma cells, B16 melanoma cells, or Meth-A fibrosarcoma cells. Some of the injected mice are then treated interperitoneally with a MCL-1 modulator compound of the invention, and other mice are treated with saline. The in vivo activity of the compound is then determined in terms of the % T/C which is the ratio of the mean survival time of the treated group to the mean survival time of the saline treated group times 100. Yokoi, et al., U.S. Pat. No. 4,584,377; Kelly, et al., U.S. Pat. No. 5,155,208; Warnick-Pickle, et al., J. Antibiot. 34(11):1402-7 (1981); and Pandley et al., supra.

A vast number of animal models of hyperproliferative disorders, including tumorigenesis and metastatic spread, are known in the art and are disclosed herein (see Chapter 317, "Principals of Neoplasia," in Harrison's: Principals of Internal Medicine, 13th Edition, Isselbacher et al., eds., McGraw-Hill, New York, p. 1814, and Lovejoy et al., 1997, J. Pathol. 181:130-135). Hyperproliferative disorders include cellular proliferation or apoptotic blockage disorders such as cancer and autoimmune disease. Examples of BCL-2 related cancers include, but are not limited to, solid tumors, leukemias, and lymphomas. In one embodiment, the disorder is a chemoresistant cancer. In another embodiment, the chemoresistant cancer is resistant to ABT-737 (available from Abbott; Abbott Park, Ill.). Specific examples include for lung cancer, transplantation of tumor nodules into rats (Wang et al., 1997, Ann. Thorac. Surg. 64:216-219) or establishment of lung cancer metastases in SCID mice depleted of NK cells (Yono and Sone, 1997, Gan To Kagaku Ryoho 24:489-494); for colon cancer, colon cancer transplantation of human colon cancer cells into nude mice (Gutman and Fidler, 1995, World J. Surg. 19:226-234), the cotton top tamarin model of human ulcerative colitis (Warren, 1996, Aliment. Pharmacol. Ther. Supp 12:45-47) and mouse models with mutations of the adenomatous polyposis tumor suppressor (Polakis, 1997, Biochim. Biophys. Acta 1332:F127-F147); for breast cancer, kansgenic models of breast cancer (Dankort and Muller, 1996, Cancer Treat. Res. 83:71-88; Amundadittir et al., 1996, Breast Cancer Res. Treat. 39:119-135) and chemical induction of tumors in rats (Russo and Russo, 5 1996, Breast Cancer Res. Treat. 39:7-20); for prostate cancer, chemically-induced and transgenic rodent models, and human xenograft models (Royal et al., 1996, Semin. Oncol. 23:35-40), for genitourinary cancers, induced bladder neoplasm in rats and mice (Oyasu, 1995, Food Chem. Toxicol 33:747-755) and xenografts of human transitional cell carcinomas into nude rats (Jarrett et al., 1995, J. Endourol. 9:1-7); and for hematopoietic cancers, transplanted allogeneic marrow in animals (Appelbaum, 1997, Leukemia 11 (Suppl. 4):S15-S17). Further, general animal models applicable to many types of cancer have been described, including, but not restricted to, the p53-deficient mouse model (Donehower, 1996, Semin. Cancer Biol. 7:269-278), the Min mouse (Shoemaker et al., 1997, Biochem. Biophys. Acta, 1332:F25-F48), and immune responses to tumors in rat 15 (Frey, 1997, Methods, 12:173-188).

For example, a compound of the invention can be administered to a test animal, in one embodiment a test animal predisposed to develop a type of tumor, and the test animal subsequently examined for a decreased incidence of tumor formation in comparison with an animal not administered the compound. Alternatively, a compound can be administered to test animals having tumors (e.g., animals in which tumors have been induced by introduction of malignant, neoplastic, or transformed cells, or by administration of a carcinogen) and subsequently examining the tumors in the test animals for tumor regression in comparison to animals not administered the compound. A compound of the invention is considered effective in treating a hyperpoliferative disorder when administration of a therapeutically effective amount increases time to tumor progression or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Similarly, a compound of the invention is considered effective in treating a hyperpoliferative disorder when administration of a therapeutically effective amount decreases the rate of tumor growth, decreases tumor mass, decreases the number of metastases by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Such results can be determined by one having ordinary skill in the relevant art, e.g., oncologist.

In Vitro and In Vivo Stability of Stapled Peptides

Structurally constrained peptides have demonstrated marked thermal stability and proteolytic stability in vitro as compared to native peptides For example, stapled peptides 22 to 36 amino acids in length were subjected to thermal unfolding, circular dichroism studies across a 1-91° C. temperature range. It was observed that select single and double stapling of the peptides conferred α-helical stabilization that was remarkably heat-resistant, sustaining an up to 2.3-fold enhancement in α-helicity even at 91° C. as compared to the native peptide.

Further, a major limitation of peptides as therapeutics is their susceptibility to rapid proteolytic degradation. Biologically active peptides that are lengthy, unfolded, and replete with protease sites are particularly vulnerable. One of the potential benefits of a covalent crosslinking strategy to enforce peptide α-helicity is shielding of the vulnerable amide bonds from proteolysis. Because proteases require that peptides adopt an extended conformation to hydrolyze amide bonds, the structural constraint afforded by the hydrocarbon staple can render crosslinked peptides protease-resistant. To determine if hydrocarbon stapling, and especially double stapling, could protect the 36 to 37 amino acid peptides, the native peptides and stapled peptides were subject to direct protease exposure in vitro. To especially challenge the stapled peptides, a protease that could cleave the peptide at multiple sites was selected.

In the presence of the protease, the native peptides exhibited rapid degradation, with half-lives of 12 and 14 minutes. In comparison, singly stapled peptides displayed longer half-lives that ranged from 21 to 200 minutes. The majority of doubly stapled compounds markedly surpassed their singly stapled counterparts, with select doubly stapled peptides achieving half-lives of up to 1275 minutes. In most cases, double stapling had a stronger influence on proteolytic stability than overall peptide α-helicity, as select doubly stapled peptides had lower α-helicity than select singly stapled peptides, but still exhibited superior protease resistance. Almost all stapled peptides had the identical number of protease cleavage sites as the corresponding unmodified peptides, emphasizing that the observed protease resistance derived from peptide stapling itself, rather than elimination of cleavage sites.

Non-modified peptides typically have limited oral bioavailability in part due to rapid acid hydrolysis in the proximal digestive tract. The compelling protease resistance of stapled peptides at neutral pH prompted the exploration of their stability under acidic conditions. In each case, acidification of the peptide solutions significantly enhanced their α-helical content as measured by CD. Upon exposure to pepsin, the native peptides exhibited rapid degradation, with half-lives of 4 and 11 minutes, respectively. Select doubly stapled peptides displayed half-lives ranging from approximately 80-800-fold greater than the unmodified peptides, and consistently surpassed their singly stapled counterparts. Remarkably, select doubly-stapled peptides remained 80% intact after exposure to pepsin at pH 2 for more than 12 hours. As observed for protease resistance at neutral pH, double stapling itself, rather than overall peptide α-helicity or number of cleavage sites, correlated with the superior resistance to pepsin hydrolysis. These studies highlighted the capacity of stapled peptides with unprecedented resistance to proteolytic hydrolysis at both neutral and acidic pH.

A stapled peptide was further analyzed for stability and bioavailabilty in vivo as compared to native peptide. Male C57/BL6 mice were administered intravenously or by oral gavage 10 mg/kg of either a doubly stapled peptide or the corresponding unmodified peptide. Blood samples withdrawn at 30 minutes by retro-orbital bleed were subjected to quantitation using LC/MS-based blood tests. The level of stapled peptide measured in the blood was more than 6-fold greater than the measured level of the corresponding unmodified peptide. Noncompartmental pharmacologic analysis based on serial blood draws, revealed a 10-fold enhancement in area under the curve of the stapled peptide as compared to the native peptide. Strikingly, 30 minutes after oral administration, intact stapled peptide was detected in the blood at measurable and dose-responsive levels, whereas the unmodified peptide was undetectable. Both AUC and clearance were improved by about 10-fold.

These data emphasize that hydrocarbon stapling confers unique pharmacologic properties to stapled peptide sequences, enhancing their in vivo stability and even conferring measurable oral bioavailability. This experiment further demonstrated that an equivalent oral dose of stapled peptides could produce serum levels comparable that resulting from intravenous dosing of the unmodified peptide, suggesting that a therapeutically effective dose of a stapled peptide could be administered orally.

In Vivo Testing of MCL-1-Targeting SAHB Compounds

MCL-1 modulators are optionally evaluated in cellular systems such as those described in Example 5 below, for purpose of assaying impact of such modulators upon apoptosis induction, autophagy induction, cell cycle arrest, inhibiting inflammatory responses, neutralizing survival mechanisms of relevant pathogens, e.g. tuberculosis, etc. Compounds can be tested in animal models of relevant diseases (e.g., cancer xenografts, inflammatory models, infectious disease models), with such animal models described in greater detail below.

Implications of MCL-1 binding and the SAHB-mediated dissociation from native complexes can lead to gain of function—e.g., redirect MCL-1 to binding a distinct target (known or unknown). MCL-1 targeting SAHBs can be used in this context to identify novel targets and functions of MCL-1 (e.g. autophagy regulation, cell-cycle regulation, RNA splicing). For example, the following experimental approaches can be used:

Isolation of SAHB-Bound Proteins and Protein Complexes

Cells are treated with FITC- or biotin-conjugated MCL-1-selective SAHBs (5-20 µM) in serum free medium followed by serum replacement at 2-4 hours, and after incubation at various time points (e.g. 4, 8, 24 hours), cells are harvested and extracted with lysis buffer. SAHB-bound proteins/protein complexes are isolated by anti-FITC pull down, performed as described (Walensky et al. Mol Cell, 2006; Pitter et al, Methods in Enzymology, 2008) or by streptavidin agarose capture (see Example 5). The lysates are evaluated by SDS/PAGE, Silver Stain Plus (Biorad) and tandem mass spectrometry. Bands that appear in SAHB-exposed lysates, but not those treated with vehicle or SAHB point mutant, are excised with a razor and minced. The minced bands are washed once with water and twice with 25 mM ammonium bicarbonate for 10 minutes at room temperature. The bands are incubated with 1% hydroxide in 25 mM ammonium bicarbonate for 5 minutes to remove the silver stain. Once the gel slices are clear, the gel is washed in water, 1% formic acid, 50:50 water:acetonitrile with 1% formic acid, followed by acetonitrile for 5 minutes each. The gel slice is then subjected to proteolytic digestion, extraction, and tandem mass spectrometry (MSMS). Mascot Search engine software is used to match the identified fragments with known protein sequences.

Because some protein interactors are fleeting or may not survive the cellular lysis conditions, our alternative covalent crosslinking approach can be deployed to identify MCL-1-selective SAHB-bound proteins and protein complexes (reference Danial patent and Walensky BAX patent). A photoactivatable crosslinking moiety (e.g. BPA) is installed in the MCL-1 targeting SAHB sequence (e.g. SEQ ID NO: 34, 71, 72) and after cellular treatment or direct exposure to cellular lysates, UV irradiation induces covalent intercalation of SAHB into its bound target protein(s). SAHB-target retrieval is achieved using anti-FITC or streptavidin-biotin-based capture as described above.

Immunoprecipitation of MCL-1 to Identify SAHB-Induced Changes of MCL-1 Binding Interactions To evaluate the impact of targeting MCL-1 protein interactions by MCL-1-selective SAHBs (or identified small molecules, see above), MCL-1 over-expressing cancer cells ($10 \times 10^6$) are incubated with the MCL-1 targeting SAHB, vehicle, or mutant SAHB in serum-free media at 37° C. for 4 hours, followed by serum replacement for 6 hours. After cellular lysis (e.g. 50 mM Tris (pH 7.4), 150 mM NaCl, 1 mM EDTA, 1% CHAPS and complete protease inhibitor pellet), cellular debris is pelleted at 14,000 g for 10 minutes at 4° C. The supernatant is incubated with pre-equilibrated protein A/G sepharose beads. The pre-cleared supernatant is then treated with anti-MCL-1 antibody for 1.5 hours at 4° C. with rotation, followed by exposure to the protein A/G sepharose beads for 1 hour. The beads are pelleted and washed with lysis buffer for 10 minutes at 4° C. The washed beads are pelleted, heated to 90° C. for 10 minutes in SDS loading buffer, and analyzed by SDS/PAGE. To search for novel interactors (comparing electrophoresed proteins from untreated and SAHB-treated immunoprecipitates), the immunoprecipitates are evaluated by Silver Stain Plus (Biorad), and bands that appear or disappear in the SAHB-exposed immunoprecipitates, but not in those treated with vehicle or SAHB point mutant, are excised and then analyzed by tandem mass spectroscopy and MASCOT fragment identification software.

The following is an example of an in vivo efficacy testing methodology (cancer treatment model). Lead MCL-1-targeting SAHBs undergo pharmacokinetic (PK) analysis in mice. LC/MS-based analytical assays are developed in order to detect and quantitate compound levels in plasma. For PK analysis, SAHBs (e.g. 10, 50, 100 mg/kg) are injected by tail vein or intraperitoneally into male C57/BL6 mice. Blood samples are withdrawn by retro-orbital bleed at various time points and plasma isolated for compound quantitation, followed by calculation of plasma half-life, peak plasma levels, total plasma clearance, and apparent volume of distribution. Molecules that display a robust PK profile are advanced to in vivo efficacy studies.

Compound-sensitive hematologic cancer cell lines are retrovirally transduced to achieve stable luciferase expression (pMMP-LucNeo) and transplanted into SCID beige mice as previously described (Armstrong et al., 2003; Walensky et al., 2004). Initial xenograft studies examine 5 mouse cohorts (n=10), treated with either vehicle alone, low or high dose SAHB, or low/high dose SAHB in combination with a pro-apoptotic stimulus (e.g. subtherapeutic dosing of NOXA SAHB, doxorubicin, etoposide, dexamethasone). For example, starting on experimental day 1, mice receive a once daily tail injection of SAHB (e.g. 10 or 50 mg/kg, with or without co-treatment). For alternate day in vivo tumor imaging, mice are anesthetized with inhaled isoflurane and treated concomitantly with intraperitoneal injection of D-luciferin. Photonic emission is imaged (2 min exposure) using the Xenogen In Vivo Imaging System and total body bioluminescence quantified by the integration of photonic flux (photons/sec) using Xenogen's Living Image Software. The survival distributions of experimental mice are determined using the Kaplan-Meier method and compared using the log-rank test. The Fisher's exact test is used to compare the proportion of mice who fail treatment, where treatment failure is defined as progression or death, and success as stable disease or regression. If a treatment response is observed with a particular MCL-1 targeting SAHB, two additional cohorts, treated with either vehicle or the effective combination of SAHB and apoptotic co-stimulus, are used for pharmacodynamic studies in which pro-apoptotic activity is evaluated in tissues by TUNEL and activated caspase-3 immunohistochemical staining (Danial et al., 2008).

Further, any assays known to those skilled in the art can be used to evaluate the prophylactic and/or therapeutic utility of a compound or pharmaceutical composition disclosed herein for disorder associated with excessive cellular proliferation or cellular death or one or more symptoms thereof.

Methods of Treatment

Agents of the present invention are useful for treating cells in which the cell death signal is down regulated and the affected cell has an inappropriately diminished propensity for cell death, which is referred to herein as being in a "decreased apoptotic state." The invention further provides methods for the administration to a subject of a therapeutically effective amount of an agent to treat an apoptosis-associated disease in which it is desirable to induce apoptosis in certain types of cells, such as virus-infected or autoantibody-expressing cells. Typically, the agent is substantially purified prior to administration. The subject can be an animal, including but not limited to, cows, pigs, horses, chickens, cats, dogs, and the like, and is typically a mammal, and in a particular embodiment human. In another specific embodiment, a non-human mammal is the subject.

The present invention provides for both prophylactic and therapeutic methods of treating a subject at risk of (or susceptible to) a disorder or having a disorder associated with aberrant (e.g., insufficient or excessive) BCL-2 family member expression or activity (e.g., extrinsic or intrinsic apoptotic pathway abnormalities). As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes, antisense oligonucleotides, other nucleic acid compositions, and combinations thereof.

BCL-2 type disorders can be caused, at least in part, by an abnormal level of one or more BCL-2 family members (e.g., over or under expression of MCL-1), or by the presence of one or more BCL-2 family members exhibiting abnormal activity. As such, the invention is directed to the reduction in the level and/or activity of the MCL-1 or MCL-1-related polypeptide or the enhancement of the level and/or activity of the MCL-1 or MCL-1-related polypeptide, which would bring about the amelioration of disorder symptoms. For example, a tumor maintained by excessive levels of an anti-apoptotic protein such as MCL-1, can be treated with a MCL-1 inhibiting compound in order to surmount or circumvent apoptotic blockade and induce apoptosis.

The compounds of the invention can be used to treat and prevent cancers and neoplastic conditions. As used herein, the terms "cancer", "hyperproliferative" and "neoplastic" refer to cells having the capacity for autonomous growth and defective cell death, i.e., an abnormal state or condition characterized by rapidly proliferating cell growth and/or apoptotic blockade. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

Examples of cellular proliferative and/or differentiative disorders include cancer, e.g., carcinoma, sarcoma, or metastatic disorders. The compounds can act as novel therapeutic agents for controlling breast cancer, ovarian cancer, colon cancer, lung cancer, metastasis of such cancers and the like. A metastatic tumor can arise from a multitude of primary tumor types, including but not limited to those of breast, lung, liver, colon and ovarian origin.

Examples of cancers or neoplastic conditions include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

Some examples of immunologic disorders that can be treated with the compounds described herein include but are not limited to organ transplant rejection, arthritis, lupus, IBD, crone's disease, asthma, multiple sclerosis, diabetes etc.

Some examples of neurologic disorders that can be treated with the polypeptides described herein include but are not limited to Alzheimer's Disease, Down's Syndrome, Dutch Type Hereditary Cerebral Hemorrhage Amyloidosis, Reactive Amyloidosis, Familial Amyloid Nephropathy with Urticaria and Deafness, Muckle-Wells Syndrome, Idiopathic Myeloma; Macroglobulinemia-Associated Myeloma, Familial Amyloid Polyneuropathy, Familial Amyloid Cardiomyopathy, Isolated Cardiac Amyloid, Systemic Senile Amyloidosis, Adult Onset Diabetes, Insulinoma, Isolated Atrial Amyloid, Medullary Carcinoma of the Thyroid, Familial Amyloidosis, Hereditary Cerebral Hemorrhage With Amyloidosis, Familial Amyloidotic Polyneuropathy, Scrapie, Creutzfeldt-Jacob Disease, Gerstmann Straussler-Scheinker Syndrome, Bovine Spongiform Encephalitis, a Prion-mediated disease, and Huntington's Disease.

Some examples of endocrinologic disorders that can be treated with the polypeptides described herein include but are not limited to diabetes, hypthyroidism, hyopituitarism, hypoparathyroidism, hypogonadism, etc.

Examples of cardiovascular disorders (e.g., inflammatory disorders) that can be treated or prevented with the compounds and methods of the invention include, but are not limited to, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stent, synthetic or natural excision grafts, indwelling catheter, valve or other implantable devices. Preferred cardiovascular disorders include atherosclerosis, myocardial infarction, aneurism, and stroke.

Depending upon the specific nature of cancer cell apoptotic blockade/survival mechanisms, it may be beneficial to deploy an MCL-1 specific targeting agent (e.g., if the cell is exquisitely dependent on MCL-1, i.e. oncogene addiction) to lower the threshold for apoptosis induction and thereby decreasing the needed dosing levels of toxic chemotherapy, i.e., as described herein, MCL-1 inhibitors can be sensitizing agents for other anti-cancer agents (chemotherapy) and modalities (radiation), i.e. targeted therapy lowers treatment toxicity. In other contexts, the cells that are targeted for treatment may have multiple anti-apoptotic proteins overexpressed (i.e. relapsed and refractory cancer), so that in addition to MCL-1 targeting, the SAHB compound (or compound designed/identified to mimic such SAHB compound) deployed can be selected for its broad anti-apoptotic inhibiting activity that targets MCL-1 in addition to other anti-apoptotics.

Administration of Modulators

In one embodiment, the compounds of the invention are administered as monotherapy for the prevention, treatment, and/or management of cancer.

One aspect of the invention relates to a method of preventing, treating, and/or managing cancer in a patient (e.g., a human patient), the method comprising administering to the patient a prophylactically effective regimen or a therapeutically effective regimen, the regimen comprising administering to the patient a compound of the invention or a composition of the invention, wherein the patient has been diagnosed with cancer. The amount of a compound of the invention used in the prophylactic and/or therapeutic regimens which will be effective in the prevention, treatment, and/or management of cancer can be based on the currently prescribed dosage of the compound as well as assessed by methods disclosed herein.

In one embodiment of this aspect, the patient has received or is receiving another therapy. In another embodiment of this aspect, the patient has not previously received a therapy for the prevention, treatment, and/or management of the cancer.

The medical practitioner can diagnose the patient using any of the conventional cancer screening methods including, but not limited to physical examination (e.g., prostate examination, breast examination, lymph nodes examination, abdominal examination, skin surveillance), visual methods (e.g., colonoscopy, bronchoscopy, endoscopy), PAP smear analyses (cervical cancer), stool guaiac analyses, blood tests (e.g., complete blood count (CBC) test), blood chemistries including liver function tests, prostate specific antigen (PSA) test, carcinoembryonic antigen (CEA) test, cancer antigen (CA)-125 test, alpha-fetoprotein (AFP)), karyotyping analyses, bone marrow analyses (e.g., in cases of hematological malignancies), histology, cytology, a sputum analysis and imaging methods (e.g., computed tomography (CT), magnetic resonance imaging (MRI), ultrasound, X-ray imaging, mammograph imaging, bone scans).

Another aspect of the invention relates to a method of preventing, treating, and/or managing a solid tumor in a patient (e.g., a human patient), the method comprising administering to a patient in need thereof a prophylactically effective regimen or a therapeutically effective regimen, the regimen comprising administering to the patient a compound or composition of the invention wherein the patient has been diagnosed with a solid tumor, and wherein the patient has undergone a primary therapy to reduce the bulk of the tumor.

Another aspect of the invention relates to a method of preventing, treating, and/or managing cancer, the method comprising administering to a patient in need thereof a prophylactically effective regimen or a therapeutically effective regimen, the regimen comprising administering to the patient a compound of the invention (as described above), or a pharmaceutically acceptable salt thereof wherein the patient received another therapy. In some embodiments, the prior therapy is, for example, chemotherapy, radioimmunotherapy, toxin therapy, prodrug-activating enzyme therapy, antibody therapy, surgical therapy, immunotherapy, radiation therapy, targeted therapy or any combination thereof.

In some embodiments, the prior therapy has failed in the patient. In some embodiments, the therapeutically effective regimen comprising administration of a compound of the invention is administered to the patient immediately after patient has undergone the prior therapy. For instance, in certain embodiments, the outcome of the prior therapy may be unknown before the patient is administered a compound of the invention.

Another aspect of the invention relates to a method of preventing, treating, and/or managing cancer in a patient (e.g., a human patient), the method comprising administering to a patient in need thereof a prophylactically effective regimen or a therapeutically effective regimen, the regimen comprising administering to the patient a compound or composition of the invention, wherein the compound or composition of the invention is administered at a dose that is lower than the human equivalent dosage (HED) of the no observed adverse effect level (NOAEL) over a period of three months, four months, six months, nine months, 1 year, 2 years, 3 years, 4 years or more. The NOAEL, as determined in animal studies, is useful in determining the maximum recommended starting dose for human clinical trials. For instance, the NOAELs can be extrapolated to determine human equivalent dosages. Typically, such extrapolations between species are conducted based on the doses that are normalized to body surface area (i.e., mg/m$^2$). In specific embodiments, the NOAELs are determined in mice, hamsters, rats, ferrets, guinea pigs, rabbits, dogs, primates, primates (monkeys, marmosets, squirrel monkeys, baboons), micropigs or minipigs. For a discussion on the use of NOAELs and their extrapolation to determine human equivalent doses, see *Guidance for Industry Estimating the Maximum Safe Starting Dose in Initial Clinical Trials*

*for Therapeutics in Adult Healthy Volunteers*, U.S. Department of Health and Human Services Food and Drug Administration Center for Drug Evaluation and Research (CDER), Pharmacology and Toxicology, July 2005.

In certain embodiments, the regimens comprise administering a prophylactically effective regimen and/or a therapeutically effective regimen, wherein the regimen results in a reduction in the cancer cell population in the patient. In one embodiment, the patient undergoing the regimen is monitored to determine whether the regimen has resulted in a reduction in the cancer cell population in the patient.

Typically, the monitoring of the cancer cell population is conducted by detecting the number or amount of cancer cells in a specimen extracted from the patient. Methods of detecting the number or amount of cancer cells in a specimen are known in the art. This monitoring step is typically performed at least 1, 2, 4, 6, 8, 10, 12, 14, 15, 16, 18, 20, or 30 days after the patient begins receiving the regimen.

In some embodiments, the specimen may be a blood specimen, wherein the number or amount of cancer cells per unit of volume (e.g., 1 mL) or other measured unit (e.g., per unit field in the case of a histological analysis) is quantitated. The cancer cell population, in certain embodiments, can be determined as a percentage of the total blood cells.

In other embodiments, the specimen extracted from the patient is a tissue specimen (e.g., a biopsy extracted from suspected cancerous tissue), where the number or amount of cancer cells can be measured, for example, on the basis of the number or amount of cancer cells per unit weight of the tissue.

The number or amount of cancer cells in the extracted specimen can be compared with the numbers or amounts of cancer cells measured in reference samples to assess the efficacy of the regimen and amelioration of the cancer under therapy. In one embodiment, the reference sample is a specimen extracted from the patient undergoing therapy, wherein the specimen from the patient is extracted at an earlier time point (e.g., prior to receiving the regimen, as a baseline reference sample, or at an earlier time point while receiving the therapy). In another embodiment, the reference sample is extracted from a healthy, noncancer-afflicted patient.

In other embodiments the cancer cell population in the extracted specimen can be compared with a predetermined reference range. In a specific embodiment, the predetermined reference range is based on the number or amount of cancer cells obtained from a population(s) of patients suffering from the same type of cancer as the patient undergoing the therapy.

If the reduction in the cancer cell population is judged too small upon comparing the number, amount, or percentage of cancer cells in the specimen extracted from the patients undergoing therapy with the reference specimen, then the medical practitioner has a number of options to adjust the therapeutic regimen. For instance, the medical practitioner can then either increase the dosage of the compound or composition of the invention administered, the frequency of the administration, the duration of administration, or any combination thereof. In a specific embodiment, after the determination is made, a second effective amount of a compound or composition of the invention can be administered to the patient.

In other embodiments, the regimens comprise administering a compound or composition of the invention, wherein the regimen results in a reduction in the number, amount, or percentage of cancer cells and a reduction in the number, amount, or percentage of cancer cells in the patient.

The amount of a compound of the invention used in the prophylactic and/or therapeutic regimens which will be effective in the prevention, treatment, and/or management of cancer can be based on the currently prescribed dosage of the compound as well as assessed by methods disclosed herein and known in the art. The frequency and dosage will vary also according to factors specific for each patient depending on the specific compounds administered, the severity of the cancerous condition, the route of administration, as well as age, body, weight, response, and the past medical history of the patient. For example, the dosage of a compound of the invention which will be effective in the treatment, prevention, and/or management of cancer can be determined by administering the compound to an animal model such as, e.g., the animal models disclosed herein or known to those skilled in the art. In addition, in vitro assays may optionally be employed to help identify optimal dosage ranges.

In some embodiments, the prophylactic and/or therapeutic regimens comprise titrating the dosages administered to the patient so as to achieve a specified measure of therapeutic efficacy. Such measures include a reduction in the cancer cell population in the patient.

In certain embodiments, the dosage of the compound of the invention in the prophylactic and/or therapeutic regimen is adjusted so as to achieve a reduction in the number or amount of cancer cells found in a test specimen extracted from a patient after undergoing the prophylactic and/or therapeutic regimen, as compared with a reference sample. Here, the reference sample is a specimen extracted from the patient undergoing therapy, wherein the specimen is extracted from the patient at an earlier time point. In one embodiment, the reference sample is a specimen extracted from the same patient, prior to receiving the prophylactic and/or therapeutic regimen. In specific embodiments, the number or amount of cancer cells in the test specimen is at least 2%, 5%, 10%, 15%, 20%, 30%, 40%, 50%, 60%, 70%, 80%, 90%, 95% or 99% lower than in the reference sample.

In some embodiments, the dosage of the compound of the invention in the prophylactic and/or therapeutic regimen is adjusted so as to achieve a number or amount of cancer cells that falls within a predetermined reference range. In these embodiments, the number or amount of cancer cells in a test specimen is compared with a predetermined reference range.

In other embodiments, the dosage of the compound of the invention in prophylactic and/or therapeutic regimen is adjusted so as to achieve a reduction in the number or amount of cancer cells found in a test specimen extracted from a patient after undergoing the prophylactic and/or therapeutic regimen, as compared with a reference sample, wherein the reference sample is a specimen is extracted from a healthy, noncancer-afflicted patient. In specific embodiments, the number or amount of cancer cells in the test specimen is at least within 60%, 50%, 40%, 30%, 20%, 15%, 10%, 5%, or 2% of the number or amount of cancer cells in the reference sample.

In treating certain human patients having solid tumors, extracting multiple tissue specimens from a suspected tumor site may prove impracticable. In these embodiments, the dosage of the compounds of the invention in the prophylactic and/or therapeutic regimen for a human patient is extrapolated from doses in animal models that are effective to reduce the cancer population in those animal models. In the animal models, the prophylactic and/or therapeutic regimens are adjusted so as to achieve a reduction in the number or amount of cancer cells found in a test specimen extracted from an animal after undergoing the prophylactic and/or therapeutic regimen, as compared with a reference sample. The reference sample can be a specimen extracted from the same animal, prior to receiving the prophylactic and/or therapeutic regimen. In specific embodiments, the number or amount of cancer cells in the test specimen is at least 2%, 5%, 10%, 15%, 20%, 30%, 40%, 50% or 60% lower than in the reference sample. The doses effective in reducing the number or amount of cancer cells in the animals can be normalized to body surface area (e.g., mg/m$^2$) to provide an equivalent human dose.

The prophylactic and/or therapeutic regimens disclosed herein comprise administration of compounds of the invention or pharmaceutical compositions thereof to the patient in a single dose or in multiple doses (e.g., 1, 2, 3, 4, 5, 6, 7, 8, 10, 15, 20, or more doses).

In one embodiment, the prophylactic and/or therapeutic regimens comprise administration of the compounds of the invention or pharmaceutical compositions thereof in multiple doses. When administered in multiple doses, the compounds or pharmaceutical compositions are administered with a frequency and in an amount sufficient to prevent, treat, and/or manage the condition. In one embodiment, the frequency of administration ranges from once a day up to about once every eight weeks. In another embodiment, the frequency of administration ranges from about once a week up to about once every six weeks. In another embodiment, the frequency of administration ranges from about once every three weeks up to about once every four weeks.

Generally, the dosage of a compound of the invention administered to a subject to prevent, treat, and/or manage cancer is in the range of 0.01 to 500 mg/kg, and more typically, in the range of 0.1 mg/kg to 100 mg/kg, of the subject's body weight. In one embodiment, the dosage administered to a subject is in the range of 0.1 mg/kg to 50 mg/kg, or 1 mg/kg to 50 mg/kg, of the subject's body weight, more preferably in the range of 0.1 mg/kg to 25 mg/kg, or 1 mg/kg to 25 mg/kg, of the patient's body weight.

In a specific embodiment, the dosage of a compound of the invention administered to a subject to prevent, treat, and/or manage cancer in a patient is 500 mg/kg or less, preferably 250 mg/kg or less, 100 mg/kg or less, 95 mg/kg or less, 90 mg/kg or less, 85 mg/kg or less, 80 mg/kg or less, 75 mg/kg or less, 70 mg/kg or less, 65 mg/kg or less, 60 mg/kg or less, 55 mg/kg or less, 50 mg/kg or less, 45 mg/kg or less, 40 mg/kg or less, 35 mg/kg or less, 30 mg/kg or less, 25 mg/kg or less, 20 mg/kg or less, 15 mg/kg or less, 10 mg/kg or less, 5 mg/kg or less, 2.5 mg/kg or less, 2 mg/kg or less, 1.5 mg/kg or less, or 1 mg/kg or less of a patient's body weight.

In another specific embodiment, the dosage of a compound of the invention administered to a subject to prevent, treat, and/or manage cancer in a patient is a unit dose of 0.1 to 50 mg, 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

In a specific embodiment, the dosage of a compound of the invention administered to a subject to prevent, treat, and/or manage cancer in a patient is in the range of 0.01 to 10 g/m$^2$, and more typically, in the range of 0.1 g/m$^2$ to 7.5 g/m$^2$, of the subject's body weight. In one embodiment, the dosage administered to a subject is in the range of 0.5 g/m$^2$ to 5 g/m$^2$, or 1 g/m$^2$ to 5 g/m$^2$ of the subject's body's surface area.

In other embodiments, the prophylactic and/or therapeutic regimen comprises administering to a patient one or more doses of an effective amount of a compound of the invention, wherein the dose of an effective amount achieves a plasma level of at least 0.1 µg/mL, at least 0.5 µg/mL, at least 1 µg/mL, at least 2 µg/mL, at least 5 µg/mL, at least 6 µg/mL, at least 10 µg/mL, at least 15 µg/mL, at least 20 µg/mL, at least 25 µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL of the compound of the invention.

In other embodiments, the prophylactic and/or therapeutic regimen comprises administering to a patient a plurality of doses of an effective amount of a compound of the invention, wherein the plurality of doses maintains a plasma level of at least 0.1 µg/mL, at least 0.5 µg/mL, at least 1 µg/mL, at least 2 µg/mL, at least 5 µg/mL, at least 6 µg/mL, at least 10 µg/mL, at least 15 µg/mL, at least 20 µg/mL, at least 25 µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL of the compound of the invention for at least 1 day, 1 month, 2 months, 3 months, 4 months, 5 months, 6 months, 7 months, 8 months, 9 months, 10 months, 11 months, 12 months, 15 months, 18 months, 24 months or 36 months.

In some embodiments, the prophylactic and/or therapeutic regimen comprises administration of a compound of the invention in combination with one or more additional anticancer therapeutics. Preferably, the dosages of the one or more additional anticancer therapeutics used in the combination therapy is lower than those which have been or are currently being used to prevent, treat, and/or manage cancer. The recommended dosages of the one or more additional anticancer therapeutics currently used for the prevention, treatment, and/or management of cancer can be obtained from any reference in the art including, but not limited to, Hardman et al., eds., *Goodman & Gilman's The Pharmacological Basis Of Basis Of Therapeutics*, 10*th ed.*, Mc-Graw-Hill, New York, 2001; *Physician's Desk Reference* (60$^{th}$ ed., 2006), which is incorporated herein by reference in its entirety.

The compound of the invention and the one or more additional anticancer therapeutics can be administered separately, simultaneously, or sequentially. In various embodiments, the compound of the invention and the additional anticancer therapeutic are administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more anticancer therapeutics are administered within the same patient visit.

In certain embodiments, the compound of the invention and the additional anticancer therapeutic are cyclically administered. Cycling therapy involves the administration of one anticancer therapeutic for a period of time, followed by the administration of a second anticancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies.

In a preferred embodiment, the anticancer therapeutics are administered concurrently to a subject in separate compositions. The combination anticancer therapeutics of the invention may be administered to a subject by the same or different routes of administration.

In a specific embodiment, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

When a compound of the invention and the additional anticancer therapeutic are administered to a subject concurrently, the term "concurrently" is not limited to the administration of the anticancer therapeutics at exactly the same time, but rather, it is meant that they are administered to a subject in a sequence and within a time interval such that they can act together (e.g., synergistically to provide an increased benefit than if they were administered otherwise). For example, the anticancer therapeutics may be administered at the same time or sequentially in any order at different points in time; however, if not administered at the same time, they should be administered sufficiently close in time so as to provide the desired therapeutic effect, preferably in a synergistic fashion. The combination anticancer therapeutics of the invention can be administered separately, in any appropriate form and by any suitable route. When the components of the combination anticancer therapeutics are not administered in the same pharmaceutical composition, it is understood that they can be administered in any order to a subject in need thereof. For example, a compound of the invention can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the additional anticancer therapeutic, to a subject in need thereof. In various embodiments, the anticancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the anticancer therapeutics are administered within the same office visit. In another embodiment, the combination anticancer therapeutics of the invention are administered at 1 minute to 24 hours apart.

Formulations

The present invention provides compositions that are suitable for veterinary and/or human administration (e.g., pharmaceutical compositions). The pharmaceutical compositions of the present invention can be in any form that allows for the composition to be administered to a subject, said subject preferably being an animal, including, but not limited to a human, mammal, or non-human animal, such as a cow, horse, sheep, pig, fowl, cat, dog, mouse, rat, rabbit, guinea pig, etc., and is more preferably a mammal, and most preferably a human.

The formulation of a compound of the invention used in the prophylactic and/or therapeutic regimens which will be effective in the prevention, treatment, and/or management of cancer can be based on the currently available formulation. Alternatively the compounds can be reformulated based on knowledge within the art and the teachings herein. For example, the compound may be in the form of a solid, liquid or gas (aerosol). Typical routes of administration may include, without limitation, oral, topical, parenteral, sublingual, rectal, vaginal, ocular, intradermal, intratumoral, intracerebral, intrathecal, and intranasal. Parenteral administration includes subcutaneous injections, intravenous, intramuscular, intraperitoneal, intrapleural, intrasternal injection or infusion techniques. In a specific embodiment, the compositions are administered parenterally. In a more specific embodiment, the compositions are administered intravenously. Pharmaceutical compositions of the invention can be formulated so as to allow a compound of the invention to be bioavailable upon administration of the composition to a subject. Compositions can take the form of one or more dosage units, where, for example, a tablet can be a single dosage unit, and a container of a compound of the invention in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the overall health of the subject, the type of cancer the subject is in need of treatment of, the use of the composition as part of a multi-drug regimen, the particular form of the compound of the invention, the manner of administration, and the composition employed.

The pharmaceutically acceptable carrier or vehicle may be particulate, so that the compositions are, for example, in tablet or powder form. The carrier(s) can be liquid, with the compositions being, for example, an oral syrup or injectable liquid or topical cream. In addition, the carrier(s) can be gaseous, so as to provide an aerosol composition useful in, e.g., inhalatory administration.

The term "carrier" refers to a diluent, adjuvant or excipient, with which a compound of the invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a subject, the compounds of the invention and pharmaceutically acceptable carriers are sterile. Water is a preferred carrier when the compound of the invention is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The composition may be intended for oral administration, and if so, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as ethyl cellulose, carboxymethylcellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the pharmaceutical composition is in the form of a capsule, e.g., a gelatin capsule, it can contain, in addition to materials of the above type, a liquid carrier such as polyethylene glycol, cyclodextrin or a fatty oil.

The pharmaceutical composition can be in the form of a liquid, e.g., an elixir, syrup, solution, emulsion or suspension. The liquid can be useful for oral administration or for topical administration or for delivery by injection. When intended for oral administration, a composition can comprise one or more of a sweetening agent, preservatives, dye/colorant and flavour enhancer. In a composition for administration by injection, one or more of a surfactant, preservative, wetting agent, dispersing agent, suspending agent, buffer, stabilizer and isotonic agent can also be included.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in an ampoule, a disposable syringe or a multiple-dose vial made of glass, plastic or other material. Physiological saline is a preferred adjuvant. An injectable composition is preferably sterile.

The pharmaceutical compositions comprise an effective amount of a compound of the invention such that a suitable dosage will be obtained. The pharmaceutical compositions may comprise the known effective amount of the compounds as currently prescribed for their respective disorders.

Typically, the effective amount is at least 0.01% of a compound of the invention by weight of the composition. When intended for oral administration, this amount can be varied to be between 0.1% and 80% by weight of the composition. Preferred oral compositions can comprise from between 4% and 50% of the compound of the invention by weight of the composition. Preferred compositions of the present invention are prepared so that a parenteral dosage unit contains from between 0.01% and 2% by weight of the compound of the invention.

The compounds of the invention can be administered by any convenient route, for example, by infusion or bolus injection, by absorption through epithelial or mucocutaneous linings (e.g., oral mucosa, rectal and intestinal mucosa, etc.). Administration can be systemic or local. Various delivery systems are known, e.g., microparticles, microcapsules, capsules, etc., and may be useful for administering a compound of the invention. In certain embodiments, more than one compound of the invention is administered to a subject. Methods of administration may include, but are not limited to, oral administration and parenteral administration; parenteral administration including, but not limited to, intradermal, intramuscular, intraperitoneal, intravenous, subcutaneous; intranasal, epidural, sublingual, intranasal, intracerebral, intraventricular, intrathecal, intravaginal, transdermal, rectally, by inhalation, or topically to the ears, nose, eyes, or skin. The preferred mode of administration is left to the discretion of the practitioner, and will depend in-part upon the site of the medical condition (such as the site of cancer, a cancerous tumor or a pre-cancerous condition).

In one embodiment, the compounds of the invention are administered parenterally. In a specific embodiment, the compounds of the invention are administered intravenously.

In specific embodiments, it can be desirable to administer one or more compounds of the invention locally to the area in need of treatment (e.g., location of the tumor or ischemic condition). This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as sialastic membranes, or fibers. In one embodiment, administration can be by direct injection at the site (or former site) of a cancer, tumor, or precancerous tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and carriers such as triglycerides.

In yet another embodiment, the compounds of the invention can be delivered in a controlled release system. In one embodiment, a pump can be used (see Sefton, *CRC Crit. Ref Biomed. Eng.* 1987, 14, 201; Buchwald et al., Surgery 1980, 88: 507; Saudek et al., *N. Engl. J. Med.* 1989, 321: 574). In another embodiment, polymeric materials can be used (see *Medical Applications of Controlled Release*, Langer and Wise (eds.), CRC Pres., Boca Raton, Fla., 1974; *Controlled Drug Bioavailability, Drug Product Design and Performance*, Smolen and Ball (eds.), Wiley, New York, 1984; Ranger and Peppas, *J. Macromol. Sci. Rev. Macromol. Chem.* 1983, 23, 61; see also Levy et al., *Science* 1985, 228, 190; During et al., *Ann. Neurol.,* 1989, 25, 351; Howard et al., *J. Neurosurg.,* 1989, 71, 105). In yet another embodiment, a controlled-release system can be placed in proximity of the target of the compounds of the invention, e.g., the brain, thus requiring only a fraction of the systemic dose (see, e.g., Goodson, in *Medical Applications of Controlled Release*, supra, vol. 2, 1984, pp. 115-138). Other controlled-release systems discussed in the review by Langer (*Science* 1990, 249, 1527-1533) can be used.

In another embodiment, polymeric materials can be used to achieve controlled or sustained release of the compounds of the invention (see, e.g., U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(m- ethyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable.

Whether in solid, liquid or gaseous form, the compositions of the present invention can comprise an additional active agent selected from among those including, but not limited to, an additional prophylactic agent, an additional therapeutic agent, an antiemetic agent, a hematopoietic colony stimulating factor, an adjuvant therapy, a vaccine or other immune stimulating agent, an antibody/antibody fragment-based agent, an anti-depressant and an analgesic agent. For instance in a particular embodiment, the pharmaceutical composition comprises a compound of the invention, an additional anti-cancer agent, and a pharmaceutically acceptable carrier or vehicle.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In addition, optionally associated with such kit or pharmaceutical pack will be instructions for use of such kit or pack.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (Danio rerio), (4th Ed., Univ. of Oregon Press, Eugene, 2000).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned in this specification are herein incorporated by reference to the same extent as if each independent publication, patent application, patent, and other reference was specifically and individually indicated to be incorporated by reference. In case of conflict, the present specification, including definitions, will control. In addition, the materials, methods, and examples are illustrative only and not intended to be limiting.

The following examples are provided merely as illustrative of various aspects of the invention and shall not be construed to limit the invention in any way.

Examples

Example 1

Materials and Methods

Peptide Synthesis

Hydrocarbon-stapled peptides corresponding to the BH3 domains of BCL-2 family proteins and their FITC-derivatives were synthesized, purified, and characterized by circular dichroism as previously described (see, e.g., Bird et al., *Methods Enzymol* 446, 369 (2008) and WO 2009/108261, incorporated herein by reference). All peptides were purified by liquid chromatography-mass spectroscopy to >95% purity and quantitated by amino acid analysis.

Anti-Apoptotic Protein Production

Recombinant and tagless MCL-1ΔNΔC, BCL-2ΔC, BCL-XLΔC, BCL-wΔC, and BFL1/A1ΔC were expressed and purified as previously described (Pitter et al., Methods Enzymol 446, 387 (2008), incorporated by reference). Briefly, transformed *Escherichia coli* BL21 (DE3) were cultured in ampicillin-containing Luria Broth and protein expression was induced with 0.5 mM isopropyl β-D-1-thiogalactopyranoside (IPTG). The bacterial pellet was resuspended in buffer (250 mM NaCl, 20 mM Tris, complete protease inhibitor tablet, pH 7.2), sonicated, and after centifugation at 45,000×g for 45 minutes, the supernatant was applied to a glutathione-agarose (Sigma) column and washed with PBS. On-bead digestion of GST-tagged proteins was accomplished by overnight incubation at room temperature in the presence of thrombin (75 units) in PBS (3 mL), and the cleaved proteins were purified by fast protein liquid chromatography (FPLC) using 150 mM NaCl, 50 mM Tris, pH 7.4 buffer conditions.

Fluorescence Polarization Binding Assays

Binding assays were performed as previously described (Pitter et al., Methods Enzymol 446, 387 (2008). Briefly, FITC-SAHB (50 nM) was added to serial dilutions of FPLC-purified recombinant protein in binding buffer (50 mM Tris, 100 mM NaCl, pH 8.0). For competition assays, serial dilutions of acetylated MCL-1 SAHBs were mixed with FITC-BAK SAHB (25 nM), followed by addition of MCL-1ΔNΔC (100 nM) diluted in binding buffer (50 mM Tris, 100 mM NaCl, pH 8.0). Multiwell plates were incubated in the dark at room temperature until equilibrium was reached and fluorescence polarization (mP units) was measured by microplate reader (SpectraMax, Molecular Devices). For direct binding experiments, dissociation constants (KD) were calculated by nonlinear regression analysis of dose-response curves using Prism software (Graphpad). For competition experiments, Ki values were determined by nonlinear regression analysis of dose-response curves using a one-site competition model.

Cytochrome c Release Assays

Mouse liver mitochondria (0.5 mg/mL) were isolated and cytochrome c release assays performed according to established methods (Pitter et al., Methods Enzymol 446, 387 (2008). Briefly, isolated mitochondria were incubated at 37° C. for 40 minutes in the presence of a serial dilution of MCL-1 SAHBs, singly or in combination with BID BH3 peptide. The pellet and supernatant fractions were isolated by centifugation, and cytochrome c was quantitated using a colorimetric ELISA assay (R&D Systems). Percent cytochrome c released into the supernatant (% cytocsup) from releasable mitochondrial pools was calculated according to the following equation: % cytoc=[(cytocsup-cytocbackgr)/(cytoctotal-cytocbackgr)]*100, where background release represents cytochrome c detected in the supernatant of vehicle-treated (1% DMSO) samples and total release represents cytochrome c measured in 1% Triton-X 100 treated samples.

MCL-1 Immunoprecipitation Assay

OPM2 cells ($1\times10^7$) were incubated with vehicle or MCL-1 SAHB at the indicated concentrations in Opti-MEM medium (Invitrogen) at 37° C. for 4 hours. Cells were washed once with cold PBS and lysed on ice with 500 µL of cold NP-40 lysis buffer (50 mM Tris pH 7.4, 150 mM NaCl, 1 mM EDTA, 1 mM DTT, 0.5% NP40, complete protease inhibitor pellet). Cellular debris was pelleted at 14,000 g for 10 minutes at 4° C. and the supernatant was collected and exposed to pre-equilibrated protein A/G sepharose beads. The pre-cleared supernatant was incubated with anti-MCL-1 antibody (S-19, Santa Cruz Biotechnology) overnight at 4° C., followed by the addition of protein A/G sepharose beads for 1 hour. The beads were then pelleted, washed with NP-40 lysis buffer (3×) for 10 minutes at 4° C., and protein sample eluted from the beads by heating at 90° C. for 10 minutes in SDS loading buffer. The immunoprecipitates were subjected to electrophoresis and western analysis using NT anti-BAK antibody (CalBioChem).

Cell Viability Assay

OPM2 multiple myeloma cells and Jurkat T-cell leukemia were passaged and maintained in RPMI 1640 medium (Invitrogen) supplemented with 10% fetal bovine serum, 100 U/mL penicillin, 100 µg/mL streptomycin, 2 mM L-glutamine, 50 mM HEPES and 50 µM β-mercaptoethanol. For viability testing, OPM2 and Jurkat cells ($4\times10^4$) were treated with the indicated agents in Opti-MEM media at 37° C. in a final volume of 100 µL. Cell viability was measured at 24 hours by MTT assay, for which cells were incubated with 20 µL thiazolyl blue tetrazolium bromide (5 mg/mL in DPBS) at 37° C. for 4 hours, the precipitate solubilized with 0.1 N HCl isopropanol (100 µL), and absorbance measured at 570 nm and 650 nm. For synergy studies with TRAIL or FasL, cells were treated simultaneously with MCL-1 SAHB and the death receptor ligands in the presence or absence of. the pan-caspase inhibitor z-VAD (50 µM), which was administered to the cells 30 minutes prior to treatment with the pro-apoptotic agents.

Capsase 3/7 Activation Assay

OPM2 and Jurkat cells ($2\times10^4$ cells) were treated with the indicated agents in Opti-MEM media at 37° C. in a final volume of 50 Caspase 3/7 activation was measured at 4 hours using the ApoONE Caspase 3/7 kit according to the manufacturer's instructions (Promega). For synergy studies with TRAIL and FASL, cells were treated simultaneously with MCL-1 SAHB and the death receptor ligands.

Example 2

Design. Synthesis, and Optimization of MCL-1 Targeting SAHBs

A library of Stabilized Alpha-Helices of BCL-2 domains (SAHBs) was generated based upon the primary amino acid sequence of BCL-2 homology BH3 domains across all BCL-2 family subgroups, including multidomain anti-apoptotic, multidomain pro-apoptotic, and BH3-only (FIG. 7). Non-natural amino acids containing olefinic side chains were synthesized and then inserted into the target peptide sequence at i(i+4) positions as previously described (Walensky et al *Science* 2004, Bird et al *Methods in Enzymology* 2008). SAHBs were synthesized using solid phase Fmoc chemistry followed by ruthenium catalyzed olefin methathesis using the Grubbs first-generation catalyst. Peptides were derivatized at the amino-terminus with fluorescein (for binding and imaging studies) or acetylated at the amino-terminus, deprotected, cleaved and purified by LC/MS. LC/MS and amino acid analysis were used to determine peptide composition and purity.

To measure the binding activity of SAHBs for MCL-1, fluorescence polarization binding assays were performed (FIG. 8). To generate a stable MCL-1 protein suitable for such binding studies (i.e., the published full-length and carboxy-terminus deleted forms of recombinant MCL-1 degrade rapidly, rendering it difficult to maintain a homogenous solution of pure MCL-1 protein), a recombinant form of MCL-1 (rMCL-1) was produced that lacked its amino- and carboxy-terminus, "MCL-1ΔNΔC", but retained the critical BCL-2 homology domains and adjoining protein sequences that give rise to the BH3-binding cleft (SEQ ID NO: 72). The pGEX-4T vector was used to produce the GST-fusion protein of MCL-1ΔNΔC and purification was achieved by glutathione sepharose chromatography, affinity tag cleavage with thrombin at room temperature overnight, followed by size exclusion chromatography. Serial dilutions of MCL-1ΔNΔC in 50 mM Tris pH 8, 150 mM NaCl were incubated with a fixed concentration of FITC-derivatized SAHB (10-50 nM) until equilibrium was reached. Fluorescence polarization was measured on a BMG POLARstar Optima or Spectramax and dissociation constants determined by nonlinear regression analysis using Prism software 4.0 (Graphpad) (FIG. 8). This assay identified MCL-1 binders and distinguished them from non-binders (FIG. 9A).

Compounds that bound MCL-1 with high affinity were analyzed for MCL-1 selectivity by measuring SAHB affinities for recombinant BCL-$X_L$ΔC, BCL-WΔC and BFL-1/A1ΔC (FIG. 8B). Recombinant carboxy-terminal deleted anti-apoptotic proteins were expressed using the pGEX-4T vector, and purified as described for rMCL-1. The purified proteins were incubated with FITC-SAHBs, and binding affinities were analyzed by fluorescence polarization assay as described above. A discrete subset of SAHBs was determined to exhibit striking selectivity for MCL-1ΔNΔC (e.g. MCL-1 SAHB, NOXA SAHB) as demonstrated in FIG. 9B. BOK SAHB exhibited a significant preference for MCL-1, as compared to the other anti-apoptotics. It was also demonstrated that site-directed amino acid mutagenesis could readily be applied to convert a pan-anti-apoptotic binder, BIM SAHB, into a selective MCL-1 binder (FIG. 15). These results established a foundation for design of tailored SAHBs based upon the desired anti-apoptotic selectivity, such as high affinity pan-anti-apoptotic binders (e.g., BAK SAHB, BIM SAHB) and their MCL-1 specific analogs (e.g., SEQ ID NO: 69 and SEQ ID NOs: 61-62, respectively). Optionally, design and optimization of tailored SAHB compounds for anti-apoptotic targeting also employed computational modeling. Potent and specific compounds (e.g., MCL-1 SAHB) were also optimized by sampling staple positions along the length of the peptide sequence (FIG. 11A), yielding, for example, MCL-1 SAHBs with up to 6-fold enhancement in MCL-1 binding activity (FIG. 11C).

Example 2

MCL-1-Targeting SAHBs Exhibited Enhanced Alpha-Helicity, Protease Resistance, and Cellular Penetrance Alpha-helicity To evaluate secondary structure improvements of hydrocarbon-stapled peptides, circular dichroism (CD) spectra were recorded and analyzed on an Aviv Biomedical spectrometer (model 410), as has been previously reported (Walensky et al Science, 2004; Bird et al. Methods in Enzymology, 2008). Generally, short peptides do not exhibit significant α-helical structure in solution because the entropic cost of maintaining a conformationally restricted structure is not overcome by the enthalpic gain from hydrogen bonding of the peptide backbone. Indeed, unmodified BH3 peptides were found to display α-helical propensities of less than 20% (18% for MCL-1 BH3, FIG. 12), whereas installation of a chemical staple typically enhanced α-helicity of MCL-1 targeting SAHBs by at least 3-5 fold, with MCL-1 SAHBs displaying percent helical content that ranged from 55-100% (FIG. 12). The α-helicity of MCL-1 targeting SAHBs were compared to their unmodified counterparts by CD. A total of five scans from 190-260 nm in 0.5 nm increments with 0.5 sec averaging time were collectively averaged to obtain each spectrum using a 1 mm path length cell. The target peptide concentration for CD studies was 25-50 μM in 50 mM potassium phosphate (pH 7.5) or Milli-Q deionized water, and exact concentrations were confirmed by quantitative amino acid analysis of two CD sample dilutions. The CD spectra were initially plotted as wavelength versus millidegree. Once the precise peptide concentration was confirmed, the mean residue ellipticity [θ], in units of degree·cm²·dmol⁻¹·residue⁻¹, was derived from the equation, [θ]=millidegree/molar concentration/number of amino acid residues. After conversion to mean residue ellipticity, percent α-helicity was calculated using the equation, % helicity=$100 \times [\theta]_{222}/^{max}[\theta]_{222}$, where $^{max}[\theta]_{222}=-40,000\times[1-(2.5/\text{number of amino acid residues})]$. Curve-fitting CDDN software was also used to calculate the relative fractions of secondary structure including α-helix, parallel and antiparallel β-sheet, β-turn and random coil.

Protease Resistance

In vitro proteolytic degradation was measured by LC/MS (Agilent 1200) using the following parameters: 20 μL injection, 0.6 mL flow rate, 15 min run time consisting of a gradient of water (0.1% formic acid) to 20-80% acetonitrile (0.075% formic acid) over 10 min, 4 min wash to revert to starting gradient conditions, and 0.5 min post-time. The DAD signal was set to 280 nm with an 8 nm bandwidth and MSD set to scan mode with one channel at (M+2H)/2, ±1 mass units and the other at (M+3H)/3, ±1 mass units. Integration of each MSD signal yielded areas under the curve of >10⁸ counts. Reaction samples were composed of 5 μL peptide in DMSO (1 mM stock) and 195 μL of buffer consisting of 50 mM phosphate buffer pH 7.4 containing 2 mM CaCl₂. Upon injection of the 0 hr time point sample, 2 μL of 50 ng/μL chymotrypsin (Sigma) was added and the amount of intact peptide quantitated by serial injection over time. An internal control of acetylated tryptophan carboxamide at a concentration of 100 μM was used to normalize each MSD data point. A plot of MSD area versus time yielded an exponential decay curve and half-lives were determined by nonlinear regression analysis using Prism software (GraphPad).

Cell Penetrance

Flow cytometry based studies were used as an initial high throughput screen to determine cellular permeability of MCL-1 targeting SAHBs. FITC-SAHBs reconstituted with DMSO were diluted in serum-free media. Jurkat cells (50,000) were incubated with SAHBs in serum-free media at a concentration of 1-10 μM for 1-4 hours at 37° C. in duplicate. After the indicated time point, the cells were pelleted, washed with PBS, treated with trypsin for 5 minutes to cleave surface proteins (thereby removing any surface-bound FITC-SAHBs) and finally quenched with 10% FBS media. The cells were washed with PBS and resuspended in FACS buffer. Cellular fluorescence was measured using a FACSCalibur flow cytometer (Becton Dickinson) and analyzed with FlowJo software (Tree Star). The fluorescence intensity was measured for 10,000 events in triplicate and documented robust fluorescence of cells treated with FITC-MCL-1 targeting SAHBs, but not those exposed to the corresponding FITC-unmodified peptides.

In addition to FACS-based analysis, live confocal microscopy was used to visualize cellular uptake and intracellular localization of MCL-1 targeting SAHBs. For live confocal microscopy, Jurkat cells were incubated with FITC-SAHB and live cell organelle markers (e.g., dextran to label pinosomes, Mitotracker to label mitochondria). At defined time points (e.g., 4, 8, 12, and 24 hours), cells were washed twice with PBS, resuspended in PBS, wet mounted and imaged by confocal microscopy. Jurkat cells treated with FITC-MCL-1 SAHB and FITC-NOXA SAHB, for example, exhibited striking fluorescence of pinosomes at early time points and subsequent colocalization with Mitotracker, the site of outer mitochondrial membrane-embedded BCL-2 family proteins, such as anti-apoptotic MCL-1. Cell permeability and intracellular targeting can also be optimized through site-directed mutagenesis; for example, converting negatively charged residues to neutral or positively charged residues (e.g. SEQ ID NO: 39) can enhance cellular uptake as was previously reported (Bernal et al JACS, 2007).

Example 3

X-Ray Crystallographic Analysis of an MCL-1 SAHB/MCL-1ΔNΔC Complex Detailed the Molecular Interactions of the MCL-1 Binding Interface To determine the structure of the MCL-1 SAHB/MCL-1 binding interface, MCL-1ΔNΔC (6.3 mg/mL) was incubated with MCL-1 SAHB at a 1:1 ratio, and crystallization conditions were screened using 96-well sitting drop plates (Crystal Quick, Hampton Research) set up using the Screenmaker by Innovadyne Technologies. Initial screening conditions employed HT Index Screen (Hampton Research), JSCG+ Suite (Qiagen) and Pro-Complex Suite (Qiagen). Screening around the best hit was performed to identify the optimal condition for crystal growth. Formed crystals were removed, washed in the crystallization buffer and analyzed by SDS/PAGE and mass spectroscopy to verify the presence of the protein and peptide within the crystal. Co-complex crystals were soaked in cyroprotectant, flash frozen, and stored in liquid nitrogen. Initial diffraction patterns were measured at the MIT Department of Biology X-ray source and subsequently at the Argonne National Laboratory synchrotron facility. Phases were obtained by molecular replacement followed by data analysis and refinement (Phaser, Phenix, and Coots software). The MCL-1 SAHB/MCL-1ΔNΔC structure was compared and contrasted to that of MCL-1 with other BH3 domains (e.g., NOXA, BIM) to isolate unique features of the selective MCL-1 SAHB interaction. Unique MCL-1 SAHB contacts that dictate MCL-1 specificity are exploited to optimize SAHB selectivities and form the basis for the design of small molecule MCL-1 modulators (see above). To confirm the specificity of the binding interface, point mutations in the SAHB and/or MCL-1 protein were generated to evaluate the impact of discrete residue changes on the binding interaction, as measured by fluorescence polarization. Inactivating SAHB point mutations were particularly informative as negative controls for in vitro, cell-based, and in vivo studies (see below).

Example 4

MCL-1 Targeting SAHBs Displaced BAK SAHB from Recombinaint MCL-1 and Sensitized Mitochondrial Apoptosis In Vitro Three in vitro assays were used to verify the capacity of selective MCL-1-targeting SAHBs to sensitize mitochondrial apoptosis. First, SAHBs were tested for their ability to dissociate FITC-BAK SAHB from MCL-1ΔNΔC in a competitive FP assay, in which a serial dilution of acetylated test SAHB was added to a solution of FITC-BAK SAHB (e.g. 25 nM) in 50 mM Tris pH 7.4, 100 nM NaCl, to which MCL-1ΔNΔC (e.g., 250 nM) was then added. FP (mP units) was measured at equilibrium by microplate reader (e.g., Spectramax) and $K_i$ values calculated by nonlinear regression analysis of dose-response curves using Prism software (Graphpad). Effective dose-dependent competition for MCL-1ΔNΔC was exhibited by a panel of MCL-1 SAHBs (FIG. 16). Compounds that successfully displaced BAK SAHB were advanced to a mitochondrial assay in which the ability to disrupt the native MCL-1/BAK complex was monitored by MCL-1 immunoprecipitation. Wild-type mouse liver mitochondria (MLM) were isolated as described (Pitter et al. *Methods in Enzymology*, 2008) and treated with vehicle, MCL-1 SAHB, or MCL-1 SAHB mutant, followed by protein extraction, MCL-1 immunoprecipitation, and BAK western analysis. Compounds that disrupted the native MCL-1/BAK interaction, as demonstrated by the absence of co-immunoprecipitated BAK, were advanced to mitochondrial cytochrome c release assays, which were performed according to a previously published method (Pitter et al. *Methods in Enzymology*, 2008). Serial dilutions of test SAHB were exposed to wild-type MLM alone or in the presence of a BAK activator, such as BID BH3. Mitochondria exposed to vehicle or 1% Triton X-100 alone served as negative and positive controls, respectively. The experimental mixtures were incubated at room temperature for 40 min, and then the plates centrifuged at 3000 rpm for 10 min at 4° C. to pellet the mitochondria. The relative amount of cytochrome c released into the supernatant was quantified by ELISA assay per the manufacturer's protocol (Roche®). All experimental conditions were also tested on (1) $Bak^{-/-}$ mitochondria to ensure that the observed cytochrome c release from wild-type mitochondria derived from BAK activation and on (2) $Mcl-1^{-/-}$ mitochondria to confirm that the molecule's sensitization activity derived from MCL-1 targeting. The capacity of MCL-1 $SAHB_E$ to dose-responsively sensitize wild-type MLM, but not $Bak^{-/-}$ MLM, to BID BH3-triggered mitochdonrial apoptosis was demonstrated, as shown in the histograms of FIG. 16B.

Example 5

MCL-1 Targeting SAHBs Dissociated MCL-1/BAK In Situ and Sensitized Cancer Cells to Apoptosis Induction To link MCL-1-targeting SAHB activity with its capacity to specifically engage MCL-1 in situ, U937 AML cells were treated with FITC-conjugated SAHB followed by cellular lysis and SAHB retrieval by (1) anti-FITC pull-down, performed as reported (Walensky et al. *Mol Cell*, 2006; Pitter et al. *Methods in Enzymology*, 2008), or by (2) streptavidin-based biotin-SAHB pull down. For the latter approach, cancer cells were treated with SAHBs (5-20 μm) in serum free medium followed by serum replacement at 2-4 hours, and after incubation at various time points (e.g., 4, 8, 24 hours), cells were harvested and treated with lysis buffer. Lysates were then exposed to streptavidin agarose and incubated at 4° C. for 1 hour. The beads were washed with lysis buffer, heated to 90° C. for 10 minutes in SDS loading buffer and analyzed by Western analysis for the variety of anti-apoptotic proteins. The lysates were also evaluated by SDS/PAGE, Silver Stain Plus (Biorad) and tandem mass spectrometry. Bands that appeared in SAHB-exposed lysates, but not those treated with vehicle or SAHB point mutant, were excised with a razor and minced. The minced bands were washed once with water and twice with 25 mM ammonium bicarbonate for 10 minutes at room temperature. The bands were incubated with 1% hydroxide in 25 mM ammonium bicarbonate for 5 minutes to remove the silver stain. Once the gel slices were clear, the gel was washed in water, 1% formic acid, 50:50 water:acetonitrile with 1% formic acid, followed by acetonitrile for 5 minutes each. The gel slice was then subjected to proteolytic digestion, extraction, and tandem mass spectrometry (MSMS).

To evaluate the impact of targeting MCL-1 protein interactions in situ, MCL-1 over-expressing cancer cells, such as OPM2 multiple myeloma and U937 AML cells, ($10 \times 10^6$) were incubated with vehicle or the MCL-1 targeting SAHB (e.g. MCL-1 $SAHB_E$, NOXA $SAHB_D$) in serum-free media at 37° C. for 4 hours, followed by serum replacement for 6 hours. After cellular lysis in 50 mM Tris (pH 7.4), 150 mM NaCl, 1 mM EDTA, 1% CHAPS and complete protease inhibitor pellet, cellular debris was pelleted at 14,000 g for 10 minutes at 4° C. The supernatant was incubated with pre-equilibrated protein A/G sepharose beads. The pre-cleared supernatant was treated with anti-MCL-1 antibody for 1.5 hours at 4° C. with rotation, followed by exposure to the protein A/G sepharose beads for 1 hour. The beads were pelleted and washed with lysis buffer for 10 minutes at 4° C. The washed beads were pelleted, heated to 90° C. for 10 minutes in SDS loading buffer, analyzed by SDS/PAGE, and immunoblotted for the known MCL-1 interactor, BAK. In each case, incubation of the cells with the MCL-1 targeting SAHBs, MCL-1 $SAHB_E$ and NOXA $SAHB_D$, resulted in the dissociation of BAK from MCL-1 (FIGS. 16C, 17A). The SAHB-induced dissociation of MCL-1/BAK correlated with sensitization of U937 cells to apoptosis induction by a pro-apoptotic stimulus (see below).

A cell-based screen was used to evaluate the pro-apoptotic activity of MCL-1-targeting SAHBs in MCL-1-dependent hematologic cancer cell lines, including U937 (histiocytic lymphoma), Pfeiffer (diffuse large B-cell lymphoma), OCI-AML3 (acute myeloid leukemia), K562 (chronic myelogenous leukemia) and OPM-2 (multiple myeloma) cells. These cell lines, which represent a cross section of hematologic malignancies, overexpress MCL-1 and were previously found only to be sensitive to ABT-737 upon siRNA reduction of MCL-1 levels (Chen et al., 2007). Briefly, the cells were treated with MCL-1-selective SAHBs alone or in combination with BIM SAHB (or other pro-apoptotic stimulus, such as subtherapeutic doxorubicin, etoposide, dexamethasone), and then cell viability was evaluated by MTT assay as described (Pitter et al., 2008; Walensky et al., 2004) and exemplified in FIG. 17B. Whereas MCL-1 SAHB$_E$ and NOXA SAHB$_D$ had no toxic effect when administered alone, both compounds dose-responsively sensitized U937 AML cells to apoptosis induction by BIM SAHB, a broad-acting BCL-2 family modulator. MCL-1-selective SAHBs that decreased cell viability in combination with pro-apoptotic stimuli were then screened for cellular apoptosis sensitization by annexin V binding and FACS analysis, and by cell fractionation-based mitochondrial cytochrome c release, as described (Gavathiotis et al., 2008).

Example 6

Design, Synthesis, and Optimization of Further MCL-1 Targeting SAHBs

After the experiments set forth above, further members of the library of stabilized alpha-helices of BCL-2 domains (SAHBs) modeled after the BH3 domains of BCL-2 family proteins were generated in order to identify potent and selective inhibitors of MCL-1. The native alpha-helical structure of BH3 domains was reinforced by incorporating non-natural amino acids containing olefin tethers at the (i, i+4) positions of the non-interacting face, followed by ruthenium catalyzed olefin metathesis to yield a panel of stapled BH3 domains (FIG. 7). Fluorescence polarization assays (FPA) were performed to measure the binding affinity of fluorescently labeled SAHBs for recombinant human MCL-1ΔNΔC (amino acids 172-320), a deletion construct that contains the BH3-binding pocket and affords enhanced expression, purity, and stability. SAHBs corresponding to the BH3 domains of (1) BH3-only proteins NOXA, PUMA, BID, and BIM, (2) multi-domain pro-apoptotics BOK, BAX and BAK, and (3) anti-apoptotic MCL-1 itself exhibited high affinity binding for MCL-1 (Kd<50 nM) (FIG. 14B). To identify MCL-1-selective SAHBs, we first screened for recombinant BCL-XLΔC binding, which eliminated PUMA, BID, BIM, BOK, BAX, and BAK SAHBs and then for recombinant BFL1/A1ΔC binding, which eliminated NOXA SAHB. Indeed, binding analysis of MCL-1 SAHB using an expanded panel of anti-apoptotic proteins, including MCL-1ΔNΔC, BCL-2ΔC, BCL-XLΔC, BCL-wΔC and BFL-1/A1ΔC, confirmed that MCL-1 SAHB displayed potent and selective binding affinity for MCL-1 alone ($K_D$, 43 nM) (FIG. 9A).

Example 7

Characterization of MCL-1 Specific Peptides

To define the binding and specificity determinants for the interaction between the MCL-1 BH3 helix and MCL-1ΔNΔC, we performed alanine scanning, site-directed mutagenesis, and staple scanning Amino acid residues within MCL-1 SAHB were sequentially replaced with alanine and the corresponding fluorescently labeled SAHBs were tested for MCL-1ΔNΔC binding by FPA. The alanine scan was supplemented with glutamate mutagenesis of alanine and glycine residues. Whereas mutagenesis of N- and C-terminal residues had little to no impact on MCL-1ΔNΔC binding affinity, alanine mutagenesis of Leu213, Arg214, Val216, Gly217, Asp218 and Val220 decreased the binding affinity of MCL-1 SAHB for MCL-1ΔNΔC by 10- to 100-fold, revealing the key MCL-1 BH3 residues for MCL-1ΔNΔC engagement (FIG. 10). Comparative analysis of BH3 domain sequences indicated that the combination of core hydrophobic residues Leu213, Val216, and Val220 is unique to MCL-1 BH3 (FIG. 10) and alanine mutagenesis of any one of these hydrophobic residues is especially detrimental to MCL-1ΔNΔC binding. Interestingly, BAD BH3, which exhibits a restricted binding profile to BCL-2, BCL-XL, and BCL-w, and BIM BH3, which broadly engages anti-apoptotic proteins, possess a phenylalanine at the position corresponding to Val220 in MCL-1 BH3 (FIG. 14A). Scanning mutagenesis of the BIM BH3 sequence previously documented that replacement of this phenylalanine with alanine, glutamate, or lysine abrogated BCL-XL binding but had minimal impact on MCL-1 binding. We find that a single V220F point mutation in MCL-1 SAHB abolished selectivity for MCL-1ΔNΔC, conferring binding activity to both MCL-1ΔNΔC ($K_D$, 191 nM) and BCL-XLΔC ($K_D$, 89 nM) (FIG. 14B). Whereas select binding determinants such as the conserved amino acids Leu213, Arg214, Gly217, and Asp218 are shared among many BH3 domains, other discrete residues in the appropriate context, such as Val220 in MCL-1 BH3, can dictate selectivity.

We next performed a "staple scan" that effectively replaced pairs of amino acid residues within the BH3 sequence with crosslinked norleucine-like side chains to (1) address which surface along the MCL-1 BH3 helix is essential to MCL-1ΔNΔC engagement and (2) sample alternate staple positions to identify constructs with optimal α-helicity and binding activity for biological studies. In agreement with the alanine scan, mutagenesis of residues E211, 8215, G219, Q221, N223, and A227, and insertion of staples at i, i+4 pairings of these sites, did not disrupt the MCL-1ΔNΔC interaction (FIG. 11C). However, placement of the crosslink at positions G217 to Q221 abrogated binding activity, consistent with disruption of a critical hydrophobic interface between MCL-1 SAHB and MCL-1ΔNΔC by the hydrocarbon staple. Among the MCL-1 SAHBs generated, MCL-1 SAHBD exhibited the second highest □-helical content (91%) and the strongest binding activity (KD, 10 nM), achieving 4-fold enhancement in MCL-1ΔNΔC affinity compared to the parental MCL-1 SAHBA while retaining MCL-1ΔNΔC selectivity (FIGS. 11B, 13).

Example 8

Analysis of Mutagenesis Data in View of Crystal Structure

Analysis of the three-dimensional structure revealed that MCL-1 SAHB$_D$ is an alpha-helix that engages MCL-1ΔNΔC at the canonical BH3-binding groove comprised of helices α2 (BH3) and portions of a3, α4, α5 (BH1), and α8 (BH2). Hydrophobic residues Leu213, Val216, Gly217, and Val220 of MCL-1 SAHB$_D$ make direct contact with the hydrophobic groove at the surface of MCL-1ΔNΔC, consistent with the negative ramifications of alanine mutagenesis of these amino acids (FIG. 15A). The hydrophobic interactions are reinforced by complementary electrostatic pairings of MCL-1

SAHB$_D$ Arg214 and Asp218 with MCL-1ΔNΔC Asp256 and Arg263, respectively. These charged residues of MCL-1 SAHB$_D$ reside in hydrogen bond networks consisting of MCL-1ΔNΔC Asp256, Val253, Arg263 and His252 for Arg214 and MCL-1ΔNΔC Arg263 and Asn260 for Asp218.

The differential binding activities of MCL-1 SAHBs A-E are consistent with the structure of the MCL-1 SAHBD/MCL-1ΔNΔC complex. MCL-1 SAHB$_C$ is the only construct that exhibits poor binding activity and, based on the structure, it bears the only staple location (G217, Q221) that would sterically clash with the binding surface. Interestingly, the hydrocarbon staple of MCL-1 SAHB$_D$, whose alkene functionality is in cis conformation, makes discrete hydrophobic contacts with the perimeter of the MCL-1ΔNΔC binding site. A methyl group of the α,α-dimethyl functionality occupies a groove consisting of MCL-1ΔNΔC Gly262, Phe318, and Phe319, and additional contacts are also evident for the aliphatic side chain. Thus, the superior binding affinity of MCL-1 SAHB$_D$ may derive both from its enhanced α-helicity (FIGS. 15C, 18) and the recruitment of additional hydrophobic contacts by the staple itself. Indeed, these structural data highlight the potential to harness the staple functionality to optimize the potency of SAHB ligands while retaining their natural biological specificities.

Example 9

Analysis of Sensitization of Mitochondrial Apoptosis In Vitro

We next conducted a series of functional studies to determine if MCL-1 SAHB$_D$ could effectively target MCL-1 and sensitize mitochondrial apoptosis in vitro and in cells using methods such as those to test MCL-1 SAHB$_E$ described above. We first performed a competitive FPA to measure the capacity of MCL-1 SAHB$_D$ to dissociate a BAK BH3 helix from MCL-1ΔNΔC, simulating the displacement activity required for in situ function. Consistent with the direct binding data (FIG. 13), MCL-1 SAHB$_D$ was most effective at antagonizing the interaction between FITC-BAK SAHB and MCL-1ΔNΔC (FIG. 16A). To determine if the ability of MCL-1 SAHB$_D$ to disrupt the FITC-BAK SAHB/MCL-1ΔNΔC complex translated into SAHB-mediated sensitization of BAK-induced cytochrome c release, mitochondrial assays were performed as described.

Wild-type mouse liver mitochondria that contain BAK were exposed to BID BH3, a direct activator of BAK, in the presence and absence of a serial dilution of MCL-1 SAHB$_D$. Whereas MCL-1 SAHB$_D$ had no effect on the mitochondria in the absence of BID BH3, addition of MCL-1 SAHB$_D$ or SAHB$_E$ to BID BH3-exposed mitochondria triggered dose-responsive enhancement of BAK-mediated cytochrome c release (FIG. 16B and data not shown). To confirm that cytochrome c release specifically derived from BAK activation, the identical experiment was performed with Bak$^{-/-}$ mitochondria, and no release was observed (FIG. 16B). To extend these findings to a cellular context, we tested the ability of MCL-1 SAHB$_D$ to dissociate native MCL-1/BAK complexes. OPM2 multiple myeloma cells were treated with vehicle or increasing concentrations of MCL-1 SAHBD, followed by cellular extraction and anti-MCL-1 immunoprecipitation. BAK western analysis revealed co-immunoprecipitation of MCL-1/BAK from vehicle-treated cells but dose-responsive dissociation of the MCL-1/BAK interaction by MCL-1 SAHB$_D$ (FIG. 16C). Taken together, these mechanistic data demonstrate that MCL-1 SAHB$_D$ can disrupt the inhibitory MCL-1/BAK interaction in vitro and in cells, and sensitize BAK-mediated mitochondrial cytochrome c release.

Example 10

MCL-1-Specific SAHB Peptides Sensitize Caspase-Dependent Cellular Apoptosis

Importantly, selective liberation of pro-apoptotic proteins from MCL-1 may not activate cellular apoptosis if alternative anti-apoptotics are present to bind and neutralize them. From a functional standpoint, a selective MCL-1 inhibitor would instead be expected to phenocopy the pro-apoptotic activity of MCL-1 knockdown by siRNA, for example in the context when elimination of MCL-1, as opposed to modulation of MCL-1 activity (which may also be achieved by SAHB but not by siRNA), is desired. Thus, to examine the functional consequences of selective pharmacologic blockade of MCL-1 in cells, we tested the capacity of MCL-1 SAHB$_D$ to sensitize cancer cells to death receptor agonists that are specifically neutralized by MCL-1, as documented by siRNA-mediated MCL-1 knockdown. Jurkat T-cell leukemia and OPM2 cells were first exposed to serial dilutions of MCL-1 SAHBD and the extrinsic pathway activators TRAIL and Fas ligand (FasL) as single agents to obtain baseline viability measurements by MTT assay at 24 hours (FIGS. 18A, 18B). MCL-1 SAHB$_D$ had no effect on cell viability even at 40 μM dosing. Jurkat cells exhibited dose-responsive cytotoxicity in response to both TRAIL and FasL, whereas OPM2 cells were sensitive to TRAIL but not FasL (FIG. 19A). To determine if direct and selective MCL-1 blockade could sensitize the cells to TRAIL- and FasL-induced apoptosis, a serial dilution of MCL-1 SAHB$_D$ was combined with low-dose death receptor ligands. MCL-1 SAHBD dose-responsively sensitized Jurkat cells to both TRAIL and FasL, and selectively sensitized OPM2 cells to TRAIL (FIG. 19). MCL-1 SAHBD had no effect on OPM2 cells exposed to FasL, consistent with the observed resistance of OPM2 cells to FasL treatment (FIG. 19A).

To confirm that MCL-1 SAHB$_D$-induced sensitization was caspase-dependent, cell viability testing was also conducted in the presence of the pan-caspase inhibitor, z-VAD, which completely abrogated the negative effects on cell viability (FIG. 19A). Consistent with these data, MCL-1 SAHB$_D$ triggered dose-responsive caspase 3/7 activation when used in combination with low dose TRAIL and FasL in Jurkat cells and with TRAIL but not FasL in OPM2 cells (FIG. 19B). Importantly, BFL-1 SAHB$_A$, which displayed no binding activity toward anti-apoptotic proteins, did not sensitize Jurkat cells to TRAIL or FasL (FIG. 20). In addition, NOXA SAHB$_B$, a stapled NOXA BH3 helix with a sequence distinct from MCL-1 SAHBD but that also binds MCL-1ΔNΔC exclusively, behaved identically to MCL-1 SAHB$_D$ in this sensitization study (FIG. 21B). These cellular data demonstrate that MCL-1 SAHB$_D$ is a selective, cell-permeable MCL-1 antagonist, which sensitizes cancer cells to apoptotic stimuli that are suppressed by MCL-1. Thus, MCL-1 selective SAHBs are demonstrated to be effective when used in combination with a diversity of pro-apoptotic stimulants such as TRAIL and FasL (FIGS. 17-21) or with BCL-2 family targeted agents such as SAHBs that exhibit non-MCL-1 selective activity (FIG. 23, e.g. combination of BAD and MCL-1 SAHBs) or more broad apoptotic protein targeting (FIG. 17; e.g. combination of NOXA and BIM SAHBs).

Example 11

Analysis of Binding of a Truncated MCL-1-SAHB$_A$ to MCL-1ΔNΔC

A truncated MCL1-SAHBG (LRXVGDXV, residues 1-8 of SEQ ID NO: 31) was generated and tested for binding of MCL-1ΔNΔC using fluorescence polarization assay as set forth above. The stapled 9 amino acid stabilized peptide was found to bind to MCL-1 SAHB (FIG. 22). This demonstrates that a core consensus sequence is sufficient to promote binding to MCL-1.

REFERENCES

Adams, J. M., and S. Cory. 1998. The Bcl-2 protein family: arbiters of cell survival. *Science.* 281:1322-6.

Armstrong, S. A., A. L. Kung, M. E. Mabon, L. B. Silverman, R. W. Stam, M. L. Den Boer, R. Pieters, J. H. Kersey, S. E. Sallan, J. A. Fletcher, T. R. Golub, J. D. Griffin, and S. J. Korsmeyer. 2003. Inhibition of FLT3 in MLL. Validation of a therapeutic target identified by gene expression based classification. *Cancer Cell.* 3:173-83.

Bakhshi, A., J. P. Jensen, P. Goldman, J. J. Wright, O. W. McBride, A. L. Epstein, and S. J. Korsmeyer. 1985. Cloning the chromosomal breakpoint of t(14;18) human lymphomas: clustering around JH on chromosome 14 and near a transcriptional unit on 18. *Cell.* 41:899-906.

Chen, S., Y. Dai, H. Harada, P. Dent, and S. Grant. 2007. Mcl-1 down-regulation potentiates ABT-737 lethality by cooperatively inducing Bak activation and Bax translocation. *Cancer Res.* 67:782-91.

Cheng Y W, Lee H, Shiau M Y, Wu T C, Huang T T, Chang Y H. Human papillomavirus type 16/18 up-regulates the expression of interleukin-6 and antiapoptotic Mcl-1 in non-small cell lung cancer. Clin Cancer Res. 2008 Aug. 1; 14(15):4705-12.

Cleary, M. L., and J. Sklar. 1985. Nucleotide sequence of a t(14;18) chromosomal breakpoint in follicular lymphoma and demonstration of a breakpoint-cluster region near a transcriptionally active locus on chromosome 18. *Proc Natl Acad Sci USA.* 82:7439-43.

Danial, N. N., and S. J. Korsmeyer. 2004. Cell death: critical control points. *Cell.* 116:205-19.

Danial, N. N., L. D. Walensky, C. Y. Zhang, C. S. Choi, J. K. Fisher, A. J. Molina, S. R. Datta, K. L. Pitter, G. H. Bird, J. D. Wikstrom, J. T. Deeney, K. Robertson, J. Morash, A. Kulkarni, S, Neschen, S. Kim, M. E. Greenberg, B. E. Corkey, O. S. Shirihai, G. I. Shulman, B. B. Lowell, and S. J. Korsmeyer. 2008. Dual role of proapoptotic BAD in insulin secretion and beta cell survival. *Nat. Med.* 14:144-53.

Deng, J., N. Carlson, K. Takeyama, P. Dal Cin, M. Shipp, and A. Letai. 2007. BH3 profiling identifies three distinct classes of apoptotic blocks to predict response to ABT-737 and conventional chemotherapeutic agents. *Cancer Cell.* 12:171-85.

Derenne, S., B. Monia, N. M. Dean, J. K. Taylor, M. J. Rapp, J. L. Harousseau, R. Bataille, and M. Amiot. 2002. Antisense strategy shows that Mcl-1 rather than Bcl-2 or Bcl-x(L) is an essential survival protein of human myeloma cells. *Blood.* 100:194-9.

Ding, Q., X. He, W. Xia, J. M. Hsu, C. T. Chen, L. Y. Li, D. F. Lee, J. Y. Yang, X. Xie, J. C. Liu, and M. C. Hung. 2007. Myeloid Cell Leukemia-1 Inversely Correlates with Glycogen Synthase Kinase-3 {beta} Activity and Associates with Poor Prognosis in Human Breast Cancer. Cancer Res. 67:4564-".

Gavathiotis, E., M. Suzuki, M. L. Davis, K. Pitter, G. H. Bird, S. G. Katz, H. C. Tu, H. Kim, E. H. Cheng, N. Tjandra, and L. D. Walensky. 2008. BAX activation is initiated at a novel interaction site. *Nature.* 455:1076-81.

Green, D. R. 2005. Apoptotic pathways: ten minutes to dead. *Cell.* 121:671-4.

Hasan, Z, Ashraf M, Tayyebi A, Hussain R. *M. leprae* inhibits apoptosis in THP-1 cells by downregulation of Bad and Bak and upregulation of Mcl-1 gene expression. BMC Microbiol 2006, 6:78.

Hussain S R, Cheney C M, Johnson A J, Lin T S, Greyer M R, Caligiuri M A, Lucas D M, Byrd J C. Mcl-1 is a relevant therapeutic target in acute and chronic lymphoid malignancies: down-regulation enhances rituximab-mediated apoptosis and complement-dependent cytotoxicity. Clin Cancer Res. 2007 Apr. 1; 13(7):2144-50.

Kim S H, Ricci M S, El-Deiry W S. Mcl-1: a gateway to TRAIL sensitization. Cancer Res. 2008 Apr. 1; 68(7):2062-4.

Kline, M. P., S. V. Rajkumar, M. M. Timm, T. K. Kimlinger, J. L. Haug, J. A. Lust, P. R. Greipp, and S. Kumar. 2007. ABT-737, an inhibitor of Bcl-2 family proteins, is a potent inducer of apoptosis in multiple myeloma cells. *Leukemia.* 21:1549-60.

Konopleva, M., R. Contractor, T. Tsao, I. Samudio, P. P. Ruvolo, S. Kitada, X. Deng, D. Zhai, Y. X. Shi, T. Sneed, M. Verhaegen, M. Soengas, V. R. Ruvolo, T. McQueen, W. D. Schober, J. C. Watt, T. Jiffar, X. Ling, F. C. Marini, D. Harris, M. Dietrich, Z. Estrov, J. McCubrey, W. S. May, J. C. Reed, and M. Andreeff. 2006. Mechanisms of apoptosis sensitivity and resistance to the BH3 mimetic ABT-737 in acute myeloid leukemia. *Cancer Cell.* 10:375-88.

Lin X, Morgan-Lappe S, Huang X, Li L, Zakula D M, Vernetti L A, Fesik S W, Shen Y. 'Seed' analysis of off-target siRNAs reveals an essential role of Mcl-1 in resistance to the small-molecule Bcl-2/Bcl-XL inhibitor ABT-737. Oncogene. 2007 Jun. 7; 26(27):3972-9.

Lock, R., H. Carol, P. J. Houghton, C. L. Morton, E. A. Kolb, R. Gorlick, C. P. Reynolds, J. M. Maris, S. T. Keir, J. Wu, and M. A. Smith. 2008. Initial testing (stage 1) of the BH3 mimetic ABT-263 by the pediatric preclinical testing program. *Pediatr Blood Cancer.* 50:1181-9.

Oltersdorf, T., S. W. Elmore, A. R. Shoemaker, R. C. Armstrong, D. J. Augeri, B. A. Belli, M. Bruncko, T. L. Deckwerth, J. Dinges, P. J. Hajduk, M. K. Joseph, S. Kitada, S. J. Korsmeyer, A. R. Kunzer, A. Letai, C. Li, M. J. Mitten, D. G. Nettesheim, S. Ng, P. M. Nimmer, J. M. O'Connor, A. Oleksijew, A. M. Petros, J. C. Reed, W. Shen, S. K. Tahir, C. B. Thompson, K. J. Tomaselli, B. Wang, M. D. Wendt, H. Zhang, S. W. Fesik, and S. H. Rosenberg. 2005. An inhibitor of Bcl-2 family proteins induces regression of solid tumours. *Nature.* 435:677-81.

Perez-Galan, P., G. Roue, N. Villamor, E. Campo, and D. Colomer. 2007. The BH3-mimetic GX15-070 synergizes with bortezomib in mantle cell lymphoma by enhancing Noxa-mediated activation of Bak. *Blood.* 109:4441-9.

Pitter, K., F. Bernal, J. L. LaBelle, and L. D. Walensky. 2008. Chapter 23 Dissection of the BCL-2 Family Signaling Network with Stabilized alpha-Helices of BCL-2 Domains. *Methods Enzymol.* 446:387-408.

Rajalingam K, Sharma M, Lohmann C, Oswald M, Thieck O, Froelich C J, Rudel T. Mcl-1 is a key regulator of apoptosis resistance in *Chlamydia trachomatis*-infected cells. PLoS ONE. 2008 Sep. 1; 3(9):e3102.

Reed, J. C. 1998. Bcl-2 family proteins. *Oncogene.* 17:3225-36.

Sattler, M., H. Liang, D. Nettesheim, R. P. Meadows, J. E. Harlan, M. Eberstadt, H. S. Yoon, S. B. Shuker, B. S. Chang, A. J. Minn, C. B. Thompson, and S. W. Fesik. 1997. Structure of Bcl-xL-Bak peptide complex: recognition between regulators of apoptosis. *Science.* 275:983-6.

Schulze-Bergkamen H, Fleischer B, Schuchmann M, Weber A, Weinmann A, Krammer P H, Galle P R. Suppression of Mcl-1 via RNA interference sensitizes human hepatocellular carcinoma cells towards apoptosis induction. *BMC Cancer.* 2006 Oct. 2; 6:232.

Shoemaker, A. R., M. J. Mitten, J. Adickes, S. Ackler, M. Refici, D. Ferguson, A. Oleksijew, J. M. O'Connor, B. Wang, D. J. Frost, J. Bauch, K. Marsh, S. K. Tahir, X. Yang, C. Tse, S. W. Fesik, S. H. Rosenberg, and S. W. Elmore. 2008. Activity of the Bcl-2 family inhibitor ABT-263 in a panel of small cell lung cancer xenograft models. *Clin Cancer Res.* 14:3268-77.

Sly L M, Hingley-Wilson S M, Reiner N E, McMaster W R. Survival of *Mycobacterium tuberculosis* in host macrophages involves resistance to apoptosis dependent upon induction of antiapoptotic Bcl-2 family member Mcl-1. *Immunol.* 2003 Jan. 1; 170(1):430-7.

Thallinger C, Wolschek M F, Maierhofer H, Skvara H, Pehamberger H, Monia B P, Jansen B, Wacheck V, Selzer E. Mcl-1 is a novel therapeutic target for human sarcoma: synergistic inhibition of human sarcoma xenotransplants by a combination of mcl-1 antisense oligonucleotides with low-dose cyclophosphamide. *Clin Cancer Res.* 2004 Jun. 15; 10(12 Pt 1):4185-91.

Tse, C., A. R. Shoemaker, J. Adickes, M. G. Anderson, J. Chen, S. Jin, E. F. Johnson, K. C. Marsh, M. J. Mitten, P. Nimmer, L. Roberts, S. K. Tahir, Y. Xiao, X. Yang, H. Zhang, S. Fesik, S. H. Rosenberg, and S. W. Elmore. 2008. ABT-263: a potent and orally bioavailable Bcl-2 family inhibitor. *Cancer Res.* 68:3421-8.

Tsujimoto, Y., J. Gorham, J. Cossman, E. Jaffe, and C. M. Croce. 1985. The t(14;18) chromosome translocations involved in B-cell neoplasms result from mistakes in VDJ joining. *Science.* 229:1390-3.

van Delft, M. F., A. H. Wei, K. D. Mason, C. J. Vandenberg, L. Chen, P. E. Czabotar, S. N. Willis, C. L. Scott, C. L. Day, S. Cory, J. M. Adams, A. W. Roberts, and D. C. Huang. 2006. The BH3 mimetic ABT-737 targets selective Bcl-2 proteins and efficiently induces apoptosis via Bak/Bax if Mcl-1 is neutralized. *Cancer Cell.* 10:389-99.

Walensky, L. D., A. L. Kung, I. Escher, T. J. Malia, S. Barbuto, R. D. Wright, G. Wagner, G. L. Verdine, and S. J. Korsmeyer. 2004. Activation of apoptosis in vivo by a hydrocarbon-stapled BH3 helix. *Science.* 305:1466-70.

Walensky, L. D., K. Pitter, J. Morash, K. J. Oh, S. Barbuto, J. Fisher, E. Smith, G. L. Verdine, and S. J. Korsmeyer. 2006. A stapled BID BH3 helix directly binds and activates BAX. *Mol. Cell.* 24:199-210.

Zhang, B., I. Gojo, and R. G. Fenton. 2002. Myeloid cell factor-1 is a critical survival factor for multiple myeloma. *Blood.* 99:1885-93.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

We claim:

1. A peptide comprising an amino acid sequence that is at least 90% identical to RKALETLRRVGDGVQRNHETAF (SEQ ID NO: 93) wherein the peptide comprises a stabilized alpha-helix with non-natural amino acids comprising a hydrocarbon staple between relative positions i and i+3, i and i+4, or i and i+7 of the peptide.

2. The peptide of claim 1, wherein the peptide comprises a sequence selected from the group consisting of RKALETLRRVGDGVXRNHXTAF (SEQ ID NO: 27), RKXLETXRRVGDGVQRNHETAF (SEQ ID NO: 28), RKALETLRXVGDXVQRNHETAF (SEQ ID NO: 74), RKALXTLRXVGDGVQRNHETAF (SEQ ID NO: 26), RKALETLRRVGDGVQRXHETXF (SEQ ID NO: 75), KALETLRRVGDGVXRNHXTAF (SEQ ID NO: 21), KXLETXRRVGDGVQRNHETAF (SEQ ID NO: 25), KALETLRXVGDXVQRNHETAF (SEQ ID NO: 74), KALXTLRXVGDGVQRNHETAF (SEQ ID NO: 19), and KALETLRRVGDGVQRXHETXF (SEQ ID NO: 22) wherein the X's are any amino acid.

3. The peptide of claim 2, wherein each X is non-natural amino acid comprising a hydrocarbon staple.

4. The peptide of claim 1, wherein the peptide comprises an affinity for MCL-1 of at least 50 μM.

* * * * *

UNITED STATES PATENT AND TRADEMARK OFFICE
CERTIFICATE OF CORRECTION

PATENT NO. : 9,079,970 B2  
APPLICATION NO. : 13/133883  
DATED : July 14, 2015  
INVENTOR(S) : Loren D. Walensky and Michelle L. Stewart Page 1 of 1

It is certified that error appears in the above-identified patent and that said Letters Patent is hereby corrected as shown below:

On the title page item 56, Other Publications, Line 8, delete "Characterizaton" and insert
-- Characterization --;

In the claims

Column 138, Claim 2, Line 21, delete "74" and insert -- 18 --.

Signed and Sealed this
Ninth Day of August, 2016

Michelle K. Lee
*Director of the United States Patent and Trademark Office*

SEQUENCE LISTING

```
<160> NUMBER OF SEQ ID NOS: 94

<210> SEQ ID NO 1
<211> LENGTH: 350
<212> TYPE: PRT
<213> ORGANISM: Homo sapiens

<400> SEQUENCE: 1
```

Met Phe Gly Leu Lys Arg Asn Ala Val Ile Gly Leu Asn Leu Tyr Cys
1               5                   10                  15

Gly Gly Ala Gly Leu Gly Ala Gly Ser Gly Gly Ala Thr Arg Pro Gly
            20                  25                  30

Gly Arg Leu Leu Ala Thr Glu Lys Glu Ala Ser Ala Arg Arg Glu Ile
        35                  40                  45

Gly Gly Gly Glu Ala Gly Ala Val Ile Gly Gly Ser Ala Gly Ala Ser
    50                  55                  60

Pro Pro Ser Thr Leu Thr Pro Asp Ser Arg Arg Val Ala Arg Pro Pro
65                  70                  75                  80

Pro Ile Gly Ala Glu Val Pro Asp Val Thr Ala Thr Pro Ala Arg Leu
                85                  90                  95

Leu Phe Phe Ala Pro Thr Arg Arg Ala Ala Pro Leu Glu Glu Met Glu
            100                 105                 110

Ala Pro Ala Ala Asp Ala Ile Met Ser Pro Glu Glu Glu Leu Asp Gly
        115                 120                 125

-continued

Tyr Glu Pro Glu Pro Leu Gly Lys Arg Pro Ala Val Leu Pro Leu Leu
    130                 135                 140

Glu Leu Val Gly Glu Ser Gly Asn Asn Thr Thr Asp Gly Ser Leu
145                 150                 155                 160

Pro Ser Thr Pro Pro Ala Glu Glu Glu Asp Asp Leu Tyr Arg
                165                 170                 175

Gln Ser Leu Glu Ile Ile Ser Arg Tyr Leu Arg Glu Gln Ala Thr Gly
                180                 185                 190

Ala Lys Asp Thr Lys Pro Met Gly Arg Ser Gly Ala Thr Ser Arg Lys
            195                 200                 205

Ala Leu Glu Thr Leu Arg Arg Val Gly Asp Gly Val Gln Arg Asn His
210                 215                 220

Glu Thr Ala Phe Gln Gly Met Leu Arg Lys Leu Asp Ile Lys Asn Glu
225                 230                 235                 240

Asp Asp Val Lys Ser Leu Ser Arg Val Met Ile His Val Phe Ser Asp
                245                 250                 255

Gly Val Thr Asn Trp Gly Arg Ile Val Thr Leu Ile Ser Phe Gly Ala
                260                 265                 270

Phe Val Ala Lys His Leu Lys Thr Ile Asn Gln Glu Ser Cys Ile Glu
            275                 280                 285

Pro Leu Ala Glu Ser Ile Thr Asp Val Leu Val Arg Thr Lys Arg Asp
290                 295                 300

Trp Leu Val Lys Gln Arg Gly Trp Asp Gly Phe Val Glu Phe Phe His
305                 310                 315                 320

Val Glu Asp Leu Glu Gly Gly Ile Arg Asn Val Leu Leu Ala Phe Ala
                325                 330                 335

Gly Val Ala Gly Val Gly Ala Gly Leu Ala Tyr Leu Ile Arg
            340                 345                 350

<210> SEQ ID NO 2
<211> LENGTH: 54
<212> TYPE: PRT
<213> ORGANISM: Homo sapiens

<400> SEQUENCE: 2

Met Pro Gly Lys Lys Ala Arg Lys Asn Ala Gln Pro Ser Pro Ala Arg
1               5                   10                  15

Ala Pro Ala Glu Leu Glu Val Glu Cys Ala Thr Gln Leu Arg Arg Phe
                20                  25                  30

Gly Asp Lys Leu Asn Phe Arg Gln Lys Leu Leu Asn Leu Ile Ser Lys
            35                  40                  45

Leu Phe Cys Ser Gly Thr
    50

<210> SEQ ID NO 3
<211> LENGTH: 212
<212> TYPE: PRT
<213> ORGANISM: Homo sapiens

<400> SEQUENCE: 3

Met Glu Val Leu Arg Arg Ser Ser Val Phe Ala Ala Glu Ile Met Asp
1               5                   10                  15

Ala Phe Asp Arg Ser Pro Thr Asp Lys Glu Leu Val Ala Gln Ala Lys
                20                  25                  30

Ala Leu Gly Arg Glu Tyr Val His Ala Arg Leu Leu Arg Ala Gly Leu
            35                  40                  45

-continued

```
Ser Trp Ser Ala Pro Glu Arg Ala Ala Pro Val Pro Gly Arg Leu Ala
    50                  55                  60

Glu Val Cys Ala Val Leu Arg Leu Gly Asp Glu Leu Glu Met Ile
 65                  70                  75                  80

Arg Pro Ser Val Tyr Arg Asn Val Ala Arg Gln Leu His Ile Ser Leu
                 85                  90                  95

Gln Ser Glu Pro Val Val Thr Asp Ala Phe Leu Ala Val Ala Gly His
            100                 105                 110

Ile Phe Ser Ala Gly Ile Thr Trp Gly Lys Val Val Ser Leu Tyr Ala
        115                 120                 125

Val Ala Ala Gly Leu Ala Val Asp Cys Val Arg Gln Ala Gln Pro Ala
    130                 135                 140

Met Val His Ala Leu Val Asp Cys Leu Gly Glu Phe Val Arg Lys Thr
145                 150                 155                 160

Leu Ala Thr Trp Leu Arg Arg Gly Gly Trp Thr Asp Val Leu Lys
                165                 170                 175

Cys Val Val Ser Thr Asp Pro Gly Leu Arg Ser His Trp Leu Val Ala
            180                 185                 190

Ala Leu Cys Ser Phe Gly Arg Phe Leu Lys Ala Ala Phe Phe Val Leu
        195                 200                 205

Leu Pro Glu Arg
    210

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (13)..(13)
<223> OTHER INFORMATION: Any amino acid

<400> SEQUENCE: 4

Ile Trp Ile Ala Gln Glu Leu Arg Xaa Ile Gly Asp Xaa Phe Asn Ala
 1               5                  10                  15

Tyr Tyr Ala Arg Arg
            20

<210> SEQ ID NO 5
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (17)..(17)
<223> OTHER INFORMATION: Norleucine
```

```
<400> SEQUENCE: 5

Asp Ile Ile Arg Asn Ile Ala Arg His Leu Ala Xaa Val Gly Asp Xaa
1               5                   10                  15

Xaa Asp Arg Ser Ile Arg Arg
            20

<210> SEQ ID NO 6
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Norleucine
<220> FEATURE:
<221> NAME/KEY: MOD_RES
<222> LOCATION: (18)..(18)
<223> OTHER INFORMATION: Any amino acid

<400> SEQUENCE: 6

Asn Leu Trp Ala Ala Gln Arg Tyr Gly Arg Glu Leu Arg Xaa Xaa Ser
1               5                   10                  15

Asp Xaa Phe Val Asp Ser Phe Lys Lys
            20                  25

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (10)..(10)
<223> OTHER INFORMATION: Any amino acid

<400> SEQUENCE: 7

Leu Glu Val Glu Ser Xaa Thr Gln Leu Xaa Arg Phe Gly Asp Lys Leu
1               5                   10                  15

Asn Phe Arg Gln Lys Leu
            20

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (13)..(13)
<223> OTHER INFORMATION: Norleucine
```

```
<220> FEATURE:
<221> NAME/KEY: MOD_RES
<222> LOCATION: (16)..(16)
<223> OTHER INFORMATION: Any amino acid

<400> SEQUENCE: 8

Gln Trp Ala Arg Glu Ile Gly Ala Gln Leu Arg Xaa Xaa Ala Asp Xaa
1               5                   10                  15

Leu Asn Ala Gln Tyr
            20

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 9

Gln Val Gly Arg Gln Leu Ala Xaa Ile Gly Asp Xaa Ile Asn Arg Arg
1               5                   10                  15

Tyr Asp

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (16)..(16)
<223> OTHER INFORMATION: Any amino acid

<400> SEQUENCE: 10

Ala Ser Thr Lys Lys Leu Ser Glu Ser Leu Lys Xaa Ile Gly Asp Xaa
1               5                   10                  15

Leu Asp Ser Asn
            20

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
```

```
<221> NAME/KEY: MOD_RES
<222> LOCATION: (18)..(18)
<223> OTHER INFORMATION: Any amino acid

<400> SEQUENCE: 11

Arg Leu Ala Glu Val Ser Ala Val Leu Leu Xaa Leu Gly Asp Xaa Leu
1               5                   10                  15

Glu Xaa Ile Arg
            20

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 12

Lys Ala Leu Glu Thr Leu Arg Xaa Val Gly Asp Xaa Val Gln Arg Asn
1               5                   10                  15

His Glu Thr Ala Phe
            20

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 13

Val Val His Leu Thr Leu Arg Xaa Ala Gly Asp Xaa Phe Ser Arg Arg
1               5                   10                  15

Tyr

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 14
```

```
Ala Val Lys Gln Ala Leu Arg Xaa Ala Gly Asp Xaa Phe Glu Leu Arg
1               5                   10                  15

Tyr

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (11)..(11)
<223> OTHER INFORMATION: Any amino acid

<400> SEQUENCE: 15

Leu His Gln Ala Xaa Arg Xaa Ala Gly Asp Xaa Phe Glu Thr Arg Phe
1               5                   10                  15

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (13)..(13)
<223> OTHER INFORMATION: Any amino acid

<400> SEQUENCE: 16

Lys Glu Val Glu Lys Asn Leu Lys Xaa Ser Leu Asp Xaa Val Asn Val
1               5                   10                  15

Val Ser Val

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Ala Leu Glu Thr Leu Arg Arg Val Gly Asp Gly Val Gln Arg Asn
1               5                   10                  15

His Glu Thr Ala Phe
            20

<210> SEQ ID NO 18
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 18

Lys Ala Leu Glu Thr Leu Arg Xaa Val Gly Asp Xaa Val Gln Arg Asn
1               5                   10                  15

His Glu Thr Ala Phe
            20

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 19

Lys Ala Leu Xaa Thr Leu Arg Xaa Val Gly Asp Gly Val Gln Arg Asn
1               5                   10                  15

His Glu Thr Ala Phe
            20

<210> SEQ ID NO 20
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (14)..(14)
<223> OTHER INFORMATION: Any amino acid

<400> SEQUENCE: 20

Lys Ala Leu Glu Thr Leu Arg Arg Val Xaa Asp Gly Val Xaa Arg Asn
1               5                   10                  15

His Glu Thr Ala Phe
            20

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (14)..(14)
<223> OTHER INFORMATION: Any amino acid
<220> FEATURE:
<221> NAME/KEY: MOD_RES
<222> LOCATION: (18)..(18)
<223> OTHER INFORMATION: Any amino acid

<400> SEQUENCE: 21

Lys Ala Leu Glu Thr Leu Arg Arg Val Gly Asp Gly Val Xaa Arg Asn
1               5                   10                  15

His Xaa Thr Ala Phe
            20

<210> SEQ ID NO 22
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (20)..(20)
<223> OTHER INFORMATION: Any amino acid

<400> SEQUENCE: 22

Lys Ala Leu Glu Thr Leu Arg Arg Val Gly Asp Gly Val Gln Arg Xaa
1               5                   10                  15

His Glu Thr Xaa Phe
            20

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (13)..(13)
<223> OTHER INFORMATION: Norleucine

<400> SEQUENCE: 23

Ala Leu Ala Leu Arg Leu Ala Xaa Ile Gly Asp Xaa Xaa Asp Val Ser
1               5                   10                  15

Leu Arg Ala

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
```

```
<223> OTHER INFORMATION: Any amino acid
<220> FEATURE:
<221> NAME/KEY: MOD_RES
<222> LOCATION: (11)..(11)
<223> OTHER INFORMATION: Any amino acid

<400> SEQUENCE: 24

Glu Ala Ala Val Leu Arg Xaa Ala Ala Ala Xaa Leu Arg Gln Ile His
1               5                   10                  15

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 25

Lys Xaa Leu Glu Thr Xaa Arg Arg Val Gly Asp Gly Val Gln Arg Asn
1               5                   10                  15

His Glu Thr Ala Phe
            20

<210> SEQ ID NO 26
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (9)..(9)
<223> OTHER INFORMATION: Any amino acid

<400> SEQUENCE: 26

Arg Lys Ala Leu Xaa Thr Leu Arg Xaa Val Gly Asp Gly Val Gln Arg
1               5                   10                  15

Asn His Glu Thr Ala Phe
            20

<210> SEQ ID NO 27
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (19)..(19)
<223> OTHER INFORMATION: Any amino acid

<400> SEQUENCE: 27
```

```
Arg Lys Ala Leu Glu Thr Leu Arg Arg Val Gly Asp Gly Val Xaa Arg
1               5                   10                  15

Asn His Xaa Thr Ala Phe
            20

<210> SEQ ID NO 28
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 28

Arg Lys Xaa Leu Glu Thr Xaa Arg Arg Val Gly Asp Gly Val Gln Arg
1               5                   10                  15

Asn His Glu Thr Ala Phe
            20

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Ala Leu Glu Thr Leu Arg Arg Val Gly Asp Gly Val Gln Arg Asn
1               5                   10                  15

His Glu

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 30

Lys Ala Leu Glu Thr Leu Arg Xaa Val Gly Asp Xaa Val Gln Arg Asn
1               5                   10                  15

His Glu

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 31

Leu Arg Xaa Val Gly Asp Xaa Val Gln
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 32

Leu Arg Xaa Val Gly Asp Xaa Val
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 33

Phe Arg Xaa Val Gly Asp Xaa Val
1               5

<210> SEQ ID NO 34
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (18)..(18)
<223> OTHER INFORMATION: Any non-naturally occurring amino acid
<220> FEATURE:
<221> NAME/KEY: MOD_RES
<222> LOCATION: (19)..(19)
<223> OTHER INFORMATION: Any amino acid
```

```
<400> SEQUENCE: 34

Arg Lys Ala Leu Glu Thr Leu Arg Arg Val Gly Asp Gly Val Xaa Arg
1               5                   10                  15

Asn Xaa Xaa Thr Ala Phe
            20

<210> SEQ ID NO 35
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 35

Ala Ala Leu Glu Thr Leu Arg Xaa Val Gly Asp Xaa Val Gln Arg Asn
1               5                   10                  15

His Glu Thr Ala Phe
            20

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 36

Lys Glu Leu Glu Thr Leu Arg Xaa Val Gly Asp Xaa Val Gln Arg Asn
1               5                   10                  15

His Glu Thr Ala Phe
            20

<210> SEQ ID NO 37
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 37

Lys Ala Ala Glu Thr Leu Arg Xaa Val Gly Asp Xaa Val Gln Arg Asn
```

```
                        1               5                  10                 15

His Glu Thr Ala Phe
            20

<210> SEQ ID NO 38
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 38

Lys Ala Leu Ala Thr Leu Arg Xaa Val Gly Asp Xaa Val Gln Arg Asn
1               5                   10                  15

His Glu Thr Ala Phe
            20

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 39

Lys Ala Leu Glu Ala Leu Arg Xaa Val Gly Asp Xaa Val Gln Arg Asn
1               5                   10                  15

His Glu Thr Ala Phe
            20

<210> SEQ ID NO 40
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 40

Lys Ala Leu Glu Thr Ala Arg Xaa Val Gly Asp Xaa Val Gln Arg Asn
1               5                   10                  15

His Glu Thr Ala Phe
            20
```

```
<210> SEQ ID NO 41
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 41

Lys Ala Leu Glu Thr Leu Ala Xaa Val Gly Asp Xaa Val Gln Arg Asn
1               5                   10                  15

His Glu Thr Ala Phe
            20

<210> SEQ ID NO 42
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 42

Lys Ala Leu Glu Thr Leu Arg Xaa Ala Gly Asp Xaa Val Gln Arg Asn
1               5                   10                  15

His Glu Thr Ala Phe
            20

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 43

Lys Ala Leu Glu Thr Leu Arg Xaa Val Ala Asp Xaa Val Gln Arg Asn
1               5                   10                  15

His Glu Thr Ala Phe
            20

<210> SEQ ID NO 44
<211> LENGTH: 21
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 44

Lys Ala Leu Glu Thr Leu Arg Xaa Val Glu Asp Xaa Val Gln Arg Asn
1               5                   10                  15

His Glu Thr Ala Phe
            20

<210> SEQ ID NO 45
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 45

Lys Ala Leu Glu Thr Leu Arg Xaa Val Gly Ala Xaa Val Gln Arg Asn
1               5                   10                  15

His Glu Thr Ala Phe
            20

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 46

Lys Ala Leu Glu Thr Leu Arg Xaa Val Gly Asp Xaa Ala Gln Arg Asn
1               5                   10                  15

His Glu Thr Ala Phe
            20

<210> SEQ ID NO 47
<211> LENGTH: 21
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 47

Lys Ala Leu Glu Thr Leu Arg Xaa Val Gly Asp Xaa Phe Gln Arg Asn
1               5                   10                  15

His Glu Thr Ala Phe
            20

<210> SEQ ID NO 48
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 48

Lys Ala Leu Glu Thr Leu Arg Xaa Val Gly Asp Xaa Val Ala Arg Asn
1               5                   10                  15

His Glu Thr Ala Phe
            20

<210> SEQ ID NO 49
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 49

Lys Ala Leu Glu Thr Leu Arg Xaa Val Gly Asp Xaa Val Gln Ala Asn
1               5                   10                  15

His Glu Thr Ala Phe
            20

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
```

```
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 50

Lys Ala Leu Glu Thr Leu Arg Xaa Val Gly Asp Xaa Val Gln Arg Ala
1               5                   10                  15

His Glu Thr Ala Phe
            20

<210> SEQ ID NO 51
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 51

Lys Ala Leu Glu Thr Leu Arg Xaa Val Gly Asp Xaa Val Gln Arg Asn
1               5                   10                  15

Ala Glu Thr Ala Phe
            20

<210> SEQ ID NO 52
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 52

Lys Ala Leu Glu Thr Leu Arg Xaa Val Gly Asp Xaa Val Gln Arg Asn
1               5                   10                  15

His Ala Thr Ala Phe
            20

<210> SEQ ID NO 53
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
```

<223> OTHER INFORMATION: Any amino acid

<400> SEQUENCE: 53

Lys Ala Leu Glu Thr Leu Arg Xaa Val Gly Asp Xaa Val Gln Arg Asn
1               5                   10                  15

His Glu Ala Ala Phe
            20

<210> SEQ ID NO 54
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 54

Lys Ala Leu Glu Thr Leu Arg Xaa Val Gly Asp Xaa Val Gln Arg Asn
1               5                   10                  15

His Glu Thr Glu Phe
            20

<210> SEQ ID NO 55
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 55

Lys Ala Leu Glu Thr Leu Arg Xaa Val Gly Asp Xaa Val Gln Arg Asn
1               5                   10                  15

His Glu Thr Ala Ala
            20

<210> SEQ ID NO 56
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 56

```
Lys Ala Ala Glu Thr Leu Arg Xaa Val Gly Asp Xaa Phe Gln Arg Asn
1               5                   10                  15

His Glu Thr Ala Phe
            20

<210> SEQ ID NO 57
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (18)..(18)
<223> OTHER INFORMATION: Any amino acid

<400> SEQUENCE: 57

Lys Ala Ala Glu Thr Leu Arg Arg Val Gly Asp Gly Val Xaa Arg Asn
1               5                   10                  15

His Xaa Thr Ala Phe
            20

<210> SEQ ID NO 58
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (18)..(18)
<223> OTHER INFORMATION: Any amino acid

<400> SEQUENCE: 58

Lys Ala Ala Glu Thr Leu Arg Arg Val Gly Asp Gly Phe Xaa Arg Asn
1               5                   10                  15

His Xaa Thr Ala Phe
            20

<210> SEQ ID NO 59
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (14)..(14)
<223> OTHER INFORMATION: Any amino acid

<400> SEQUENCE: 59

Phe Ala Thr Glu His Asn Arg Gln Val Xaa Asp Gly Val Xaa Arg Leu
1               5                   10                  15

Thr Glu Leu Ala Lys
```

```
                          20

<210> SEQ ID NO 60
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 60

Phe Ala Thr Glu His Asn Arg Xaa Val Gly Asp Xaa Val Arg Arg Leu
1               5                   10                  15

Thr Glu Leu Ala Lys
            20

<210> SEQ ID NO 61
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 61

Ile Trp Ile Xaa Gln Glu Leu Xaa Arg Phe Gly Asp Lys Phe Asn Ala
1               5                   10                  15

Tyr Tyr Ala Arg
            20

<210> SEQ ID NO 62
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (13)..(13)
<223> OTHER INFORMATION: Any amino acid

<400> SEQUENCE: 62

Ile Trp Ile Ala Gln Glu Ala Arg Xaa Ile Gly Asp Xaa Ala Asn Ala
1               5                   10                  15

Tyr Tyr Ala Arg Arg
            20

<210> SEQ ID NO 63
```

```
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (15)..(15)
<223> OTHER INFORMATION: Any amino acid

<400> SEQUENCE: 63

Leu Glu Val Glu Ser Ala Thr Gln Leu Arg Xaa Phe Gly Asp Xaa Leu
1               5                   10                  15

Asn Phe Arg Gln Lys Leu
            20

<210> SEQ ID NO 64
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (10)..(10)
<223> OTHER INFORMATION: Any amino acid

<400> SEQUENCE: 64

Leu Glu Val Glu Ser Xaa Thr Gln Leu Xaa Arg Phe Gly Asp Lys Leu
1               5                   10                  15

Asn Phe Arg Gln Lys Leu
            20

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (10)..(10)
<223> OTHER INFORMATION: Any amino acid

<400> SEQUENCE: 65

Leu Glu Val Glu Ser Xaa Thr Gln Leu Xaa Arg Phe Gly Asp Lys Leu
1               5                   10                  15

Asn Phe

<210> SEQ ID NO 66
<211> LENGTH: 22
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 66

Leu Glu Val Xaa Ser Ala Thr Xaa Leu Arg Arg Phe Gly Asp Lys Leu
1               5                   10                  15

Asn Phe Arg Gln Lys Leu
            20

<210> SEQ ID NO 67
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (21)..(21)
<223> OTHER INFORMATION: Any amino acid

<400> SEQUENCE: 67

Leu Glu Val Glu Ser Ala Thr Gln Leu Arg Arg Phe Gly Asp Lys Leu
1               5                   10                  15

Xaa Phe Arg Gln Xaa Leu
            20

<210> SEQ ID NO 68
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (9)..(9)
<223> OTHER INFORMATION: Any amino acid

<400> SEQUENCE: 68

Leu Glu Val Glu Xaa Ala Thr Gln Xaa Arg Arg Phe Gly Asp Lys Leu
1               5                   10                  15

Asn Phe Arg Gln Lys Leu
            20

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
```

```
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 69

Gln Val Xaa Arg Gln Leu Xaa Arg Phe Gly Asp Lys Ile Asn Arg Arg
1               5                   10                  15

Tyr Asp

<210> SEQ ID NO 70
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (11)..(11)
<223> OTHER INFORMATION: Any amino acid

<400> SEQUENCE: 70

Val Gly Gln Leu Leu Gln Xaa Met Gly Asp Xaa Val Tyr Gln Gln Tyr
1               5                   10                  15

Arg Ser Leu Thr Arg
            20

<210> SEQ ID NO 71

<400> SEQUENCE: 71

000

<210> SEQ ID NO 72
<211> LENGTH: 271
<212> TYPE: PRT
<213> ORGANISM: Homo sapiens

<400> SEQUENCE: 72

Met Phe Gly Leu Lys Arg Asn Ala Val Ile Gly Leu Asn Leu Tyr Cys
1               5                   10                  15

Gly Gly Ala Gly Leu Gly Ala Gly Ser Gly Gly Ala Thr Arg Pro Gly
                20                  25                  30

Gly Arg Leu Leu Ala Thr Glu Lys Glu Ala Ser Ala Arg Arg Glu Ile
            35                  40                  45

Gly Gly Gly Glu Ala Gly Ala Val Ile Gly Gly Ser Ala Gly Ala Ser
    50                  55                  60

Pro Pro Ser Thr Leu Thr Pro Asp Ser Arg Arg Val Ala Arg Pro Pro
65                  70                  75                  80

Pro Ile Gly Ala Glu Val Pro Asp Val Thr Ala Thr Pro Ala Arg Leu
                85                  90                  95

Leu Phe Phe Ala Pro Thr Arg Arg Ala Ala Pro Leu Glu Glu Met Glu
                100                 105                 110

Ala Pro Ala Ala Asp Ala Ile Met Ser Pro Glu Glu Leu Asp Gly
            115                 120                 125

Tyr Glu Pro Glu Pro Leu Gly Lys Arg Pro Ala Val Leu Pro Leu Leu
        130                 135                 140
```

```
Glu Leu Val Gly Glu Ser Gly Asn Asn Thr Ser Thr Asp Gly Ser Leu
145                 150                 155                 160

Pro Ser Thr Pro Pro Pro Ala Glu Glu Glu Asp Asp Leu Tyr Arg
                165                 170                 175

Gln Ser Leu Glu Ile Ile Ser Arg Tyr Leu Arg Glu Gln Ala Thr Gly
            180                 185                 190

Ala Lys Asp Thr Lys Pro Met Gly Arg Ser Gly Ala Thr Ser Arg Lys
        195                 200                 205

Ala Leu Glu Thr Leu Arg Arg Val Gly Asp Gly Val Gln Arg Asn His
    210                 215                 220

Glu Thr Ala Phe Gln Gly Trp Val Cys Gly Val Leu Pro Cys Arg Gly
225                 230                 235                 240

Pro Arg Arg Trp His Gln Glu Cys Ala Ala Gly Phe Cys Arg Cys Cys
                245                 250                 255

Trp Ser Arg Ser Trp Phe Gly Ile Ser Asn Lys Ile Ala Leu Leu
                260                 265                 270

<210> SEQ ID NO 73
<211> LENGTH: 156
<212> TYPE: PRT
<213> ORGANISM: Homo sapiens

<400> SEQUENCE: 73

Asp Glu Leu Tyr Arg Gln Ser Leu Glu Ile Ile Ser Arg Tyr Leu Arg
1               5                   10                  15

Glu Gln Ala Thr Gly Ala Lys Asp Thr Lys Pro Met Gly Arg Ser Gly
            20                  25                  30

Ala Thr Ser Arg Lys Ala Leu Glu Thr Leu Arg Arg Val Gly Asp Gly
        35                  40                  45

Val Gln Arg Asn His Glu Thr Ala Phe Gln Gly Met Leu Arg Lys Leu
    50                  55                  60

Asp Ile Lys Asn Glu Asp Asp Val Lys Ser Leu Ser Arg Val Met Ile
65                  70                  75                  80

His Val Phe Ser Asp Gly Val Thr Asn Trp Gly Arg Ile Val Thr Leu
                85                  90                  95

Ile Ser Phe Gly Ala Phe Val Ala Lys His Leu Lys Thr Ile Asn Gln
            100                 105                 110

Glu Ser Cys Ile Glu Pro Leu Ala Glu Ser Ile Thr Asp Val Leu Val
        115                 120                 125

Arg Thr Lys Arg Asp Trp Leu Val Lys Gln Arg Gly Trp Asp Gly Phe
    130                 135                 140

Val Glu Phe Phe His Val Glu Asp Leu Glu Gly Gly
145                 150                 155

<210> SEQ ID NO 74
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (13)..(13)
<223> OTHER INFORMATION: Any amino acid
```

<400> SEQUENCE: 74

Arg Lys Ala Leu Glu Thr Leu Arg Xaa Val Gly Asp Xaa Val Gln Arg
1               5                   10                  15

Asn His Glu Thr Ala Phe
            20

<210> SEQ ID NO 75
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (21)..(21)
<223> OTHER INFORMATION: Any amino acid

<400> SEQUENCE: 75

Arg Lys Ala Leu Glu Thr Leu Arg Arg Val Gly Asp Gly Val Gln Arg
1               5                   10                  15

Xaa His Glu Thr Xaa Phe
            20

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Arg Arg Phe Gly Asp Lys Leu
1               5

<210> SEQ ID NO 77
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Glu Val Glu Ser Ala Thr Gln Leu Arg Arg Phe Gly Asp Lys Leu
1               5                   10                  15

Asn Phe Arg Gln Lys Leu
            20

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES

```
<222> LOCATION: (7)..(7)
<223> OTHER INFORMATION: Any amino acid

<400> SEQUENCE: 78

Leu Leu Xaa Leu Gly Asp Xaa Leu
1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 79

Leu Xaa Arg Phe Gly Asp Lys Phe
1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 80

Leu Xaa Arg Phe Gly Asp Lys Ile
1               5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 81

Leu Gln Xaa Met Gly Asp Xaa Tyr
1               5

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Any amino acid
<220> FEATURE:
```

```
<221> NAME/KEY: MOD_RES
<222> LOCATION: (15)..(15)
<223> OTHER INFORMATION: Any amino acid

<400> SEQUENCE: 82

Arg Leu Ala Glu Val Ser Ala Val Leu Leu Xaa Leu Gly Asp Xaa Leu
1               5                   10                  15

Glu

<210> SEQ ID NO 83
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 83

Ile Trp Ile Xaa Gln Glu Leu Xaa Arg Phe Gly Asp Lys Phe Asn Ala
1               5                   10                  15

Tyr Tyr Ala Arg
            20

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (11)..(11)
<223> OTHER INFORMATION: Any amino acid

<400> SEQUENCE: 84

Val Gly Gln Leu Leu Gln Xaa Met Gly Asp Xaa Tyr Gln Gln Tyr Arg
1               5                   10                  15

Ser Leu Thr Arg
            20

<210> SEQ ID NO 85
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
```

```
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (20)..(21)
<223> OTHER INFORMATION: Any amino acid

<400> SEQUENCE: 85

Xaa Xaa Leu Xaa Thr Leu Arg Xaa Val Gly Asp Xaa Val Xaa Arg Xaa
1               5                   10                  15

His Xaa Thr Xaa Xaa
            20

<210> SEQ ID NO 86
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Ala Leu Glu Thr Leu Arg Arg Val Gly Asp Gly Val Gln Arg Asn
1               5                   10                  15

His Glu Thr Ala Phe
            20

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Trp Ile Ala Gln Glu Leu Arg Arg Ile Gly Asp Glu Phe Asn Ala Tyr
1               5                   10                  15

Tyr

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid

<400> SEQUENCE: 88
```

```
Arg Tyr Gly Arg Glu Leu Arg Arg Xaa Ser Asp Glu Phe Val Asp Ser
1               5                   10                  15
Phe

<210> SEQ ID NO 89
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Glu Ser Ala Thr Gln Leu Arg Arg Phe Gly Asp Lys Leu Asn Phe Arg
1               5                   10                  15
Gln

<210> SEQ ID NO 90
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Glu Phe Ala Ala Gln Leu Arg Lys Ile Gly Asp Lys Val Tyr Cys Thr
1               5                   10                  15
Trp

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asp Glu Cys Ala Gln Leu Arg Arg Ile Gly Asp Lys Val Asn Leu Arg
1               5                   10                  15
Gln

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Lys Ala Leu Glu Thr Leu Arg Arg Val Gly Asp Gly Val Gln Arg Asn
1               5                   10                  15
His

<210> SEQ ID NO 93
<211> LENGTH: 22
<212> TYPE: PRT
<213> ORGANISM: Homo sapiens

<400> SEQUENCE: 93

Arg Lys Ala Leu Glu Thr Leu Arg Arg Val Gly Asp Gly Val Gln Arg
1               5                   10                  15
```

```
Asn His Glu Thr Ala Phe
            20

<210> SEQ ID NO 94
<211> LENGTH: 4
<212> TYPE: PRT
<213> ORGANISM: Unknown
<220> FEATURE:
<223> OTHER INFORMATION: Description of Unknown: "DEVD" motif peptide

<400> SEQUENCE: 94

Asp Glu Val Asp
1
```